United States Patent
Deisseroth et al.

(10) Patent No.: US 9,992,981 B2
(45) Date of Patent: Jun. 12, 2018

(54) OPTOGENETIC CONTROL OF REWARD-RELATED BEHAVIORS

(75) Inventors: Karl Deisseroth, Stanford, CA (US); Ilana Witten, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 57 days.

(21) Appl. No.: 13/882,670

(22) PCT Filed: Nov. 4, 2011

(86) PCT No.: PCT/US2011/059295
§ 371 (c)(1),
(2), (4) Date: Aug. 12, 2013

(87) PCT Pub. No.: WO2012/061688
PCT Pub. Date: May 10, 2012

(65) Prior Publication Data
US 2013/0317569 A1    Nov. 28, 2013

Related U.S. Application Data

(60) Provisional application No. 61/410,692, filed on Nov. 5, 2010.

(51) Int. Cl.
*A61N 5/06* (2006.01)
*A01K 67/027* (2006.01)
*A61K 38/17* (2006.01)
*G01N 33/50* (2006.01)

(52) U.S. Cl.
CPC ........ *A01K 67/0275* (2013.01); *A61K 38/177* (2013.01); *A61N 5/0618* (2013.01); *A61N 5/0622* (2013.01); *G01N 33/5088* (2013.01); *A01K 2227/105* (2013.01); *A01K 2267/03* (2013.01); *A61N 5/062* (2013.01)

(58) Field of Classification Search
CPC .. C12Q 1/00; A61K 2121/00; A61K 48/0058; A61K 38/177; C07K 14/47; A01K 67/0275; A01K 2227/105; A01K 2267/03; C12M 31/10; C12M 41/32; G01N 33/5088; A61N 5/0618; A61N 5/0622; A61N 5/062
See application file for complete search history.

(56) References Cited

U.S. PATENT DOCUMENTS

| | | |
|---|---|---|
| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |

(Continued)

FOREIGN PATENT DOCUMENTS

| | | |
|---|---|---|
| CN | 1079464 A | 12/1993 |
| CN | 1558222 A | 12/2004 |

(Continued)

OTHER PUBLICATIONS

Williams, Justin C., and Timothy Denison. "From optogenetic technologies to neuromodulation therapies." Science translational medicine 5.177 (2013): 177ps6-177ps6.*

(Continued)

*Primary Examiner* — Titilayo Moloye
(74) *Attorney, Agent, or Firm* — Bozicevic, Field & Francis LLP; Paula A. Borden

(57) ABSTRACT

Provided herein are compositions and methods for disrupting at least one reward-related behavior in an individual through the use of light-responsive opsin proteins used to control the polarization state of the cholinergic interneurons of the nucleus accumbens or the striatum.

15 Claims, 13 Drawing Sheets

(56) References Cited

U.S. PATENT DOCUMENTS

| | | |
|---|---|---|
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,696,722 B2 | 4/2014 | Deisseroth et al. |
| 8,815,582 B2 | 8/2014 | Deisseroth et al. |
| 8,906,360 B2 | 12/2014 | Deisseroth et al. |
| 8,926,959 B2 | 1/2015 | Deisseroth et al. |
| 9,057,734 B2 | 6/2015 | Cohen |
| 9,079,940 B2 | 7/2015 | Deisseroth et al. |
| 9,175,095 B2 | 11/2015 | Deisseroth et al. |
| 9,249,234 B2 | 2/2016 | Deisseroth et al. |
| 9,359,449 B2 | 6/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0267118 A1 | 12/2004 | Dawson |
| 2005/0020945 A1 | 1/2005 | Tosaya et al. |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1* | 6/2005 | Walker ............ C12Q 1/6876 514/44 R |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197935 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand et al. |
| 2007/0260295 A1 | 11/2007 | Chen et al. |
| 2007/0261127 A1 | 11/2007 | Boyden et al. |

(56) References Cited

U.S. PATENT DOCUMENTS

| | | |
|---|---|---|
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0088680 A1* | 4/2009 | Aravanis ............ A61K 48/005 604/21 |
| 2009/0093403 A1* | 4/2009 | Zhang ................ A01K 67/0333 514/8.1 |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0157145 A1 | 6/2009 | Cauller |
| 2009/0069261 A1 | 10/2009 | Nikolov et al. |
| 2009/0131837 A1 | 10/2009 | Zhang et al. |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0209352 A1 | 8/2010 | Hultman et al. |
| 2010/0234273 A1 | 9/2010 | Deisseroth et al. |
| 2011/0021270 A1 | 1/2011 | Vo-Dinh et al. |
| 2011/0092800 A1 | 4/2011 | Yoo et al. |
| 2011/0105998 A1 | 5/2011 | Deisseroth et al. |
| 2011/0112179 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0172653 A1 | 7/2011 | Deisseroth et al. |
| 2011/0233046 A1 | 9/2011 | Nikolenko et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0144359 A1 | 6/2013 | Kishawi et al. |
| 2013/0286181 A1 | 10/2013 | Betzig et al. |
| 2015/0112411 A1 | 4/2015 | Beckman et al. |

FOREIGN PATENT DOCUMENTS

| | | | |
|---|---|---|---|
| CN | 102076866 A | 5/2011 | |
| CN | 103313752 A | 9/2013 | |
| CN | 103476456 A | 12/2013 | |
| EP | 1197144 | 4/2002 | |
| EP | 1 334 748 | 8/2003 | |
| EP | 1444889 | 8/2004 | |
| EP | 1873566 | 1/2008 | |
| JP | 2006-295350 | 10/1994 | |
| JP | H 09505771 A | 6/1997 | |
| JP | 2004534508 | 11/2004 | |
| JP | 2005034073 A | 2/2005 | |
| JP | 2007530027 A | 11/2007 | |
| JP | 2008010422 A | 1/2008 | |
| JP | 2010227537 A | 10/2010 | |
| JP | 2012508581 | 4/2012 | |
| WO | WO 1995/005214 | 2/1995 | |
| WO | WO 1996/032076 | 10/1996 | |
| WO | WO 2000/027293 | 5/2000 | |
| WO | WO 2001-025466 | 4/2001 | |
| WO | WO 03/106486 A2 | 2/2003 | |
| WO | WO 2013/016486 | 2/2003 | |
| WO | WO 2003-040323 | 5/2003 | |
| WO | WO 2003/046141 | 6/2003 | |
| WO | WO 2003-084994 | 10/2003 | |
| WO | WO 2003-102156 | 12/2003 | |
| WO | WO 2004/033647 | 4/2004 | |
| WO | WO 2005/093429 | 10/2005 | |
| WO | WO 2006/103678 | 10/2006 | |
| WO | WO 2007-024391 | 3/2007 | |
| WO | WO 2007-131180 | 11/2007 | |
| WO | WO 2008/014382 | 1/2008 | |
| WO | WO 2008/086470 | 7/2008 | |
| WO | WO 2008/106694 | 9/2008 | |
| WO | WO 2009/025819 | 2/2009 | |
| WO | WO 2009/072123 | 6/2009 | |
| WO | WO 2009/119782 | 10/2009 | |
| WO | WO 2009-131837 | 10/2009 | |
| WO | WO 2009/148946 | 12/2009 | |
| WO | WO 2010/006049 | 1/2010 | |
| WO | WO 2010/011404 A3 | 1/2010 | |
| WO | WO 2010/056970 | 5/2010 | |
| WO | WO 2010056970 A3 * | 7/2010 | ........... C07K 14/705 |
| WO | WO-2010123993 | 10/2010 | |
| WO | WO 2011/005978 | 1/2011 | |
| WO | WO 2011005978 A9 * | 3/2011 | ......... A01K 67/0275 |
| WO | WO 2011/066320 A3 | 6/2011 | |
| WO | WO 2011/106783 | 9/2011 | |
| WO | WO 2011-116238 A2 | 9/2011 | |
| WO | WO 2011/127088 A3 | 10/2011 | |
| WO | WO 2012/032103 | 3/2012 | |
| WO | WO 2012/061676 | 5/2012 | |
| WO | WO2012/061681 | 5/2012 | |
| WO | WO2012/061684 | 5/2012 | |
| WO | WO2012/061688 | 5/2012 | |
| WO | WO2012/061690 | 5/2012 | |
| WO | WO 2012/061741 | 5/2012 | |
| WO | WO 2012/061744 | 5/2012 | |
| WO | 2012/106407 | 8/2012 | |
| WO | WO 2012/134704 A2 | 10/2012 | |
| WO | WO 2013/003557 | 1/2013 | |
| WO | WO 2013/090356 | 6/2013 | |
| WO | WO 2013/126521 | 8/2013 | |
| WO | WO 2013/126762 | 8/2013 | |
| WO | WO 2013/142196 | 9/2013 | |
| WO | WO 2014/081449 | 5/2014 | |
| WO | WO 2014/117079 | 7/2014 | |
| WO | WO 2016/019075 | 2/2016 | |

OTHER PUBLICATIONS

Knöpfel, T., and E. Boyden. "A comprehensive concept of optogenetics." Optogenetics: Tools for Controlling and Monitoring Neuronal Activity 196 (2012): 1.*

Soofiyani S et al. "Gene therapy, early promises, subsequent problems, and recent breakthroughs." Adv Pharm Bull. 2013;3(2):249-55.*

(56) References Cited

OTHER PUBLICATIONS

De Palma et al. "In vivo targeting of tumor endothelial cells by systemic delivery of lentiviral vectors."Hum Gene Ther. Aug. 10, 2003;14(12):1193-206.*
Day and Carelli "The Nucleus Accumbens and Pavlovian Reward Learning." Neuroscientist. Apr. 2007; 13(2): 148-159.*
Berlanga et al. "Cholinergic interneurons of the nucleus accumbens and dorsal striatum are activated by the self-administration of cocaine." Neuroscience. 2003;120(4):1149-56.*
Gradinaru et al. "eNpHR: a Natronomonas halorhodopsin enhanced for optogenetic applications." Brain Cell Biol. Aug. 2008;36(1-4):129-39. d.*
Packer, Adam M., Botond Roska, and Michael Häusser. "Targeting neurons and photons for optogenetics." Nature neuroscience 16.7 (2013): 805-815.*
Davidson and Breakefield. "Viral vectors for gene delivery to the nervous system." Nature Reviews Neuroscience 4, 353-364 (May 2003).*
Lin et al. "Study of the Circuitry of Nucleus Accumbens and its Effect on Addiction by Optogenetic Methods." Abstract 964. Neurosurgery Aug. 2010; 67 (2): 557.*
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Fenno et al., "The development and application of optogenetics", Annual Review of Neuroscience, 2011, vol. 34, No. 1, pp. 389-412.
Gunaydin et al., "Ultrafast optogenetic control", Nature Neuroscience, 2010, vol. 13, No. 3, pp. 387-392.
Hira et al., "Transcranial optogenetic stimulation for functional mapping of the motor cortex", J Neurosci Methods, 2009, vol. 179, pp. 258-263.
Lalumiere, R., "A new technique for controlling the brain: optogenetics and its potential for use in research and the clinic", Brain Stimulation, 2011, vol. 4, pp. 1-6.
Lin, "A user's guide to channelrhodopsin variants: features, limitations and future developments", Exp Physiol, 2010, vol. 96, No. 1, pp. 19-25.
Mancuso et al., "Optogenetic probing of functional brain circuitry", Experimental Physiology, 2010, vol. 96.1, pp. 26-33.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Pinkham et al., "Neural bases for impaired social cognition in schizophrenia and autism spectrum disorders", Schizophrenia Research, 2008, vol. 99, pp. 164-175.
Sohal et al., "Parvalbumin neurons and gamma rhythms enhance cortical circuit performance", Nature, 2009, vol. 459, No. 7247, pp. 698-702.
Yizhar et al., "Optogenetics in neural systems", Neuron Primer, 2011, vol. 71, No. 1, pp. 9-34.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila rhodopsin* cytoplasmic tail domain is required for maintenance of rhabdomere structure." The FASEB Journal, 2007, vol. 21, p. 449-455.
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.

Aravanis, et al. "An optical neural interface: in vivo control of rodent motor cortex with integrated fiberoptic and optogenetic technology," J. Neural. Eng., 2007, vol. 4(3):S143-S156.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Basil et al. "Is There Evidence for Effectiveness of Transcranial Magnetic Stimulation in the Treatment of Psychiatric Disorders?" Psychiatry, 2005, pp. 64-69.
Bebbington et al., The use of vectors based on gene amplification for the expression of cloned genes in mammalian cells in "DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.
Bocquet et al. "A prokaryotic proton-gated ion channel from the nicotinic acetylcholine receptor family." Nature Letters, 2007, vol. 445, p. 116-119.
Boyden, et al. "Millisecond-timescale, genetically targeted optical control of neural activity" Nature Neuroscience, 2005, vol. 8, No. 9: pp. 1263-1268.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology, 1997, vol. 71, No. 9: pp. 6641-6649.
Braun, "Two Light-activated Conductances in the Eye of the Green Alga *Volvox carteri*", 1999, Biophys J., vol. 76, No. 3, pp. 1668-1678.
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cardin, et al. "Driving Fast spiking Cells Induces Gamma Rhythm and Controls Sensory Responses", 2009, Nature, vol. 459, vol. 7247, pp. 663-667.
Cenatiempo "Prokaryotic gene expression in vitro: transcription-translation coupled systems", Biochimie, 1986, vol. 68(4): pp. 505-515.

(56) References Cited

OTHER PUBLICATIONS

Claudio et al. "Nucleotide and deduced amino acid sequences of Torpedo californica acetylcholine receptor gamma subunit." PNAS USA, 1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Crouse, et al. "Expression and amplification of engineered mouse dihydrofolate reductase minigenes" Mol. Cell. Biol., 1983, vol. 3(2): pp. 257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15(4):352-368.
Cucchiaro et al., "Electron-Microsoft Analysis of Synaptic Input from the Perigeniculate Nucleus to A-Lamine of the Lateral Geniculate Nucleus in Cats", The Journal of Comparitive Neurology, 1991, vol. 310, pp. 316-336.
Cui, et al., "Electrochemical deposition and characterization of conducting polymer polypyrrole/PSS on multichannel neural probes," Sensors and Actuators, 2001, vol. 93(1): pp. 8-18.
Date, et al. "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994, vol. 265, pp. 255-258.
Dederen, et al. "Retrograde neuronal tracing with cholera toxin B subunit: comparison of three different visualization methods", Histochemical Journal, 1994, vol. 26, pp. 856-862.
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-365.
Deisseroth et al., "Excitation-neurogenesis Coupling in Adult Neural Stem/Progenitor Cells", 2004, Neuron, vol. 42, pp. 535-552.
Deisseroth "Next-generation optical technologies for illuminating genetically targeted brain circuits," The Journal of Neuroscience, 2006, vol. 26, No. 41, pp. 10380-10386.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 10I, No. 52, pp. 18206-18211.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Eisen, "Treatment of amyotrophic lateral sclerosis", Drugs Aging, 1999; vol. 14, No. 3, pp. 173-196.
Ernst, et al. "Photoactivation of Channelrhodopsin", 2008, vol. 283, No. 3, pp. 1637-1643.

Evanko "Optical excitation yin and yang" Nature Methods, 2007, 4:384.
Esposito et al. "The integrase family of tyrosine recombinases: evolution of a conserved active site domain", Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Genbank Accession No. DQ094781 (Jan. 15, 2008).
Gelvich et al. "Contact flexible microstrip applicators (CFMA) in a range from microwaves up to short waves," IEEE Transactions on Biomedical Engineering, 2002, vol. 49, Issue 9: 1015-1023.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al. "Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat", Neuroscience, 1997, vol. 76, No. 3, pp. 689-706.
Gottesman et al."Bacterial regulation: global regulatory networks," Ann. Rev. Genet., 1984, vol. 18, pp. 415-441.
Gradinaru, et al. "ENpHR: a Natronomonas Halorhodopsin Enhanced for Optogenetic Applications", 2008, Brain Cell Biol., vol. 36 (1-4), pp. 129-139.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol., 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.

(56) References Cited

OTHER PUBLICATIONS

Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation in Vivo of a cloned mammalian gene: cadmium induces the transcription of a mouse metallothionein gene in SV40 vectors," Journal of Molecular Applied Genetics, 1982, vol. 1, No. 4, pp. 273-288.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J., 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane," PNAS, 1993, vol. 90, pp. 3578-3582.
Hirase, et al. "Multiphoton stimulation of neurons", J Neurobiol, 2002, vol. 5I, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hosokawa, T. et al. "Imaging spatio-temporal patterns of long-term potentiation in mouse hippocampus." Philos. Trans. R. Soc. Lond. B., 2003, vol. 358, pp. 689-693.
Hynynen, et al. "Clinical applications of focused ultrasound—The brain." Int. J. Hyperthermia, 2007, vol. 23, No. 2: pp. 193-202.
International Search Report for International Application No. PCT/US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene GAL4 and analysis of its dosage effects on the galactose/melibiose regulon," PNAS, 1982, vol. 79, pp. 6971-6975.
Kandel, E.R., et al. "Electrophysiology of Hippocampal Neurons: I. Sequential Invasion and Synaptic Organization," J Neurophysiol, 1961, vol. 24, pp. 225-242.
Kandel, E.R., et al. "Electrophysiology of Hippocampal Neurons: II. After-Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.

Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khossravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kingston et al. "Transfection of DNA into Eukaryotic Cells," Supplement 63, Current Protocols in Molecular Biology, 1996, 9.1.1-9.1.11, 11 pages.
Kingston et al. "Transfection and Expression of Cloned DNA," Supplement 31, Current Protocols in Immunology, 1999, 10.13.1-10.13.9.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Landy, A. "Mechanistic and structural complexity in the site-specific recombination pathways of Int and FLP", Current Opinion in Genetics and Development, 1993, vol. 3, pp. 699-707.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gone Therapy Can Prevent Neuron Deatch Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992, vol. 9, pp. 861-871.

(56) References Cited

OTHER PUBLICATIONS

Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research, 1996, vol. 24, No. 19: pp. 3784-3789.
Ma et al. "Role of ER Export Signals in Controlling Surface Potassium Channel Numbers," Science, 2001, vol. 291, pp. 316-319.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging, 2001, vol. 24, No. 3, pp. 366-372.
Monje et al., "Irradiation Induces Neural Precursor-Cell Dysfunction", Natural Medicine, 2002, vol. 8, No. 9, pp. 955-962.
Mortensen et al. "Selection of Transfected Mammalian Cells," Supplement 86, Current Protocols in Molecular Biology, 1997, 9.5.1-09.5.19.
Nacher, et al. "NMDA receptor antagonist treatment increases the production of newneurons in the aged rat hippocampus", Neurobiology of Aging, 2003, vol. 24, No. 2: pp. 273-84.
Nagel et al. "Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-1: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nirenberg, et al. "The Light Response of Retinal Ganglion Cells is Truncated by a Displaced Amacrine Circuit", Neuron, 1997, vol. 18: pp. 637-650.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.

Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neural Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Pan et al. "Functional Expression of a Directly Light-Gated Membrane Channel in Mammalian Retinal Neurons: A Potential Strategy for Restoring Light Sensitivity to the Retina After Photoreceptor Degeneration," Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 1 .I-9.1 1 1 .I 8.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured in Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Rathnasingham et al., "Characterization of implantable microfabricated fluid delivery devices," IEEE Transactions on Biomedical Engineering, 2004, vol. 51, No. 1: pp. 138-145.
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.

(56) References Cited

OTHER PUBLICATIONS

Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Salzman, et al. "Cortical microstimulation influences perceptual judgements of motion direction", Nature, 1990, vol. 346, pp. 174-177.
Sajdyk, et al., "Excitatory Amino Acid Receptors in the Basolateral Amygdala Regulate Anxiety Responses in the Social Interaction Test", Brain Research, 1997, vol. 764, pp. 262-264.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008, vol. 33, pp. 368-377.
Sclimenti, et al. "Directed evolution of a recombinase for improved genomic integration at a native human sequence," Nucleic Acids Research, 2001, vol. 29, No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.
Silver, et al. "Amino terminus of the yeast GAL4 gene product is sufficient for nuclear localization" PNAS, 1984, vol. 81, No. 19: pp. 5951-5955.
Singer et al. "Elevated Intrasynaptic Dopamine Release in Tourette's Syndrome Measured by PET," American Journal of Psychiatry, 2002, vol. 159: pp. 1329-1336.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.

Takahashi, et al. "Diversion of the Sign of Phototaxis in a *Chlamydomonas reinhardtii* Mutant Incorporated with Retinal and Its Analogs," FEBS Letters, 1992, vol. 314, No. 3, pp. 275-279.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human $Ca_v 2.1$ Current Density in Neurons", PNAS USA, 2002, vol. 99, No. 20: pp. 13284-13289.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
[No Authors Listed] "Two bright new faces in gene therapy," Nature Biotechnology, 1996, vol. 14: p. 556.
Tye et. al., "Amygdala circuitry mediating reversible and bidirectional control of anxiety", Nature, 2011, vol. 471(7338): pp. 358-362.
Tye et. al., Supplementary Materials: "An optically-resolved microcircuit for bidirectional anxiety control", Nature, 2011, vol. 471(7338): pp. 358-362.
Tye, et al. "Optogenetic investigation of neural circuits underlying brain disease in animal models," Nature Reviews Neuroscience (Mar. 2012), 13(4):251-266.
"SubName: Full=Channelrhodopsin-1", retrieved from EBI accession No. UNIPROT: B4Y103. Database accession No. B4Y103. Sep. 23, 2008.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.1-19.39.
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Wang et al. "Direct-current Nanogenerator Driven By Ultrasonic Waves," Science, 2007, vol. 316, pp. 102-105.
Wang et. al., "High-speed mapping of synaptic connectivity using photostimulation in Channelrhodopsin-2 transgenic mice", PNAS, 2007, vol. 104, No. 19, pp. 8143-8148.
Weick et al. "Interactions with PDZ Proteins are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Witten et. al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.

(56) References Cited

OTHER PUBLICATIONS

Yan et al., "Cloning and Characterization of a Human β, β-Carotene-15, 15'-Dioxygenase that is Highly Expressed in the Retinal Pigment Epithelium", Genomics, 2001, vol. 72: pp. 193-202.
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Channelrhodopsin-2 and optical control of excitable cells," Nature Methods, 2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008, vol. 11, No. 6, pp. 631-633.
Zhang "Multimodal fast optical interrogation of neural circuitry," Nature, 2007, vol. 446, pp. 633-641.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient in Vivo Gene Delivery", Journal of Virology, 1998, vol. 72, No. 12, pp. 9873-9880.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Asano, et al.; "Optically Controlled Contraction of Photosensitive Skeletal Muscle Cells"; Biotechnology & Bioengineering; vol. 109, No. 1, pp. 199-204 (Jan. 2012).
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
Genbank Accession No. BAA09452.1; Mukohata et al.; pp. 1 (Feb. 10, 1999).
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Mueller, et al.; "Clinical Gene Therapy Using Recombinant Adeno-Associated Virus Vectors"; Gene Therapy; vol. 15, pp. 858-863 (2008).
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Berndt et al., "Structure-Guided Transformation of Channelrhodopsin into a Light-Activated Chloride Channel", Science (Apr. 2014), 344(6182):420-424.
Chow et al., "Optogenetics and Translational Medicine", Science Translational Medicine (Mar. 2013), 5(177):177ps5.
Eijkelkamp, et al. "Neurological perspectives on voltage-gated sodium channels", Brain (Sep. 2012), 135(Pt 9):2585-2612.
Garrido et al., "A targeting motif involved in sodium channel clustering at the axonal initial segment", Science (Jun. 2003), 300(5628):2091-4.
Han; et al., "Two-color, bi-directional optical voltage control of genetically-targeted neurons", CoSyne (2007), Abstract Presentation, Poster III-67, p. 269, Presented Feb. 24, 2007.
Hustler; et al., "Acetylcholinesterase staining in human auditory and language cortices: regional variation of structural features", Cereb Cortex (Mar.-Apr. 1996), 6(2):260-70.
Iyer et al., "Virally mediated optogenetic excitation and inhibition of pain in freely moving nontransgenic mice", Nat Biotechnol., (Mar. 2014), 32(3):274-8.
Ji et al., "Light-evoked Somatosensory Perception of Transgenic Rats that Express Channelrhodopsin-2 in Dorsal Root Ganglion Cells", PLoS One (2012), 7(3):e32699.
Jennings et al., "Distinct extended amygdala circuits for divergent motivational states," Nature (Apr. 2013), 496(7444):224-8.
Kim et al., "PDZ domain proteins of synapses", Nature Reviews Neuroscience, (Oct. 2004), 5(10):771-81.
Kim et al., "Diverging neural pathways assemble a behavioural state from separable features in anxiety" Nature (Apr. 2013), 496(7444):219-23.
Kokel et al., "Photochemical activation of TRPA1 channels in neurons and animals", Nat Chem Biol (Apr. 2013), 9(4):257-63.
Lammel et al., "Input-specific control of reward and aversion in the ventral tegmental area", Nature (Nov. 2012), 491(7423): 212-7.
Liske et al., "Optical inhibition of motor nerve and muscle activity in vivo", Muscle Nerve (Jun. 2013), 47(6):916-21.
Llewellyn et al., "Orderly recruitment of motor units under optical control in vivo", Nature Medicine, (Oct. 2010), 16(10):1161-5.
Mattis et al., "Principles for applying optogenetic tools derived from direct comparative analysis of microbial opsins", Nat Methods (Dec. 2011), 9(2):159-72.
Mourot et al., "Rapid Optical Control of Nociception with an Ion Channel Photoswitch", Nat Methods (Feb. 2012), 9(4):396-402.
Nieh et al., "Optogenetic dissection of neural circuits underlying emotional valence and motivated behaviors", Brain Research, (May 2012), 1511:73-92.
Slamovits et al., "A bacterial proteorhodopsin proton pump in marie eukaryotes", Nature Communications (Feb. 2011), 2:183.
Towne et al., "Efficient transduction of non-human primate motor neurons after intramuscular delivery of recombinant AAV serotype 6", Gene Ther. (Jan. 2010), 17(1):141-6.
Towne et al., "Optogenetic control of targeted peripheral axons in freely moving animals", PLoS One (Aug. 2013), 8(8):e72691.
Towne et al., "Recombinant adeno-associated virus serotype 6 (rAAV2/6)-mediated gene transfer to nociceptive neurons through different routes of delivery", Mol Pain (Sep. 2009), 5:52.
Wang et al., "Mrgprd-Expressing Polymodal Nociceptive Neurons Innervate Most Known Classes of Substantia Gelatinosa Neurons", J Neurosci (Oct. 2009), 29(42):13202-13209.
Williams et al., "From optogenetic technologies to neuromodulation therapies", Sci Transl Med. (Mar. 2013), 5(177):177ps6.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Definition of Psychosis (2015).
Ebert et al., "A Moloney MLV-rat somatotropin fusion gene produces biologically active somatotropin in a transgenic pig", Mol. Endocrinology, 1988, vol. 2, pp. 277-283.
Hammer et al., "Spontaneous inflammatory disease in transgenic rats expressing HLA-B27 and Human $β_2$m: an animal model of HLA-B27-associated human disorders", Cell, 1990, vol. 63, pp. 1099-1112.

(56) References Cited

OTHER PUBLICATIONS

Karra, et al. "Transfection Techniques for Neuronal Cells", The Journal of Neuroscience, 2010, vol. 30, No. 18, pp. 6171-6177.
Kelder et al., "Glycoconjugates in human and transgenic animal milk", Advances in Exp. Med. and Biol., 2001, vol. 501, pp. 269-278.
Mullins et al., "Fulminant hypertension in transgenic rats harbouring the mouse Ren-2 gene", Nature, 1990, vol. 344, pp. 541-544.
Mullins et al., "Expression of the DBA/2J Ren-2 gene in the adrenal gland of transgenic mice", EMBO, 1989, vol. 8, pp. 4065-4072.
Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.
Written opinion of PCT Application No. PCT/US2011/059383 (dated May 9, 2012).
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Takahashi, et al., "Induction of Pluripotent Stem Cells from Mouse Embryonic and Adult Fibroblast Cultures by Defined Factors", 2006, Cell, vol. 126, pp. 663-676.
Babin et al., "Zebrafish Models of Human Motor Neuron Diseases: Advantages and Limitations", Progress in Neurobiology (2014), 118:36-58.
Santana et al., "Can Zebrafish Be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.
Suzuki et al., "Stable Transgene Expression from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Cazillis et al., "VIP and PACAP induce selective neuronal differentiation of mouse embryonic stem cells", Eur J Neurosci, 2004, 19(4):798-808.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Brewin; "The Nature and Significance of Memory Disturbance in Posttraumatic Stress Disorder"; Ann. Rev. Clin. Psychol.; vol. 7, pp. 203-227 (2011).
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Samuelson; "Post-traumatic stress disorder and declarative memory functioning: a review"; Dialogues in Clinical Neuroscience; vol. 13, No. 3, pp. 346-351 (2011).
Lanyi et al. "The primary structure of a Halorhodopsin from *Natronobacterium pharaonis*" Journal of Biological Chemistry, 1990, vol. 265, No. 3, p. 1253-1260.
Hofherr et al. "Selective Golgi export of Kir2.1 controls the stoichiometry of functional Kir2.x channel heteromers", Journal of Cell Science, 2005, vol. 118, No. 9, p. 1935-1943.
Loetterle, et al., "Cerebellar Stimulation: Pacing the Brain", American Journal of Nursing, 1975, vol. 75, No. 6, pp. 958-960.

Takahashi, et al., "Induction of Pluripotent Stem Cells from Mouse Embryonic and Adult Fibroblast Cultures by Defined Factors", 2006, Cell, vol. 126, p. 958-960.
Gradinaru, et al., Molecular and Cellular Approaches for Diversifying and Extending Optogenetics, Cell, 2010, vol. 141, No. 1, pp. 154-165.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"N. pharaonis halorhodopsin (hop) gene, complete cds.", XP002704883, retrieved from EBI accession No. EMBL: J05199. Database accession No. J05199. Nov. 22, 1990.
"Subname: Fluu=Bacteriorhodopsin"; XP002704863, retrieved from EBI accession No. UNIPROT: BOR5N9. Database accession No. BOR5N9. Apr. 8, 2008.
Zhang, et al., "The Microbial Opsin Family of Optogenetic Tools", Cell, 2011, vol. 147, No. 7, pp. 1146-1457.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
Fiala et al., "Optogenetic approaches in neuroscience", Current Biology, Oct. 2010, 20(20):R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amygdala", Neurobiol Learning Mem, 2007, 87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in *Drosophila larvae*", Current Biology, Sep. 2006, 16(17):1741-1747.
Davis; "The many faces of epidermal growth factor repeats," The New Biologist; vol. 2, No. 5, pp. 410-419 (1990).
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
EBI accession No. UNIPROT: A7U0Y6; "SubName: Full=Bacteriorhodopsin"; (Aug. 10, 2010).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
Kaiser; "Clinical research. Death prompts a review of gene therapy vector"; Science; 317(5838):580 (Aug. 3, 2007).
Kay; "State-of-the-art gene-based therapies: the road ahead"; Nature Reviews Genetics; vol. 12, pp. 316-328 (May 2011).
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).

(56) References Cited

OTHER PUBLICATIONS

Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Fox et al., "A gene neuron expression fingerprint of C. elegans embryonic motor neurons", BMC Genomics, 2005, 6(42):1-23.
Nonet, "Visualization of synaptic specializations in live C. elegans with synaptic vesicle protein-GFP fusions", J. Neurosci. Methods, 1999, 89:33-40.
Synapse, Chapter 13, http://michaeldmann.net/mann13.html, downloaded Apr. 2014.
Gradinaru et al., "Targeting and readout strategies for fast optical neural control in vitro and in vivo", J Neuroscience, 2007, 27(52):14231-14238.
U.S. Appl. No. 13/555,981, filed Jul. 23, 2012, Deisseroth et al.
U.S. Appl. No. 13/662,809, filed Sep. 19, 2012, Deisseroth et al.
U.S. Appl. No. 13/623,612, filed Sep. 20, 2012, Deisseroth et al.
U.S. Appl. No. 13/718,243, filed Dec. 18, 2012, Deisseroth et al.
U.S. Appl. No. 13/763,119, filed Feb. 8, 2013, Deisseroth et al.
U.S. Appl. No. 13/763,132, filed Feb. 8, 2013, Deisseroth et al.
U.S. Appl. No. 13/772,732, filed Feb. 21, 2013, Deisseroth et al.
U.S. Appl. No. 13/847,653, filed Mar. 20, 2013, Deisseroth et al.
U.S. Appl. No. 13/847,785, filed Mar. 20, 2013, Deisseroth et al.
U.S. Appl. No. 13/849,913, filed Mar. 25, 2013, Deisseroth et al.
U.S. Appl. No. 13/850,426, filed Mar. 26, 2013, Deisseroth et al.
U.S. Appl. No. 13/850,428, filed Mar. 26, 2013, Deisseroth et al.
U.S. Appl. No. 13/850,436, filed Mar. 26, 2013, Deisseroth et al.
U.S. Appl. No. 13/850,709, filed Mar. 26, 2013, Deisseroth et al.
U.S. Appl. No. 13/854,750, filed Apr. 1, 2013, Deisseroth et al.
U.S. Appl. No. 13/854,754, filed Apr. 1, 2013, Deisseroth et al.
U.S. Appl. No. 13/855,413, filed Apr. 2, 2013, Deisseroth et al.
U.S. Appl. No. 13/875,966, filed May 2, 2013, Deisseroth et al.
U.S. Appl. No. 13/882,566, filed Nov. 4, 2011, Deisseroth et al.
U.S. Appl. No. 13/882,666, filed Nov. 4, 2011, Deisseroth et al.
U.S. Appl. No. 13/882,703, filed Nov. 4, 2011, Deisseroth et al.
U.S. Appl. No. 13/882,705, filed Nov. 4, 2011, Deisseroth et al.
U.S. Appl. No. 13/882,719, filed Nov. 4, 2011, Deisseroth et al.
Han, et al., "Millisecond-Timescale Optical Control of Neural Dynamics in the Nonhuman Primate Brain"; Neuron; vol. 62, pp. 191-198 (Apr. 30, 2009).
Han, et a.; "Virogenetic and optogenetic mechanisms to define potential therapeutic targets in psychiatric disorders"; Neuropharmacology; vol. 62, pp. 89-100 (2012).
Zhang, et al., "Optogenetic interrogation of neural circuits: Technology for probing mammalian brain structures"; Nature Protocols; vol. 5, No. 3, pp. 439-456 (Mar. 1, 2010).
Li et al., "Surface Expression of Kv1 Channels is Governed by a C-Terminal Motif", J. Bioi. Chem. (2000), 275(16):11597-11602.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Deisseroth, et al., "Controlling the Brain with Light", Scientific American, 2010, vol. 303, pp. 48-55.
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Sineshchekov, et al., "Two Rhodopsins Mediate Phototaxis to Low and High Intensity Light in Chlamydomas Reinhardtil", PNAS, 2002, vol. 99, No. 13, pp. 8689-8694.
Tønnese, et al., "Optogenetic Control of Epileptiform Activity", PNAS, 2009, vol. 106, No. 29, pp. 12162-12167.
Xiong et al., "Interregional connectivity to primary motor cortex revealed using MRI resting state images", Hum Brain Mapp, 1999, 8(2-3):151-156.

Arenkiel, et al. "In vivo light-induced activation of neural circuitry in transgenic mice expressing Channelrhodopsin-2", Neuron, 2007, 54:205-218.
Milella et al. "Opposite roles of dopamine and orexin in quinpirole-induced excessive drinking: a rat model of psychotic polydipsia'" Psychopharmacology, 2010, 211:355-366.
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Hikida et al., "Increased sensitivity to cocaine by cholinergic cell ablation in nucleus accumbens", PNAS, Nov. 2001, 98(23):13351-13354.
Hikida et al., "Acetylcholine enhancement in the nucleus accumbens prevents addictive behavior of cocaine and morphine", PNAS, May 2003, 100(10):6169-6173.
Kitabatake et al., "Impairment of reward-related learning by cholinergic cell ablation in the striatum," PNAS, Jun. 2003, 100(13):7965-7970.
Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004 (Dec. 2004), pp. 750-769.
Tam, B. et al., "Identification of an Outer Segment Targeting Signal in the COOH Terminus of Rhodopsin Using Transgenic Xenopus laevis", The Journal of Cell Biology, 2000, vol. 151, No. 7, pp. 1369-1380.
Balint, et al., "The Nitrate Transporting Photochemical Reaction Cycle of the Pharaonis Halorhodopsin", Biophysical Journal, 2004, vol. 86, pp. 1655-1663.
Clark, et al.; "A future for transgenic livestock"; Nature Reviews Genetics; vol. 4, No. 10, pp. 825-833 (Oct. 2003).
Do Carmo, et al.; "Modeling Alzheimer's disease in transgenic rats"; Molecular Neurodegeneration; vol. 8, No. 37, 11 pages (2013).
Heymann, et al.; "Expression of Bacteriorhodopsin in Sf9 and COS-1 Cells"; Journal of Bioenergetics and Biomembranes; vol. 29, No. 1, pp. 55-59 (1997).
Ramalho, et al.; "Mouse genetic corneal disease resulting from transgenic insertional mutagenesis"; Br. J. Ophthalmol.; vol. 88, No. 3, pp. 428-432 (Mar. 2004).
Ristevski; "Making Better Transgenic Models: Conditional, Temporal, and Spatial Approaches"; Molecular Biotechnology; vol. 29, No. 2, pp. 153-163 (Feb. 2005).
Sigmund; "Viewpoint: Are Studies in Genetically Altered Mice Out of Control?"; Arterioscler Thromb Vasc. Biol.; vol. 20, No. 6, pp. 1425-1429 (Jun. 2000).
Sineshchekov et al.; "Intramolecular Proton Transfer in Channelrhodopsins"; Biophysical Journal; vol. 104, No. 4, pp. 807-807 (Feb. 2013).
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Jones, et al.; "Animal Models of Schizophrenia"; British Journal of Pharmacology; vol. 164, pp. 1162-1194 (2011).
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Day, et al.; "The Nucleus Accumbens and Pavlovian Reward Learning"; Neuroscientist; vol. 13, No. 2, pp. 148-159 (Apr. 2007).
Knopfel, et al.; "A comprehensive concept of optogenetics"; Progress in Brain Research; vol. 196, pp. 1-28 (2012).
Packer, et al.; "Targeting Neurons and Photons for Optogenetics"; Nature Neuroscience; vol. 16, No. 7, pp. 805-815 (Jul. 2013).
Airan, et al.; "Integration of light-controlled neuronal firing and fast circuit imaging"; Current Opinion in Neurobiology; vol. 17, pp. 587-592 (2007).

(56) References Cited

OTHER PUBLICATIONS

Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Bowers, et al.; "Genetic therapy for the nervous system"; Human Molecular Genetics; vol. 20, No. 1, pp. R28-R41 (2011).
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
GenBank Accession No. AC096118.6; Rattus norvegicus clone CH230-11 B15, 1-4, 24-25, Working Draft Sequence, 3 unordered pieces. May 10, 2003.
GenBank Accession No. U79717.1; Rattus norvegicus dopamine 02 receptor 1-4, 24-25 gene, promoter region and exon 1. Jan. 31, 1997.
Haim, et al.; "Gene Therapy to the Nervous System"; Stem Cell and Gene-Based Therapy; Section 2, pp. 133-154 (2006).
Pandya, et al.; "Where in the Brain Is Depression?"; Curr. Psychiatry Rep.; vol. 14, pp. 634-642 (2012).
Stonehouse, et al.; "Caffeine Regulates Neuronal Expression of the Dopamine 2 Receptor Gene"; Molecular Pharmacology; vol. 64, No. 6, pp. 1463-1473 (2003).

Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Davidson, et al.; "Viral Vectors for Gene Delivery to the Nervous System"; Nature Reviews Neuroscience; vol. 4, pp. 353-364 (May 2003).
Definition of integral. Merriam-Webster Dictionary, retrieved on Mar. 20, 2017; Retrieved from the internet: <http://www.merriam-webster.com/dictionary/integral>.
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology", Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Ferenczi, et al.; "Optogenetic approaches addressing extracellular modulation of neural excitability"; Scientific Reports; vol. 6, 20 pages (Apr. 5, 2016).
Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Definition of Implant; Merriam-Webster Dictionary; retrieved Nov. 7, 2016 (http://www.merriam-webster.com/dictionary/implant).
Berke, et al. "Addiction, Dopamine, and the Molecular Mechanisms of Memory", Molecular Plasticity, 2000, vol. 25: pp. 515-532.

(56) References Cited

OTHER PUBLICATIONS

Goshen et al. "Dynamics of Retrieval Strategies for Remote Memories", Cell, 2011, vol. 147: pp. 678-589.
Jimenez S.A & Maren S. et al/ "Nuclear disconnection within the amygdala reveals a direct pathway to fear", Learning Memory, 2009, vol. 16: pp. 766-768.
Ehrlich I. et al. "Amygdala inhibitory circuits and the control of fear memory", Neuron, 2009. Friedrich Meischer Institute, vol. 62: pp. 757-771.
Berndt et al. "Bi-stable neural state switches", Nature Neuroscience, 2009, vol. 12, No. 2: pp. 229-234.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Tsuchida; "Nervous Control of Micturition"; The Japanese Journal of Urology; vol. 80, No. 9, pp. 1257-1277 (1989).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Bibel, et al.; "Differentiation of mouse embryonic stem cells into a defined neuronal lineage"; Nature Neuroscience; vol. 7, No. 9, pp. 1033-1009 (Sep. 2004).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).
Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Boyden, et al.; "A history of optogenetics: the development of tools for controlling brain circuits with light"; F1000 Biology Reports; vol. 3, No. 11, 12 pages. (May 3, 2011).
Knox, et al.; "Heterologous Expression of Limulus Rhodopsin"; The Journal of Biological Chemistry; vol. 278, No. 42, pp. 40493-40502 (Oct. 17, 2003).
Lin, et al.; "Characterization of Engineered Channelrhodopsin Variants with Improved Properties and Kinetics"; Biophysical Journal; vol. 96, No. 5, pp. 1803-1814 (Mar. 2009).

\* cited by examiner

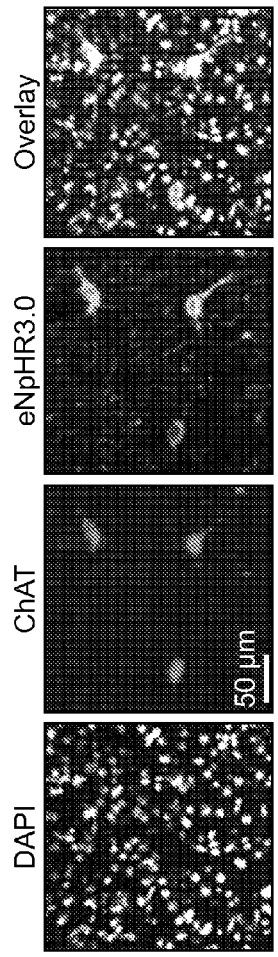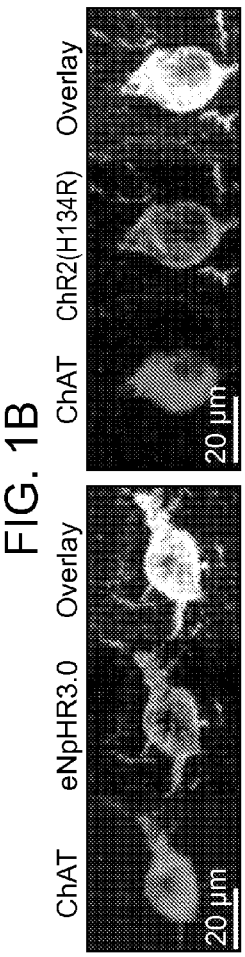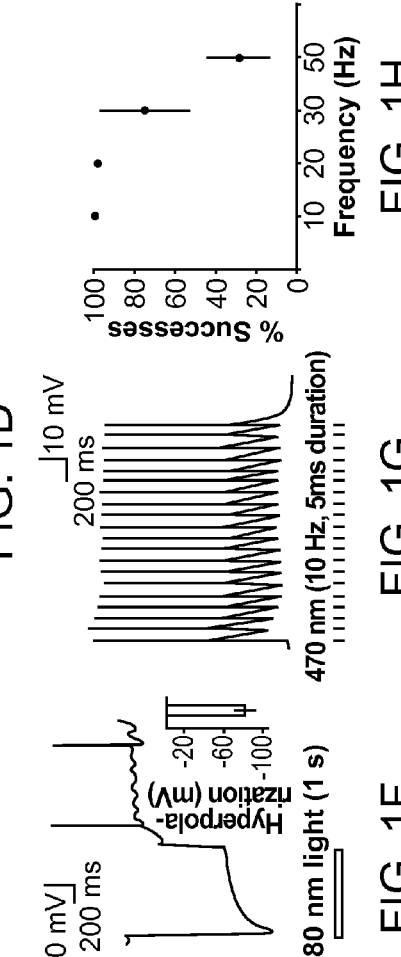

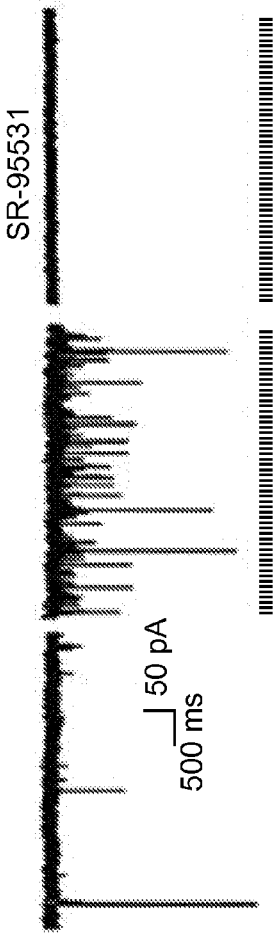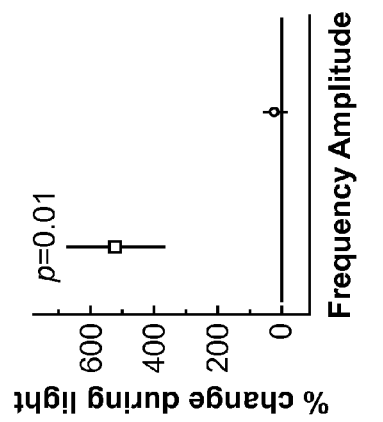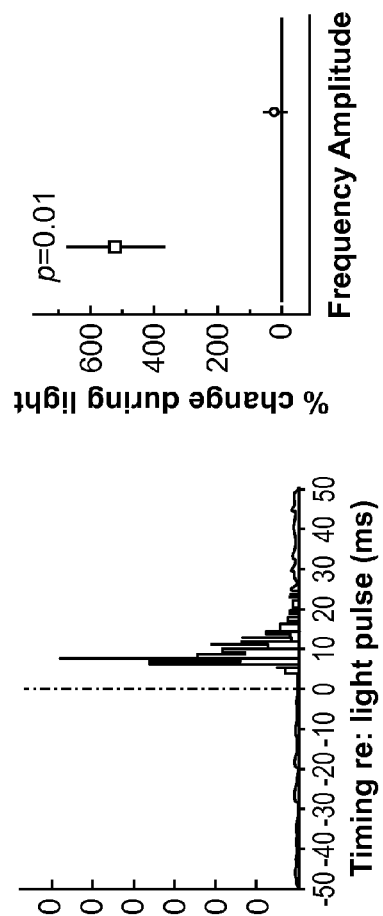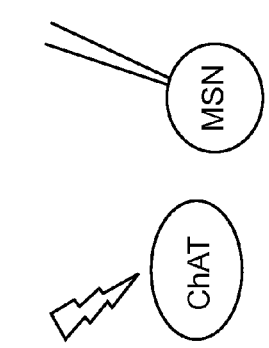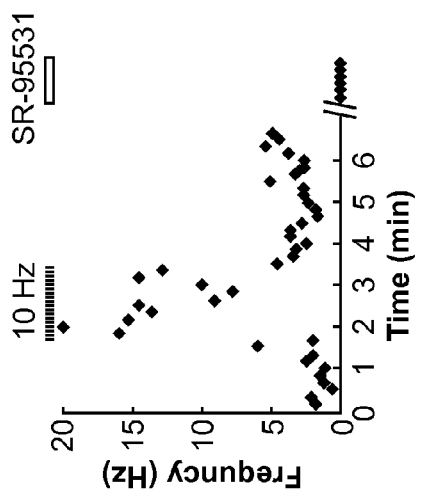
FIG. 2B
FIG. 2E
FIG. 2D
FIG. 2A
FIG. 2C

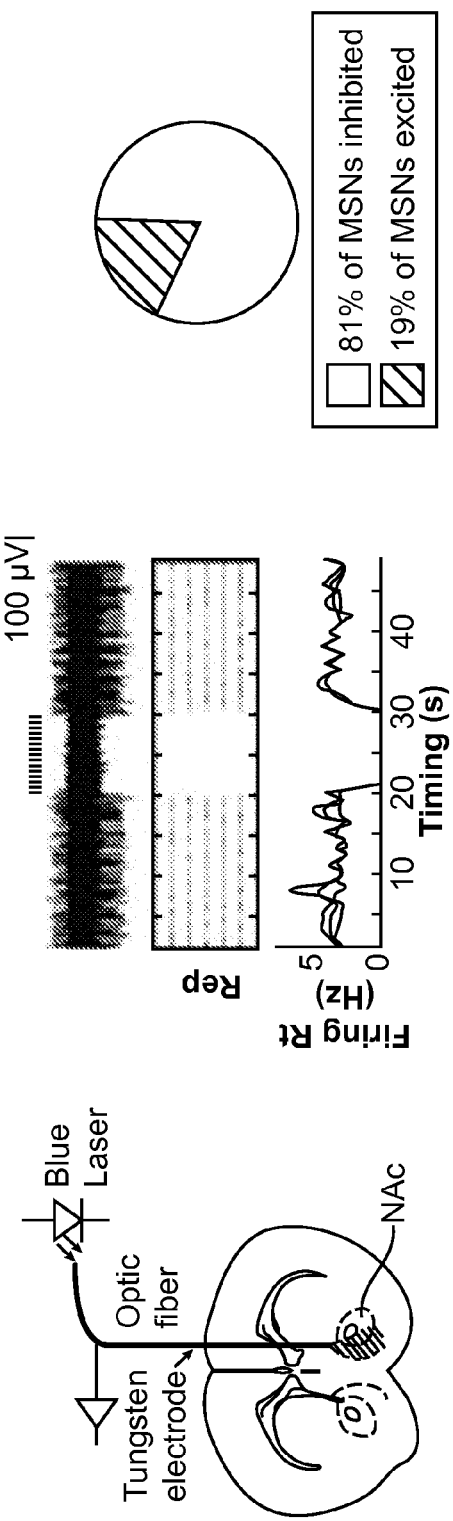
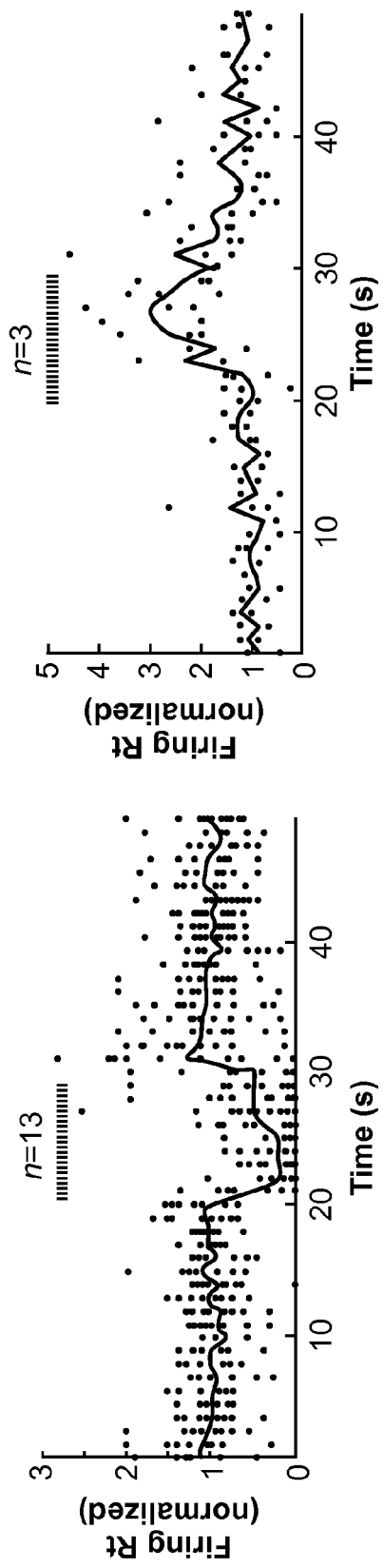
FIG. 2F
FIG. 2G
FIG. 2H
FIG. 2I

76% of sites excited
24% of sites inhibited

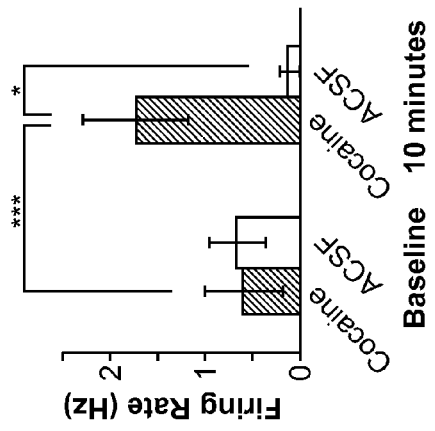
FIG. 4A
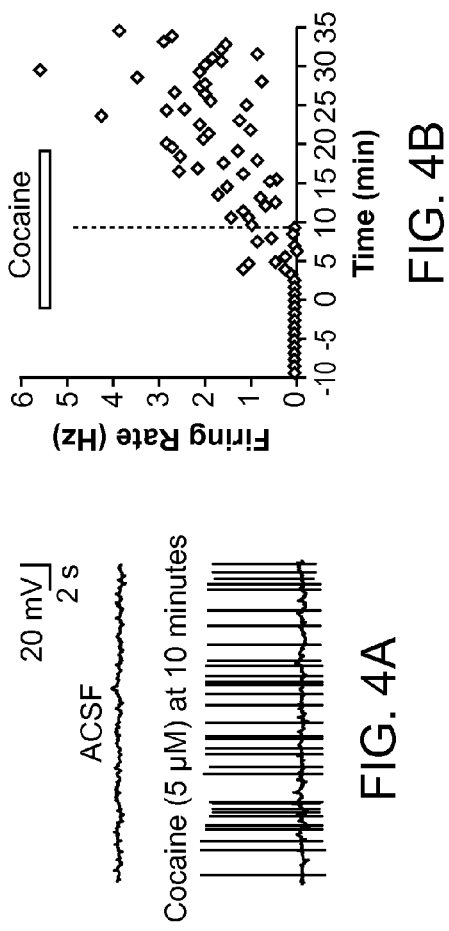
FIG. 4B
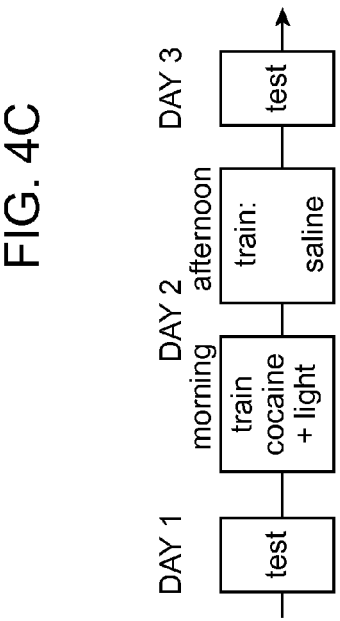
FIG. 4C
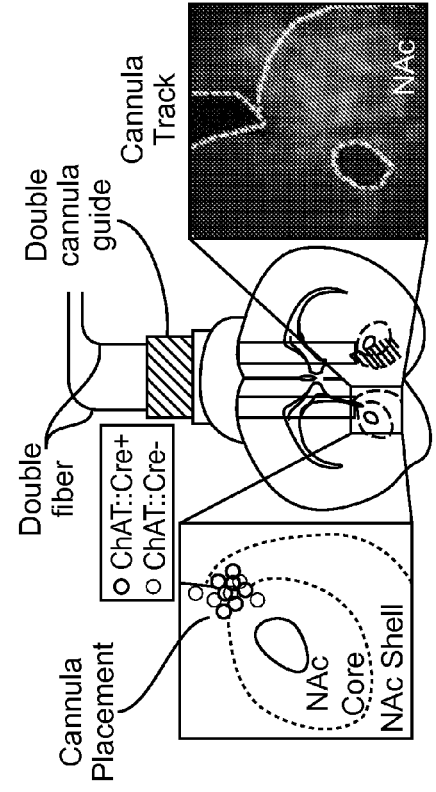
FIG. 4D
FIG. 4E

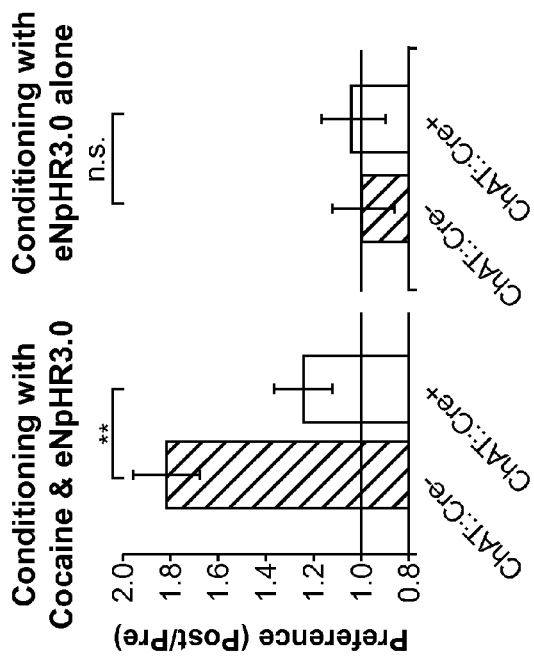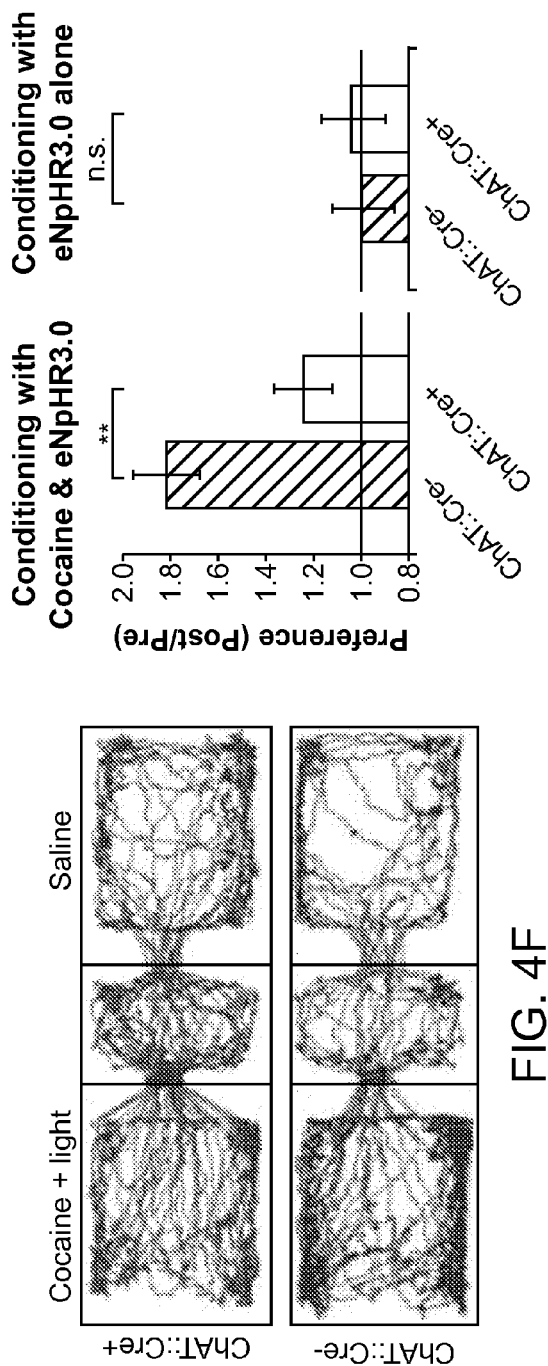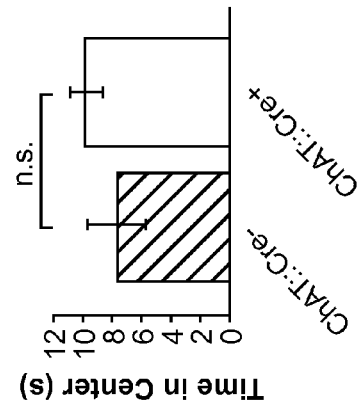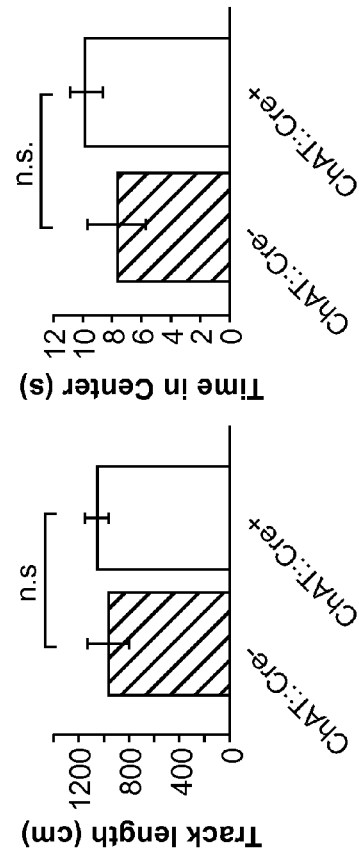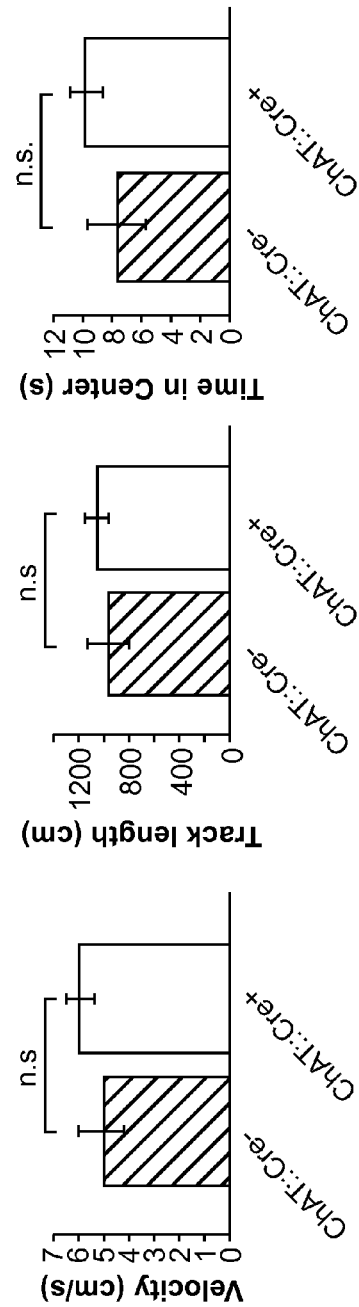
FIG. 4F
FIG. 4G
FIG. 4H
FIG. 4I
FIG. 4J

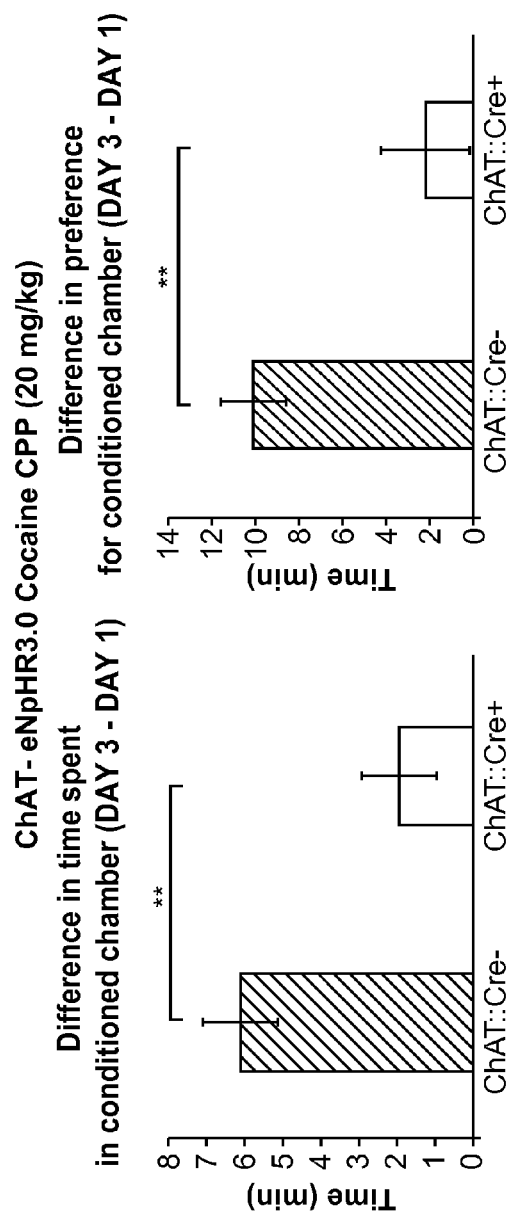
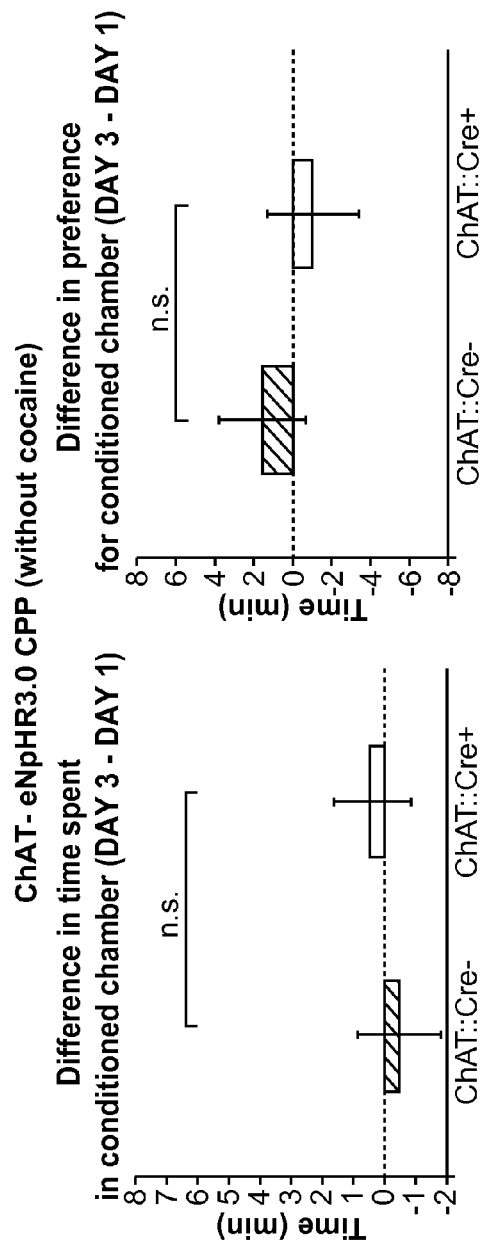
FIG. 6A
FIG. 6B

SEQUENCE LISTING

<160> NUMBER OF SEQ ID NOS: 15

<210> SEQ ID NO 1
<211> LENGTH: 273
<212> TYPE: PRT
<213> ORGANISM: Natronomonas pharaonis

<400> SEQUENCE: 1

```
Val Thr Gln Arg Glu Leu Phe Glu Phe Val Leu Asn Asp Pro Leu Leu
 1               5                  10                  15

Ala Ser Ser Leu Tyr Ile Asn Ile Ala Leu Ala Gly Leu Ser Ile Leu
                20                  25                  30

Leu Phe Val Phe Met Thr Arg Gly Leu Asp Asp Pro Arg Ala Lys Leu
            35                  40                  45

Ile Ala Val Ser Thr Ile Leu Val Pro Val Val Ser Ile Ala Ser Tyr
        50                  55                  60

Thr Gly Leu Ala Ser Gly Leu Thr Ile Ser Val Leu Glu Met Pro Ala
65                  70                  75                  80

Gly His Phe Ala Glu Gly Ser Ser Val Met Leu Gly Gly Glu Glu Val
                85                  90                  95

Asp Gly Val Val Thr Met Trp Gly Arg Tyr Leu Thr Trp Ala Leu Ser
            100                 105                 110

Thr Pro Met Ile Leu Leu Ala Leu Gly Leu Leu Ala Gly Ser Asn Ala
        115                 120                 125

Thr Lys Leu Phe Thr Ala Ile Thr Phe Asp Ile Ala Met Cys Val Thr
    130                 135                 140

Gly Leu Ala Ala Ala Leu Thr Thr Ser Ser His Leu Met Arg Trp Phe
```

```
                 145                 150                 155                 160
        Trp Tyr Ala Ile Ser Cys Ala Cys Phe Leu Val Val Leu Tyr Ile Leu
                        165                 170                 175

Leu Val Glu Trp Ala Gln Asp Ala Lys Ala Ala Gly Thr Ala Asp Met
                        180                 185                 190

Phe Asn Thr Leu Lys Leu Leu Thr Val Val Met Trp Leu Gly Tyr Pro
                        195                 200                 205

Ile Val Trp Ala Leu Gly Val Glu Gly Ile Ala Val Leu Pro Val Gly
                        210                 215                 220

Val Thr Ser Trp Gly Tyr Ser Phe Leu Asp Ile Val Ala Lys Tyr Ile
        225                 230                 235                 240

Phe Ala Phe Leu Leu Leu Asn Tyr Leu Thr Ser Asn Glu Ser Val Val
                        245                 250                 255

Ser Gly Ser Ile Leu Asp Val Pro Ser Ala Ser Gly Thr Pro Ala Asp
                        260                 265                 270

Asp

<210> SEQ ID NO 2
<211> LENGTH: 559
<212> TYPE: PRT
<213> ORGANISM: Artificial Sequence
<220> FEATURE:
<223> OTHER INFORMATION: Synthetic polypeptide

<400> SEQUENCE: 2

Met Thr Glu Thr Leu Pro Pro Val Thr Glu Ser Ala Val Ala Leu Gln
        1               5                   10                  15

Ala Glu Val Thr Gln Arg Glu Leu Phe Glu Phe Val Leu Asn Asp Pro
                        20                  25                  30

Leu Leu Ala Ser Ser Leu Tyr Ile Asn Ile Ala Leu Ala Gly Leu Ser
                        35                  40                  45

Ile Leu Leu Phe Val Phe Met Thr Arg Gly Leu Asp Asp Pro Arg Ala
                        50                  55                  60

Lys Leu Ile Ala Val Ser Thr Ile Leu Val Pro Val Val Ser Ile Ala
        65                  70                  75                  80

Ser Tyr Thr Gly Leu Ala Ser Gly Leu Thr Ile Ser Val Leu Glu Met
                        85                  90                  95

Pro Ala Gly His Phe Ala Glu Gly Ser Ser Val Met Leu Gly Gly Glu
                        100                 105                 110

Glu Val Asp Gly Val Val Thr Met Trp Gly Arg Tyr Leu Thr Trp Ala
                        115                 120                 125

Leu Ser Thr Pro Met Ile Leu Leu Ala Leu Gly Leu Leu Ala Gly Ser
                        130                 135                 140

Asn Ala Thr Lys Leu Phe Thr Ala Ile Thr Phe Asp Ile Ala Met Cys
        145                 150                 155                 160

Val Thr Gly Leu Ala Ala Ala Leu Thr Thr Ser Ser His Leu Met Arg
                        165                 170                 175

Trp Phe Trp Tyr Ala Ile Ser Cys Ala Cys Phe Leu Val Val Leu Tyr
                        180                 185                 190

Ile Leu Leu Val Glu Trp Ala Gln Asp Ala Lys Ala Ala Gly Thr Ala
                        195                 200                 205

Asp Met Phe Asn Thr Leu Lys Leu Leu Thr Val Val Met Trp Leu Gly
                        210                 215                 220

Tyr Pro Ile Val Trp Ala Leu Gly Val Glu Gly Ile Ala Val Leu Pro
        225                 230                 235                 240
```

Val Gly Val Thr Ser Trp Gly Tyr Ser Phe Leu Asp Ile Val Ala Lys
            245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
            275                 280                 285

Ala Asp Asp Ala Ala Ala Lys Ser Arg Ile Thr Ser Glu Gly Glu Tyr
290                 295                 300

Ile Pro Leu Asp Gln Ile Asp Ile Asn Val Val Ser Lys Gly Glu Glu
305                 310                 315                 320

Leu Phe Thr Gly Val Val Pro Ile Leu Val Glu Leu Asp Gly Asp Val
            325                 330                 335

Asn Gly His Lys Phe Ser Val Ser Gly Glu Gly Glu Gly Asp Ala Thr
            340                 345                 350

Tyr Gly Lys Leu Thr Leu Lys Phe Ile Cys Thr Thr Gly Lys Leu Pro
            355                 360                 365

Val Pro Trp Pro Thr Leu Val Thr Thr Phe Gly Tyr Gly Leu Gln Cys
            370                 375                 380

Phe Ala Arg Tyr Pro Asp His Met Lys Gln His Asp Phe Phe Lys Ser
385                 390                 395                 400

Ala Met Pro Glu Gly Tyr Val Gln Glu Arg Thr Ile Phe Phe Lys Asp
            405                 410                 415

Asp Gly Asn Tyr Lys Thr Arg Ala Glu Val Lys Phe Glu Gly Asp Thr
            420                 425                 430

Leu Val Asn Arg Ile Glu Leu Lys Gly Ile Asp Phe Lys Glu Asp Gly
            435                 440                 445

Asn Ile Leu Gly His Lys Leu Glu Tyr Asn Tyr Asn Ser His Asn Val
450                 455                 460

Tyr Ile Met Ala Asp Lys Gln Lys Asn Gly Ile Lys Val Asn Phe Lys
465                 470                 475                 480

Ile Arg His Asn Ile Glu Asp Gly Ser Val Gln Leu Ala Asp His Tyr
            485                 490                 495

Gln Gln Asn Thr Pro Ile Gly Asp Gly Pro Val Leu Leu Pro Asp Asn
            500                 505                 510

His Tyr Leu Ser Tyr Gln Ser Ala Leu Ser Lys Asp Pro Asn Glu Lys
            515                 520                 525

Arg Asp His Met Val Leu Leu Glu Phe Val Thr Ala Ala Gly Ile Thr
            530                 535                 540

Leu Gly Met Asp Glu Leu Tyr Lys Phe Cys Tyr Glu Asn Glu Val
545                 550                 555

<210> SEQ ID NO 3
<211> LENGTH: 542
<212> TYPE: PRT
<213> ORGANISM: Artificial Sequence
<220> FEATURE:
<223> OTHER INFORMATION: Synthetic polypeptide

<400> SEQUENCE: 3

Met Val Thr Gln Arg Glu Leu Phe Glu Phe Val Leu Asn Asp Pro Leu
1               5                   10                  15

Leu Ala Ser Ser Leu Tyr Ile Asn Ile Ala Leu Ala Gly Leu Ser Ile
            20                  25                  30

Leu Leu Phe Val Phe Met Thr Arg Gly Leu Asp Asp Pro Arg Ala Lys
        35                  40                  45

```
Leu Ile Ala Val Ser Thr Ile Leu Val Pro Val Ser Ile Ala Ser
 50                  55                  60

Tyr Thr Gly Leu Ala Ser Gly Leu Thr Ile Ser Val Leu Glu Met Pro
 65                  70                  75                  80

Ala Gly His Phe Ala Glu Gly Ser Ser Val Met Leu Gly Gly Glu Glu
                     85                  90                  95

Val Asp Gly Val Val Thr Met Trp Gly Arg Tyr Leu Thr Trp Ala Leu
                100                 105                 110

Ser Thr Pro Met Ile Leu Leu Ala Leu Gly Leu Leu Ala Gly Ser Asn
            115                 120                 125

Ala Thr Lys Leu Phe Thr Ala Ile Thr Phe Asp Ile Ala Met Cys Val
130                 135                 140

Thr Gly Leu Ala Ala Ala Leu Thr Thr Ser Ser His Leu Met Arg Trp
145                 150                 155                 160

Phe Trp Tyr Ala Ile Ser Cys Ala Cys Phe Leu Val Val Leu Tyr Ile
                165                 170                 175

Leu Leu Val Glu Trp Ala Gln Asp Ala Lys Ala Ala Gly Thr Ala Asp
            180                 185                 190

Met Phe Asn Thr Leu Lys Leu Leu Thr Val Val Met Trp Leu Gly Tyr
            195                 200                 205

Pro Ile Val Trp Ala Leu Gly Val Glu Gly Ile Ala Val Leu Pro Val
210                 215                 220

Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
                245                 250                 255

Val Ser Gly Ser Ile Leu Asp Val Pro Ser Ala Ser Gly Thr Pro Ala
            260                 265                 270

Asp Asp Ala Ala Ala Lys Ser Arg Ile Thr Ser Glu Gly Glu Tyr Ile
            275                 280                 285

Pro Leu Asp Gln Ile Asp Ile Asn Val Val Ser Lys Gly Glu Glu Leu
            290                 295                 300

Phe Thr Gly Val Val Pro Ile Leu Val Glu Leu Asp Gly Asp Val Asn
305                 310                 315                 320

Gly His Lys Phe Ser Val Ser Gly Glu Gly Glu Gly Asp Ala Thr Tyr
                325                 330                 335

Gly Lys Leu Thr Leu Lys Phe Ile Cys Thr Thr Gly Lys Leu Pro Val
            340                 345                 350

Pro Trp Pro Thr Leu Val Thr Thr Phe Gly Tyr Gly Leu Gln Cys Phe
            355                 360                 365

Ala Arg Tyr Pro Asp His Met Lys Gln His Asp Phe Phe Lys Ser Ala
370                 375                 380

Met Pro Glu Gly Tyr Val Gln Glu Arg Thr Ile Phe Phe Lys Asp Asp
385                 390                 395                 400

Gly Asn Tyr Lys Thr Arg Ala Glu Val Lys Phe Glu Gly Asp Thr Leu
                405                 410                 415

Val Asn Arg Ile Glu Leu Lys Gly Ile Asp Phe Lys Glu Asp Gly Asn
            420                 425                 430

Ile Leu Gly His Lys Leu Glu Tyr Asn Tyr Asn Ser His Asn Val Tyr
            435                 440                 445

Ile Met Ala Asp Lys Gln Lys Asn Gly Ile Lys Val Asn Phe Lys Ile
450                 455                 460
```

Arg His Asn Ile Glu Asp Gly Ser Val Gln Leu Ala Asp His Tyr Gln
465                 470                 475                 480

Gln Asn Thr Pro Ile Gly Asp Gly Pro Val Leu Leu Pro Asp Asn His
            485                 490                 495

Tyr Leu Ser Tyr Gln Ser Ala Leu Ser Lys Asp Pro Asn Glu Lys Arg
        500                 505                 510

Asp His Met Val Leu Leu Glu Phe Val Thr Ala Ala Gly Ile Thr Leu
    515                 520                 525

Gly Met Asp Glu Leu Tyr Lys Phe Cys Tyr Glu Asn Glu Val
530                 535                 540

<210> SEQ ID NO 4
<211> LENGTH: 223
<212> TYPE: PRT
<213> ORGANISM: Guillardia theta

<400> SEQUENCE: 4

Ala Ser Ser Phe Gly Lys Ala Leu Leu Glu Phe Val Phe Ile Val Phe
1               5                   10                  15

Ala Cys Ile Thr Leu Leu Gly Ile Asn Ala Ala Lys Ser Lys Ala
            20                  25                  30

Ala Ser Arg Val Leu Phe Pro Ala Thr Phe Val Thr Gly Ile Ala Ser
        35                  40                  45

Ile Ala Tyr Phe Ser Met Ala Ser Gly Gly Gly Trp Val Ile Ala Pro
50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
            85                  90                  95

Trp Asp Ile Met Ala Leu Cys Leu Ser Asp Val Leu Met Ile Ala Thr
        100                 105                 110

Gly Ala Phe Gly Ser Leu Thr Val Gly Asn Val Lys Trp Val Trp Trp
    115                 120                 125

Phe Phe Gly Met Cys Trp Phe Leu His Ile Ile Phe Ala Leu Gly Lys
130                 135                 140

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
            165                 170                 175

Val Val Trp Val Phe Ala Glu Gly Phe Gly Asn Phe Ser Val Thr Phe
        180                 185                 190

Glu Val Leu Ile Tyr Gly Val Leu Asp Val Ile Ser Lys Ala Val Phe
    195                 200                 205

Gly Leu Ile Leu Met Ser Gly Ala Ala Thr Gly Tyr Glu Ser Ile
210                 215                 220

<210> SEQ ID NO 5
<211> LENGTH: 310
<212> TYPE: PRT
<213> ORGANISM: Chlamydomonas reinhardtii

<400> SEQUENCE: 5

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

```
Gln Cys Tyr Cys Ala Gly Trp Ile Glu Ser Arg Gly Thr Asn Gly Ala
             35                  40                  45

Gln Thr Ala Ser Asn Val Leu Gln Trp Leu Ala Ala Gly Phe Ser Ile
 50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 6
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 6

Met Asp Tyr Gly Gly Ala Leu Ser Ala Val Gly Arg Glu Leu Leu Phe
 1               5                  10                  15

Val Thr Asn Pro Val Val Asn Gly Ser Val Leu Val Pro Glu Asp
                 20                  25                  30                Asp

Gln Cys Tyr Cys Ala Gly Trp Ile Glu Ser Arg Gly Thr Asn Gly Ala
             35                  40                  45

Gln Thr Ala Ser Asn Val Leu Gln Trp Leu Ala Ala Gly Phe Ser Ile
 50                  55                  60

Leu Leu Leu Met Phe Tyr Ala Tyr Gln Thr Trp Lys Ser Thr Cys Gly
 65                  70                  75                  80
```

```
Trp Glu Glu Ile Tyr Val Cys Ala Ile Glu Met Val Lys Val Ile Leu
             85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Pro
305                 310

<210> SEQ ID NO 7
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 7

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Gly Phe Ser Ile
50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
             85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125
```

```
Pro Val Ile Leu Ile His Leu Ser Asn Leu Thr Gly Leu Ser Asn Asp
    130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
            165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 8
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 8

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175
```

-continued

```
Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 9
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 9

Met Ser Arg Arg Pro Trp Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190
```

```
Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 10
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 10

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205
```

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
                275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 11
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 11

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

```
Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 12
<211> LENGTH: 19
<212> TYPE: PRT
<213> ORGANISM: Artificial Sequence
<220> FEATURE:
<223> OTHER INFORMATION: Synthetic peptide

<400> SEQUENCE: 12

Lys Ser Arg Ile Thr Ser Glu Gly Glu Tyr Ile Pro Leu Asp Gln Ile
1               5                   10                  15

Asp Ile Asn

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)...(2)
<223> OTHER INFORMATION: x = any amino acid

<400> SEQUENCE: 13

Phe Xaa Tyr Glu Asn Glu
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Phe Cys Tyr Glu Asn Glu Val
1               5

<210> SEQ ID NO 15
<211> LENGTH: 18
<212> TYPE: PRT
<213> ORGANISM: Artificial Sequence
<220> FEATURE:
```

```
<223> OTHER INFORMATION: Synthetic peptide

<400> SEQUENCE: 15

Met Thr Glu Thr Leu Pro Pro Val Thr Glu Ser Ala Val Ala Leu Gln
 1               5                  10                  15

Ala Glu
```

OPTOGENETIC CONTROL OF REWARD-RELATED BEHAVIORS

CROSS REFERENCE TO RELATED APPLICATION

This application claims priority to U.S. Provisional Application No. 61/410,692 filed on Nov. 5, 2010, the disclosure of which is incorporated herein by reference in its entirety.

FIELD OF THE INVENTION

This application pertains to compositions comprising animal cells expressing light-responsive opsin proteins on their plasma membranes and methods of using the same to selectively hyperpolarize cholinergic interneurons residing in microcircuits of the nucleus accumbens or dorsal striatum to affect one or more behaviors associated with reward-related conditioning in the animal.

BACKGROUND

Substance abuse and dependency are important problems facing societies all over the world. According to the World Drug Report 2008, about 5% of the world population uses illicit drugs and in 0.6% of the world population, drug use is a problem. In the United States, according to the Substance Abuse and Mental Health Services Administration's (SAMHSA's) National Survey on Drug Use and Health in 2006, 23.6 million persons aged 12 or older needed treatment for an illicit drug or alcohol abuse problem (9.6 percent of the persons aged 12 or older). Of these, only 2.5 million—10.8 percent of those who needed treatment—received it at a specialty facility. Substance abuse and dependency result in enormous loss of productive manpower all over the world and imposes costs on governments and societies in terms of treatment support, insurance payouts, and spending on prevention and de-addiction programs.

Optogenetics is the combination of genetic and optical methods used to control specific events in targeted cells of living tissue, even within freely moving mammals and other animals, with the temporal precision (millisecond-timescale) needed to keep pace with functioning intact biological systems. The hallmark of optogenetics is the introduction of fast light-responsive opsin channel or pump proteins to the plasma membranes of target neuronal cells that allow temporally precise manipulation of neuronal membrane potential while maintaining cell-type resolution through the use of specific targeting mechanisms. Among the microbial opsins which can be used to investigate the function of neural systems are the halorhodopsins (NpHRs), used to promote membrane hyperpolarization when illuminated. In just a few short years, the field of optogenetics has furthered the fundamental scientific understanding of how specific cell types contribute to the function of biological tissues such as neural circuits in vivo. Moreover, on the clinical side, optogenetics-driven research has led to insights into the neurological mechanisms underlying mammalian behavior.

In spite of these advances, the neurophysiological substrates underlying complex human behaviors, such as substance abuse and dependency (addiction) remain poorly understood, despite emerging information on the role that specific areas of the brain play in these behaviors. For example, the nucleus accumbens (NAc) is a collection of neurons that forms the main part of the ventral striatum. The NAc is thought to play an important role in reward, pleasure, laughter, addiction, aggression, fear, and the placebo effect. Acetylcholine is an important and widely studied neurotransmitter, which acts on a variety of receptors and target cells. Some in vivo pharmacological approaches have shown that cholinergic transmission in the NAc is required for reward learning behaviors. Cholinergic interneurons within the NAc are particularly intriguing because they constitute less than 1% of the local neural population, yet they project throughout the NAc and provide its only known cholinergic input. Relevant cholinergic receptors are expressed locally, and nicotinic and muscarinic pharmacological agonists can exert complex influences on medium spiny neurons (MSNs, which represent >95% of the local neuronal population and constitute the output of the NAc). However, the net effect (if any) of the cholinergic interneurons on any aspect of NAc physiology or reward-related behavior is unknown.

What is needed, therefore, is a tool which would permit investigation of the causal role played by cholinergic interneurons within the NAc in reward-related behaviors such as substance dependency. Understanding the neural pathways that underlie addiction may help aid in the discovery and screening of pharmacological therapies to treat patients with such disorders as well as open up the possibility of using such tools to disrupt these behaviors in the brains of drug-addicted individuals.

Throughout this specification, references are made to publications (e.g., scientific articles), patent applications, patents, etc., all of which are herein incorporated by reference in their entirety.

SUMMARY OF THE INVENTION

Provided herein are compositions and methods for disrupting reward-related behaviors in an individual via the use of stably expressed light-responsive opsin proteins capable of altering the membrane polarization state of the cholinergic interneurons of the nucleus accumbens or the striatum of the individual wherein the alteration of the membrane polarization state of the cholinergic interneurons of the nucleus accumbens or the striatum disrupts one or more reward-related behaviors in the animal. In some embodiments, the reward-related behavior is addiction-related behavior. In other embodiments, the addiction-related behavior is cocaine addiction.

Accordingly, in some aspects, provided herein is a non-human animal comprising a light-responsive opsin protein expressed on the cell membrane of a cholinergic interneuron in the nucleus accumbens or the striatum of the animal, wherein the protein is responsive to light and is capable of inducing membrane hyperpolarization of the interneurons when the interneurons are illuminated with the light, wherein the illumination of the opsin disrupts at least one reward-related behavior of the animal.

In other aspects, provided herein is a brain slice comprising a cross section of the nucleus accumbens or the striatum, wherein a light-responsive opsin protein is expressed on the cell membrane of cholinergic interneurons wherein the protein is responsive to light and is capable of inducing membrane hyperpolarization of the interneurons when the interneurons are illuminated with the light, wherein the illumination of the protein disrupts reward-related brain function.

In some aspects, provided herein is a method for disrupting reward-related behavior in an individual comprising: administering a polynucleotide encoding a light-responsive opsin protein to the individual, wherein the light-responsive opsin protein is expressed on the cell membrane of cholinergic interneurons in the nucleus accumbens or the striatum of the individual, and the protein is responsive to light and is capable of inducing membrane hyperpolarization of the interneurons when the interneurons are illuminated with the light, whereby activating the protein by the light disrupts at least one reward-related behavior in the individual. In some embodiments, the polynucleotide is administered to the nucleus accumbens or the striatum of the individual.

In still other aspects, provided herein is a method for treating drug addiction in an individual comprising: administering a polynucleotide encoding a light-responsive opsin protein to the individual, wherein the light-responsive opsin protein is expressed on the cell membrane of cholinergic interneurons in the nucleus accumbens or the striatum of the individual, and the protein is responsive to light and is capable of hyperpolarizing the interneurons when the interneurons are illuminated with the light, whereby activating the protein by the light disrupts reward-related behavior in the individual, wherein the individual no longer desires to take drugs. In some embodiments, the polynucleotide is administered to the nucleus accumbens or the striatum of the individual.

Aspects of the present disclosure relate to control or characterization of reinforced behavior in living animals, as described herein. While the present disclosure is not necessarily limited in these contexts, various aspects of the invention may be appreciated through a discussion of examples using these and other contexts.

Embodiments of the present disclosure are directed toward specially-targeted circuits that are associated with hedonic and/or reinforced behavior. More particular embodiments relate to spatio-temporal control over neural circuitry to identify an association between specific circuit targets associated with and corresponding to reward memory, anhedonia, addiction and/or reinforced behavior.

Particular embodiments of the present disclosure are directed toward inhibition of targeted cells within structures involved in natural reward-related behaviors and/or for reward learning including, but not necessarily limited to, the nucleus accumbens (NAc) or the dorsal striatum. In a particular example, the targeting of specific cholinergic neurons within the NAc is particularly well suited for disrupting the release of acetylcholine by these cholinergic neurons. It has been discovered that such neural inhibition can be effective to targeted neural inhibition can reduce or eliminate undesired effects on the reinforcement of other behaviors, e.g., appetitive or aversive responses. Aspects of the present disclosure relate to stimulation that is specific to temporal, spatial and/or cell-types. In certain embodiments, this inhibition is performed using an optogenetic system that involves the expression of light-responsive opsins in the cells of the neural circuit. In other embodiments, the inhibition can be performed using direct electrical stimulus. Still other embodiments allow for the use of temporally-precise pharmaceuticals.

BRIEF DESCRIPTION OF THE DRAWINGS

Various example embodiments may be more completely understood in consideration of the following description and the accompanying drawings, in which:

FIG. 1 depicts specificity, membrane targeting, and functionality of ChR2 and eNpHR3.0 in ChAT inter-neurons of the NAc. (A) Cre-dependent AAV (expressing either eNpHR3.0-eYFP or ChR2(H134R)-eYFP) was injected into the medial portion of the NAc. (B) Confocal image of an injected slice demonstrates colocalization of eYFP expression with the ChAT antibody, contained with 4',6'-diamidino-2-phenylindole (DAPI). (C) 91.3±1.3% of neurons that expressed YFP also stained for the ChAT antibody (n=418); 93.5±2.8% of neurons that stained for the ChAT antibody also expressed YFP (n=413). Error bars indicate SEM. (D) High-magnification view reveals membrane localization of eNphR3.0-eYFP (left) and ChR2-eYFP (right), costained with ChAT antibody. (E) Membrane potential changes induced by current injection in a ChR2-eYFP-expressing ChAT neuron. $V_M$=–48 mV. Current steps: –60, –20, +20 pA. (F) Membrane potential changes induced by 1 s of 580-nm light in an eNpHR3.0-eYFP-expressing ChAT neuron (peak hyperpolarization: –103 mV). $V_M$=–49 mV. (Inset) Population-averaged peak hyperpolarization (mean±SEM: –83.8±11.9 mV; n=4). (G) Consecutive action potentials in a ChR2-eYFP-expressing ChAT neuron evoked by a 470-nm pulse train (5 ms pulse width; 10 Hz). (H) Average success probability for generating action potentials in ChR2-eYFP-expressing ChAT neurons at different stimulation frequencies (n=4; mean±SEM; 470-nm pulse train, 5-ms pulse width).

FIG. 2 depicts optogenetic photoactivation of ChAT interneurons increases frequency of inhibitory currents and suppresses MSN spiking. (A) ChAT neurons transduced with ChR2-eYFP were activated with blue light (470 nm) in brain slices, and nearby MSNs (eYFP⁻ cells) were whole-cell patch-clamped. (B) (Left) Spontaneous synaptic currents were observed in an MSN in a slice expressing ChR2-eYFP in ChAT neurons. (Middle) Synaptic currents increased in frequency in response to 470-nm light pulses (5-ms pulse width; 10 Hz). (Right) These currents were blocked by $GABA_A$ receptor antagonist SR-95531 (5 mM) and are thus considered IPSCs. 2,3-dihydroxy-6-nitro-7-sulfamoylbenzo[f]quinoxaline-2,3-dione (NBQX) (5 mM) and (RS)-3-(2-Carboxypiperazin-4-yl)-propyl-1-phosphonic acid (RS-CPP) (5 µM) were present in all experiments. (C) Time course of IPSC frequencies for this MSN, showing the effect of light pulses (blue dashed bars) and SR-95531 (black bar). (D) Average percentage increase in IPSC frequency during the light-on periods (normalized to that of light-off periods) as a function of time relative to light pulses (n=6). The blue dashed line indicates the onset of light pulses; error bars denote SEM. (E) Light pulses increased the frequency of IPSCs by 525.8±154.3% (n=6, P=0.01, paired two-tailed t test), whereas the average amplitudes of spontaneous IPSCs were changed by 21.3±28.9% (P>0.05). (F) An optrode (optical fiber attached to a tungsten electrode) was stereotaxically positioned in vivo into a NAc that expressed ChR2-eYFP in ChAT cells. (G) (Top) Voltage trace of an isolated unit that is inhibited by blue light stimulation. (Middle) Raster plot displaying the response of the same unit to five repetitions of the light stimulation, with each action potential represented by a dot. (Bottom) Average and SEM of the firing rate over time for the same unit. (H) Fraction of sites that were inhibited versus excited by light stimulation. (I) Population summary of the time course of response to light stimulation for sites that were inhibited (left; n=13 of 16) or excited (right; n=3 of 16) by light. Solid lines represent average firing rate across sites as a function of time; each dot represents the average firing rate of an individual site. All firing rates are normalized to the mean rate before light stimulation. (F to I) Duration of photostimulation, 10 s; pulse duration, 5 ms; wavelength, 470 nm; frequency, 10 Hz. Epochs of light stimulation are represented by dashed lines.

FIG. 4 depicts ChAT interneurons can be activated by cocaine in slice and required for cocaine conditioning in vivo. (A) The frequency of spontaneous action potentials in a ChAT neuron increased 10 min after bath application of cocaine (5 µM). ACSF, artificial cerebrospinal fluid. (B) Firing rate over time for this ChAT neuron. Horizontal gray bar, application of cocaine; vertical dotted line, 10 min after cocaine application, the time point illustrated in detail in (A) and (C). (C) Population data illustrating the cocaine-induced increase in firing in ChAT neurons, comparing the baseline firing rate (averaged over the min before cocaine application) with the rate after cocaine infusion (averaged between 10 and 12.5 min after onset of cocaine application; gray bars, cells receiving cocaine; white bars, control cells receiving only ACSF; P<0.005, paired two-tailed t test for cocaine-treated group before versus after cocaine; P<0.05 unpaired two-tailed t test comparing cocaine versus control cells after cocaine or vehicle). (D) Schematic illustration of a bilateral cannula system with double fibers inserted to illuminate the medial portion of the NAc. (Left inset) Endpoint of cannula track for all mice used in (H). (Right inset) eYFP expression in NAc of a ChAT::Cre+ mouse injected with Cre-dependent eNpHR3.0-eYFP. (E) Conditioning paradigm for cocaine CPP(H). Mice were conditioned with ip cocaine (20 mg/kg), along with ChAT cell inhibition with eNpHR3.0 (wavelength: 590 nm). (F) Tracking data from representative ChAT::Cre+ and ChAT::Cre− mice on the testing day after cocaine conditioning (day 3). On the previous day (day 2), the mice had received cocaine and light in one left chamber, whereas in the other they received saline. The ChAT::Cre− mouse (but not the ChAT::Cre+ mouse) exhibited a preference for the conditioned chamber. (G) (Left) Fold change in time in conditioned chamber during day 3 versus day 1 of cocaine CPP (conditioning with cocaine and light). Comparison of ChAT::Cre+ and ChAT::Cre− littermates; in both cases injected with Cre-dependent eNpHR3.0 (n=10 ChAT::Cre+, n=12 ChAT::Cre−; P<0.01 for two-tailed t test; three cohorts). (Right) Fold change in time in conditioned chamber during day 3 versus day 1 for conditioning with light alone (no cocaine; n=9 ChAT::Cre+, n=7 ChAT::Cre; P>0.05 for two-tailed t test; three cohorts). Error bars indicate SEM. n.s., not significant. (H) Velocity of virus-injected (Cre-dependent eNpHR3.0) and photostimulated ChAT::Cre+ and ChAT::Cre− mice in the open field (n=10 ChAT::Cre+, n=10 ChAT::Cre−; P>0.05 for two-tailed t test; three cohorts). (I) Same as (II) for track length in open field (n=10 ChAT::Cre+, n=10 ChAT::Cre−; P>0.05 for two-tailed t test; three cohorts). (J) Same as (H) for time in center of open field (n=10 ChAT::Cre+, n=10 ChAT::Cre; P>0.05 for two-tailed t test; three cohorts). (A to J) *P<0.05; P<0.01; *P<0.005.

FIG. 6 depicts ChAT neuron inhibition disrupts cocaine CPP without affecting CPP in the absence of cocaine. (A): Cocaine CPP, same data as FIG. 4G (left panel) but plotted as difference rather than fold-change. Left: Difference in time in cocaine-conditioned chamber after conditioning versus before conditioning. (n=10 ChAT::Cre+, n=12 ChAT::Cre−; p<0.01 for two-tailed t test; 3 cohorts). Right: Difference in preference for cocaine-conditioned chamber after versus before conditioning, where preference is defined as the difference in time spent in conditioned chamber versus the unconditioned chamber (n=10 ChAT::Cre+, n=12 ChAT::Cre−; p<0.01 for two-tailed t-test; 3 cohorts). (B): CPP without cocaine, same data as FIG. 4G (right panel) and same data presentation as A. (For both panels, n=9 ChAT::Cre+, n=7 ChAT::Cre−; p>0.05 for two-tailed t-test; 3 cohorts).

DETAILED DESCRIPTION

Figure 3A:
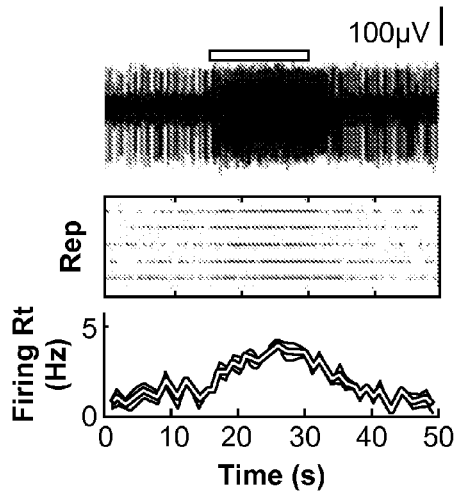
FIG. 3 depicts optogenetic photoinhibition of ChAT interneurons enhances MSN spiking in vivo. (A) (Top) Voltage trace of an isolated unit (recorded from the NAc in vivo) that was excited by optogenetic photoinhibition of the ChAT interneurons with eNpHR3.0. (Middle) Raster plot displaying the response of the same unit to five repetitions of the light stimulation, with each action potential represented by a dot. (Bottom) Average and SEM of the firing rate over time for the same unit. (B) Wavelet analysis reveals power of spiking as a function of frequency and time (average across five repetitions) for the same unit as in (A). (C) Fraction of sites that were inhibited versus excited by light stimulation. (D) Same as (A), for a unit that was inhibited by light stimulation. (E) Population summary of the time course of response to light stimulation for sites that were inhibited (left; n=13 of 17) or excited (right; n=4 of 17) by light. Solid lines represent the average firing rate across sites as a function of time; each dot represents the average firing rate of an individual site. All firing rates are normalized to the mean value before light stimulation. (A to E) Duration of photostimulation, 15 s (constant illumination); wavelength, 560 nm. Epochs of light stimulation are represented by bars.

This invention provides, inter alia, compositions and methods for disrupting reward-related behavior in an individual by selectively altering the electrical membrane potential of the cholinergic interneuron cells of the nucleus accumbens or the dorsal striatum. The invention is based on the inventors' discovery that selective hyperpolarization of the cholinergic interneuron cells of the nucleus accumbens with light-responsive opsin ion pump proteins disrupts reward-seeking behavior in an animal model of drug addiction.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the scope of the present disclosure including aspects defined in the claims.

General Techniques

The practice of the present invention will employ, unless otherwise indicated, conventional techniques of molecular biology, microbiology, cell biology, biochemistry, nucleic acid chemistry, immunology, physiology, and the pathophysiology drug addiction and reward-related behaviors which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000), *Handbook of Experimental Immunology*, 4th edition (D. M. Weir & C. C. Blackwell, eds., Blackwell Science Inc., 1987); and *Gene Transfer Vectors for Mammalian Cells* (J. M. Miller & M. P. Calos, eds., 1987). Other useful references include Harrison's *Principles of Internal Medicine* (McGraw Hill; J. Isseleacher et al., eds.), and *Addiction Research Methods*, (Miller et al, eds., 2010; Wiley-Blackwell, United Kingdom).

DEFINITIONS

As used herein, "reward-related behavior" is a process that reinforces a behavior something that increases the rate, probability, or intensity of a particular behavior in the form of an oftentimes pleasurable response by the delivery or emergence of a stimulus immediately or shortly after performing the behavior. Reward related behaviors can include, but are not limited to, obtaining food, sexual behaviors, gambling behaviors, and/or drug related-addictive behavior.

"Drug-related addictive behavior" is behavior resulting from compulsive substance use and is characterized by apparent dependency on the substance. Symptomatic of addiction-related behavior is (i) overwhelming involvement with the use of the drug, (ii) the securing of its supply, and (iii) a high probability of relapse after withdrawal.

As referred herein, the term "drug" or "narcotic" is meant to include opioids, such as opium and heroin, methamphetamine, cocaine (benzoylmethylecgonine), ketamine, MDMA (3,4-Methylenedioxymethamphetamine; a.k.a. "Ecstasy"), lysergic acid diethylamide (LSD), or cannabinoids. Additionally, narcotic is meant to include alcohol, nicotine, or any other controlled substance.

An "individual" is a mammal including a human. Mammals include, but are not limited to, farm animals, sport animals, pets, primates, mice and rats. Individuals also include companion animals including, but not limited to, dogs and cats. In some aspects, an individual is a non-human animal, such as a mammal. In another aspect, an individual is a human.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including and preferably clinical results. For purposes of this invention, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used herein, the singular form "a", "an", and "the" includes plural references unless indicated otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The Nucleus Accumbens

The nucleus accumbens (NAc), also known as the accumbens nucleus or as the nucleus accumbens septi, is a collection of neurons that forms the main part of the ventral striatum. It is thought to play an important role in reward, pleasure, laughter, addiction, aggression, fear, and the placebo effect. The principal neuronal cell type found in the nucleus accumbens is the medium spiny neuron (MSN). The neurotransmitter produced by these neurons is gamma-aminobutyric acid (GABA), one of the main inhibitory neurotransmitters of the central nervous system. MSNs are also the main projection or output neurons of the nucleus accumbens. While 95% of the neurons in the nucleus accumbens are medium spiny GABA-ergic projection neurons, other neuronal types are also found such as large aspiny cholinergic interneurons, which comprise ~1% of the cells in this region of the brain.

Acetylcholine (ACh) was the first-discovered member of a class of biochemicals that eventually became known as neurotransmitters. In the central nervous system, ACh is important for varied bodily functions, such as sensory and motor processing, sleep, nociception, mood, stress response, attention, arousal, memory, motivation and reward. Another neurotransmitter, dopamine (DA) is also found in the NAc and its release is a critical event mediating the rewarding effects of stimulant drugs (Sofuoglu & Mooney, 2009, *CNS Drugs*, 20(11):939-952). Cholinergic interneurons release ACh in the nucleus accumbens. The activity of MSNs can be modulated by both cholinergic and dopaminergic control, which may be excitatory or inhibitory depending on the receptor subtypes that are stimulated: the D1 dopaminergic and M1 mAChR are excitatory while D2 dopaminergic and M4 mAChR are inhibitory (Calabresi et al., *Lancet Neural.*, 2006, 5(11):974-83). Cholinergic interneurons receive dopaminergic input from the ventral tegmental area (VTA), and glutamatergic input mainly from the prefrontal cortex, hippocampus, and amygdala (Sofuoglu & Mooney, 2009, *CNS Drugs*, 20(11):939-952). Without being bound to theory, it is thought that this DA and glutamate convergence on cholinergic interneurons may provide a mechanism for DA-mediated reward to be associated with glutamate-mediated learning and contextual information (Berlanga et al., Neuroscience. 2003; 120(4):1149-56) Accordingly, cholinergic interneurons are believed to regulate the translation of reward signals into contextually appropriate behavior.

Commonly abused drugs and natural rewards share the mutual action of altering extracellular concentrations of neurotransmitters in the NAc (Di Chiara & Imperato, 1988, *PNAS*, 85(14):5274-8; Phaus, *Curr Opin Neurobiol.*, 1999, 9(6):751-8). Moreover, lesions of the NAc have been shown to decrease the rewarding effects of various stimulants and opiates (Kelsey et al., *Behav Neurosci.*, 1989 103(6):1327-34). Nonetheless, it has been experiments encompassing direct microinfusion of narcotics into the NAc that have provided the most robust evidence for the role it plays in reward-related behavior rewarding states. For example, rodent models of addiction will readily self-administer narcotics such as amphetamine (a dopamine-releasing agent), cocaine (a dopamine reuptake inhibitor), and nomifensine (a dopamine reuptake inhibitor) directly into the NAc, thereby demonstrating that dopamine plays an important role in the NAc to regulate behavior based on reward and motivation (Carlezon & Thomas, *Neuropharmacology*, 2009; 56(Suppl 1): 122-132).

Still unclear, however, are the roles played by the cells of the NAc itself in mediating these complex mammalian behaviors in response to the input of neurotransmitters like dopamine, especially with regard to reward-related behaviors such as substance abuse and dependency (addiction). Also unknown are the specific roles played by the neurotransmitters dopamine and acetylcholine in bringing about reward-related behaviors through the NAc. A reward is a process that reinforces behavior—something that, when offered, causes a behavior to increase in intensity. Reward is an operational concept for describing the positive value an individual ascribes to an object, behavioral act, or an internal physical state. Natural rewards include those that are necessary for the survival of species, such as eating, mating, and fighting. The NAc has been associated with many of these types of rewards-related behaviors, as varied as drug addiction, sex addiction, and gambling addiction.

Light-responsive Opsin Proteins

Provided herein are optogenetic-based compositions and methods for selectively hyperpolarizing cholinergic neurons in the nucleus accumbens and striatum of individuals to disrupt at least one rewards-related behavior in the individual. Optogenetics refers to the combination of genetic and optical methods used to control specific events in targeted cells of living tissue, even within freely moving mammals and other animals, with the temporal precision (millisecond-timescale) needed to keep pace with functioning intact biological systems. Optogenetics requires the introduction of fast light-responsive channel or pump proteins to the plasma membranes of target neuronal cells that allow temporally precise manipulation of neuronal membrane potential while maintaining cell-type resolution through the use of specific targeting mechanisms.

Light-responsive opsins that may be used in the present invention includes opsins that induce hyperpolarization in neurons by light and opsins that induce depolarization in neurons by light. Examples of opsins are shown in Tables 1 and 2 below.

Table 1 shows identified opsins for inhibition of cellular activity across the visible spectrum:

| Opsin Type | Biological Origin | Wavelength Sensitivity | Defined action |
|---|---|---|---|
| NpHR | *Natronomonas pharaonis* | 589 nm max | Inhibition (hyperpolarization) |
| BR | *Halobacterium helobium* | 570 nm max | Inhibition (hyperpolarization) |
| AR | *Acetabulaira acetabulum* | 518 nm max | Inhibition (hyperpolarization) |
| GtR3 | *Guillardia theta* | 472 nm max | Inhibition (hyperpolarization) |
| Mac | *Leptosphaeria maculans* | 470-500 nm max | Inhibition (hyperpolarization) |
| NpHr3.0 | *Natronomonas pharaonis* | 680 nm utility 589 nm max | Inhibition (hyperpolarization) |
| NpHR3.1 | *Natronomonas pharaonis* | 680 nm utility 589 nm max | Inhibition (hyperpolarization) |

Table 2 shows identified opsins for excitation and modulation across the visible spectrum:

| Opsin Type | Biological Origin | Wavelength Sensitivity | Defined action |
|---|---|---|---|
| VChR1 | *Volvox carteri* | 589 nm utility 535 nm max | Excitation (depolarization) |
| DChR | *Dunaliella salina* | 500 nm max | Excitation (depolarization) |
| ChR2 | *Chlamydomonas reinhardtii* | 470 nm max 380-405 nm utility | Excitation (depolarization) |
| ChETA | *Chlamydomonas reinhardtii* | 470 nm max 380-405 nm utility | Excitation (depolarization) |
| SFO | *Chlamydomonas reinhardtii* | 470 nm max 530 nm max | Excitation (depolarization) Inactivation |
| SSFO | *Chlamydomonas reinhardtii* | 445 nm max 590 nm; 390-400 nm | Step-like activation (depolarization) Inactivation |
| C1V1 | *Volvox carteri* and *Chlamydomonas reinhardtii* | 542 nm max | Excitation (depolarization) |
| C1V1 E122 | *Volvox carteri* and *Chlamydomonas reinhardtii* | 546 nm max | Excitation (depolarization) |
| C1V1 E162 | *Volvox carteri* and *Chlamydomonas reinhardtii* | 542 nm max | Excitation (depolarization) |
| C1V1 E122/E162 | *Volvox carteri* and *Chlamydomonas reinhardtii* | 546 nm max | Excitation (depolarization) |

As used herein, a light-responsive opsin (such as NpHR, BR, AR, GtR3, Mac, ChR2, VChR1, DChR, and ChETA) includes naturally occurring protein and functional variants, fragments, fusion proteins comprising the fragments or the full length protein. In some embodiments, the signal peptide may be removed. A variant may have an amino acid sequence at least about any of 90%, 91%, 92%, 93%, 94%, 95%, 96%, 97%, 98%, 99%, or 100% identical to the naturally occurring protein sequence. A functional variant may have the same or similar hyperpolarization function or depolarization function as the naturally occurring protein.

Enhanced Intracellular Transport Amino Acid Motifs

The present disclosure provides for the modification of light-responsive opsin proteins expressed in a cell by the addition of one or more amino acid sequence motifs which enhance transport to the plasma membranes of mammalian cells. Light-responsive opsin proteins having components derived from evolutionarily simpler organisms may not be expressed or tolerated by mammalian cells or may exhibit impaired subcellular localization when expressed at high levels in mammalian cells. Consequently, in some embodiments, the light-responsive opsin proteins expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive opsin protein transport to the plasma membranes of mammalian cells can be fused to the N-terminus, the C-terminus, or to both the N- and C-terminal ends of the light-responsive opsin protein. Optionally, the light-responsive opsin protein and the one or more amino acid sequence motifs may be separated by a linker. In some embodiments, the light-responsive opsin protein can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:12).

Additional protein motifs which can enhance light-responsive opsin protein transport to the plasma membrane of a cell are described in U.S. patent application Ser. No. 12/041,628, which is incorporated herein by reference in its entirety. In some embodiments, the signal peptide sequence in the protein can be deleted or substituted with a signal peptide sequence from a different protein.

Light-responsive Chloride Pumps

In some aspects of the methods provided herein, one or more members of the Halorhodopsin family of light-responsive chloride pumps are expressed on the plasma membranes of the cholinergic interneurons of the nucleus accumbens or the striatum.

In some aspects, said one or more light-responsive chloride pump proteins expressed on the plasma membranes of the nerve cells of the cholinergic interneurons of the nucleus accumbens or the striatum can be derived from *Natronomonas pharaonis*. In some embodiments, the light-responsive chloride pump proteins can be responsive to amber light as well as red light and can mediate a hyperpolarizing current in the interneuron when the light-responsive chloride pump proteins are illuminated with amber or red light. The wavelength of light which can activate the light-responsive chloride pumps can be between about 580 and 630 nm. In some embodiments, the light can be at a wavelength of about 590 nm or the light can have a wavelength greater than about 630 nm (e.g. less than about 740 nm). In another embodiment, the light has a wavelength of around 630 nm. In some embodiments, the light-responsive chloride pump protein can hyperpolarize a neural membrane for at least about 90 minutes when exposed to a continuous pulse of light. In some embodiments, the light-responsive chloride pump protein can comprise an amino acid sequence at least about 90%, 91%, 92%, 93%, 94%, 95%, 96%, 97%, 98%, 99%, or 100% identical to the sequence shown in SEQ ID NO: 1. Additionally, the light-responsive chloride pump protein can comprise substitutions, deletions, and/or insertions introduced into a native amino acid sequence to increase or decrease sensitivity to light, increase or decrease sensitivity to particular wavelengths of light, and/or increase or decrease the ability of the light-responsive protein to regulate the polarization state of the plasma membrane of the cell. In some embodiments, the light-responsive chloride pump protein contains one or more conservative amino acid substitutions. In some embodiments, the light-responsive protein contains one or more non-conservative amino acid substitutions. The light-responsive protein comprising substitutions, deletions, and/or insertions introduced into the native amino acid sequence suitably retains the ability to hyperpolarize the plasma membrane of a neuronal cell in response to light.

Additionally, in other aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO: 1 and an endoplasmic reticulum (ER) export signal. This ER export signal can be fused to the C-terminus of the core amino acid sequence or can be fused to the N-terminus of the core amino acid sequence. In some embodiments, the ER export signal is linked to the core amino acid sequence by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal can comprise the amino acid sequence FXYENE (SEQ ID NO:13), where X can be any amino acid. In another embodiment, the ER export signal can comprise the amino acid sequence VXXSL, where X can be any amino acid. In some embodiments, the ER export signal can comprise the amino acid sequence FCYENEV (SEQ ID NO:14).

In other aspects, the light-responsive chloride pump proteins provided herein can comprise a light-responsive protein expressed on the cell membrane, wherein the protein comprises a core amino acid sequence at least about 90%, 91%, 92%, 93%, 94%, 95%, 96%, 97%, 98%, 99%, or 100% identical to the sequence shown in SEQ ID NO: 1 and a trafficking signal (e.g., which can enhance transport of the light-responsive chloride pump protein to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker which can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal can be derived from the amino acid sequence of the human inward rectifier potassium channel $K_{ir}2.1$. In other embodiments, the trafficking signal can comprise the amino acid sequence KSRITSEGEYIPLDQIDINV (SEQ ID NO:12).

In some aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO: 1 and at least one (such as one, two, three, or more) amino acid sequence motifs which enhance transport to the plasma membranes of mammalian cells selected from the group consisting of an ER export signal, a signal peptide, and a membrane trafficking signal. In some embodiments, the light-responsive chloride pump protein comprises an N-terminal signal peptide, a C-terminal ER Export signal, and a C-terminal trafficking signal. In some embodiments, the C-terminal ER Export signal and the C-terminal trafficking signal can be linked by a linker. The linker can comprise any of about 5, 10, 20, 30, 40, 50, 75, 100, 125, 150, 175, 200, 225, 250, 275, 300, 400, or 500 amino acids in length. The linker can also further comprise a fluorescent protein, for example, but not limited to, a yellow fluorescent protein, a red fluorescent protein, a green fluorescent protein, or a cyan fluorescent protein. In some embodiments the ER Export signal can be more C-terminally located than the trafficking signal. In other embodiments the trafficking signal is more C-terminally located than the ER Export signal. In some embodiments, the signal peptide comprises the amino acid sequence MTETLPPVTESAVALQAE (SEQ ID NO:15). In another embodiment, the light-responsive chloride pump protein comprises an amino acid sequence at least 95% identical to SEQ ID NO:2.

Moreover, in other aspects, the light-responsive chloride pump proteins can comprise a core amino acid sequence at least about 90%, 91%, 92%, 93%, 94%, 95%, 96%, 97%, 98%, 99%, or 100% identical to the sequence shown in SEQ ID NO: 1, wherein the N-terminal signal peptide of SEQ ID NO:1 is deleted or substituted. In some embodiments, other signal peptides (such as signal peptides from other opsins) can be used. The light-responsive protein can further comprise an ER transport signal and/or a membrane trafficking signal described herein. In some embodiments, the light-responsive chloride pump protein comprises an amino acid sequence at least 95% identical to SEQ ID NO:3.

Also provided herein are polynucleotides encoding any of the light-responsive chloride ion pump proteins described herein, such as a light-responsive protein comprising a core amino acid sequence at least about 90%, 91%, 92%, 93%, 94%, 95%, 96%, 97%, 98%, 99%, or 100% identical to the sequence shown in SEQ ID NO:1, an ER export signal, and a membrane trafficking signal. In another embodiment, the polynucleotides comprise a sequence which encodes an amino acid at least 95% identical to SEQ ID NO:2 and SEQ ID NO:3. The polynucleotides may be in an expression vector (such as, but not limited to, a viral vector described herein). The polynucleotides may be used for expression of the light-responsive chloride ion pump proteins in the cholinergic neurons of the NAc or the striatum.

In some embodiments, the light-responsive opsin protein is a NpHR opsin protein comprising an amino acid sequence at least 95%, at least 96%, at least 97%, at least 98%, at least 99% or 100% identical to the sequence shown in SEQ ID NO:1. In some embodiments, the NpHR opsin protein further comprises an endoplasmic reticulum (ER) export signal and/or a membrane trafficking signal. For example, the NpHR opsin protein comprises an amino acid sequence at least 95% identical to the sequence shown in SEQ ID NO:1 and an endoplasmic reticulum (ER) export signal. In some embodiments, the amino acid sequence at least 95% identical to the sequence shown in SEQ ID NO:1 is linked to the ER export signal through a linker. In some embodiments, the ER export signal comprises the amino acid sequence FXYENE (SEQ ID NO:13), where X can be any amino acid. In another embodiment, the ER export signal comprises the amino acid sequence VXXSL, where X can be any amino acid. In some embodiments, the ER export signal comprises the amino acid sequence FCYENEV (SEQ ID NO:14). In some embodiments, the NpHR opsin protein comprises an amino acid sequence at least 95% identical to the sequence shown in SEQ ID NO:1, an ER export signal, and a membrane trafficking signal. In other embodiments, the NpHR opsin protein comprises, from the N-terminus to the C-terminus, the amino acid sequence at least 95% identical to the sequence shown in SEQ ID NO:1, the ER export signal, and the membrane trafficking signal. In other embodiments, the NpHR opsin protein comprises, from the N-terminus to the C-terminus, the amino acid sequence at least 95% identical to the sequence shown in SEQ ID NO:1, the membrane trafficking signal, and the ER export signal. In some embodiments, the membrane trafficking signal is derived from the amino acid sequence of the human inward rectifier potassium channel $K_{ir}2.1$. In some embodiments, the membrane trafficking signal comprises the amino acid sequence K S R I T S E G E Y I P L D Q I D I N V (SEQ ID NO://). In some embodiments, the membrane trafficking signal is linked to the amino acid sequence at least 95% identical to the sequence shown in SEQ ID NO:1 by a linker. In some embodiments, the membrane trafficking signal is linked to the ER export signal through a linker. The linker may comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-responsive opsin protein further comprises an N-terminal signal peptide. In some embodiments, the light-responsive opsin protein comprises the amino acid sequence of SEQ ID NO:2. In some embodiments, the light-responsive opsin protein comprises the amino acid sequence of SEQ ID NO:3.

Further disclosure related to light-responsive chloride pump proteins can be found in U.S. Patent Application Publication Nos: 2009/0093403 and 2010/0145418 as well as in International Patent Application No: PCT/US2011/028893, the disclosures of each of which are hereby incorporated by reference in their entireties.

Light-responsive Proton Pumps

In some aspects of the compositions and methods provided herein, one or more light-responsive proton pumps are expressed on the plasma membranes of the cholinergic interneurons of the nucleus accumbens or the striatum.

In some embodiments, the light-responsive proton pump protein can be responsive to blue light and can be derived from *Guillardia theta*, wherein the proton pump protein can be capable of mediating a hyperpolarizing current in the cell when the cell is illuminated with blue light. The light can have a wavelength between about 450 and about 495 nm or can have a wavelength of about 490 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:4. The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:4 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. The polynucleotides may be used for expression of the light-responsive opsin protein in neural cells (e.g. the cholinergic interneurons of the NAc or the striatum).

Further disclosure related to light-responsive proton pump proteins can be found in International Patent Application No. PCT/US2011/028893, the disclosure of which is hereby incorporated by reference in its entirety.

Light-responsive Channel Proteins

In some aspects of the methods provided herein, one or more members of the Channelrhodopsin family of light-responsive ion channels are expressed on the plasma membranes of the cholinergic interneurons of the nucleus accumbens or the striatum.

In some aspects, the light-responsive cation channel protein can be derived from *Chlamydomonas reinhardtii*, wherein the cation channel protein can be capable of mediating a depolarizing current in the cell when the cell is illuminated with light. In another embodiment, the light-responsive cation channel protein can comprise an amino acid sequence at least about 90%, 91%, 92%, 93%, 94%, 95%, 96%, 97%, 98%, 99%, or 100% identical to the sequence shown in SEQ ID NO:5. The light used to activate the light-responsive cation channel protein derived from *Chlamydomonas reinhardtii* can have a wavelength between about 460 and about 495 nm or can have a wavelength of about 470 nm. Additionally, the light can have an intensity of at least about 100 Hz. In some embodiments, activation of the light-responsive cation channel derived from *Chlamydomonas reinhardtii* with light having an intensity of 100 Hz can cause depolarization-induced synaptic depletion of the neurons expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can contain one or more conservative amino acid substitutions and/or one or more non-conservative amino acid substitutions. The light-responsive cation channel protein comprising substitutions, deletions, and/or insertions introduced into the native amino acid sequence suitably retains the ability to depolarize the plasma membrane of a neuronal cell in response to light.

In other embodiments, the light-responsive cation channel protein can be a step function opsin (SFO) protein or a stabilized step function opsin (SSFO) protein that can have specific amino acid substitutions at key positions throughout the retinal binding pocket of the protein. In some embodiments, the SFO protein can have a mutation at amino acid residue C128 of SEQ ID NO:5. In other embodiments, the SFO protein has a C128A mutation in SEQ ID NO:5. In other embodiments, the SFO protein has a C128S mutation in SEQ ID NO:5. In another embodiment, the SFO protein has a C128T mutation in SEQ ID NO:5. In some embodiments, the SFO protein can comprise an amino acid sequence at least about 90%, 91%, 92%, 93%, 94%, 95%, 96%, 97%, 98%, 99%, or 100% identical to the sequence shown in SEQ ID NO:6 or SEQ ID NO:7.

In other embodiments, the light-responsive cation channel protein can be a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. Additionally, in some embodiments, the invention can include polypeptides comprising substituted or mutated amino acid sequences, wherein the mutant polypeptide retains the characteristic light-responsive nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells. In some embodiments, the C1V1 protein can comprise an amino acid sequence at least about 90%, 91%, 92%, 93%, 94%, 95%, 96%, 97%, 98%, 99%, or 100% identical to the sequence shown in SEQ ID NOs:8, 9, 10, or 11.

Further disclosure related to light-responsive cation channel proteins can be found in U.S. Patent Application Publication No. 2007/0054319 and International Patent Application Publication Nos. WO 2009/131837 and WO 2007/024391. Further disclosure related to SFO or SSFO proteins can be found in International Patent Application Publication No. WO 2010/056970 and U.S. Provisional Patent Application Nos. 61/410,704 and 61/511,905. Further disclosure related to C1V1 chimeric cation channels as well as mutant variants of the same can be found in U.S. Provisional Patent Application Nos. 61/410,736, 61/410,744, and 61/511,912. The disclosures of each of the aforementioned references related to specific light-responsive opsin proteins are hereby incorporated by reference in their entireties.

Polynucleotides

The disclosure also provides polynucleotides comprising a nucleotide sequence encoding a light-responsive opsin protein described herein. In some embodiments, the polynucleotide comprises an expression cassette. In some embodiments, the polynucleotide is a vector comprising the above-described nucleic acid. In some embodiments, the nucleic acid encoding a light-responsive opsin protein of the disclosure is operably linked to a promoter. Promoters are well known in the art. Any promoter that functions in a cholinergic interneuron can be used for expression of the light-responsive proteins and/or any variant thereof of the present disclosure. Initiation control regions or promoters, which are useful to drive expression of the light-responsive opsin proteins or variant thereof in a specific animal cell are numerous and familiar to those skilled in the art. Virtually any promoter capable of driving these nucleic acids can be used. In some embodiments, the promoter used to drive expression of the light-responsive protein can be the choline acetyltransferase (ChAT) promoter, which is capable of driving robust expression of transgenes in cholinergic interneuron (See, e.g., Gong et al., *J. Neurosci.*, 27, 9817-9823 (2007)).

Also provided herein are vectors comprising a nucleotide sequence encoding a light-responsive opsin protein or any variant thereof described herein. The vectors that can be administered according to the present invention also include vectors comprising a nucleotide sequence which encodes an RNA (e.g., an mRNA) that when transcribed from the polynucleotides of the vector will result in the accumulation of light-responsive proteins on the plasma membranes of target animal cells. Vectors which may be used, include, without limitation, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, the vector is a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized.

It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

AAV vectors may be prepared using standard methods in the art. Adeno-associated viruses of any serotype are suitable (see, e.g., Blacklow, pp. 165-174 of "*Parvoviruses and Human Disease*" J. R. Pattison, ed. (1988); Rose, *Comprehensive Virology* 3:1, 1974; P. Tattersall "The Evolution of Parvovirus Taxonomy" In *Parvoviruses* (J R Kerr, S F Cotmore. M E Bloom, R M Linden, C R Parrish, Eds.) p 5-14, Hudder Arnold, London, UK (2006); and D E Bowles, J E Rabinowitz, R J Samulski "The Genus Dependovirus" (J R Kerr, S F Cotmore. M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the invention are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the invention includes a recombinant virus particle (recombinant because it contains a recombinant polynucleotide) comprising any of the vectors described herein. Methods of producing such particles are known in the art and are described in U.S. Pat. No. 6,596, 535, the disclosure of which is hereby incorporated by reference in its entirety.

Delivery of Light-responsive Opsin Proteins

In some aspects, polynucleotides encoding the light-responsive opsin proteins disclosed herein (for example, an AAV vector) can be delivered directly to the cholinergic interneurons of the nucleus accumbens or striatum using a needle, catheter, or related device, using neurosurgical techniques known in the art, such as by stereotactic injection (See, e.g., Stein et al., *J. Virol*, 73:34243429, 1999; Davidson et al., *PNAS,* 97:3428-3432, 2000; Davidson et al., *Nat. Genet.* 3:219-223, 1993; and Alisky & Davidson, *Hum. Gene Ther.* 11:2315-2329, 2000, the contents of each of which are hereby incorporated by reference herein in their entireties) or fluoroscopy.

In other aspects, any of the light-responsive opsin proteins can be expressed in the cholinergic interneurons of the nucleus accumbens or striatum of a transgenic animal. For example, a transgenic mouse line can be employed using Cre-recombinase under control of the choline acetyltransferase (ChAT) promoter. A Cre-inducible adeno-associated virus (AAV) vector carrying the light-responsive opsin gene can then be stereotaxically injected into the NAc.

Other methods to deliver the light-responsive proteins to cholinergic interneurons can also be used, such as, but not limited to, transfection with ionic lipids or polymers, electroporation, optical transfection, impalefection, or via gene gun.

Light Sources

Any device that is capable of applying light having a wavelength to activate the light-responsive proteins expressed in a neuron may be used to depolarize and/or hyperpolarize the neuron. For example, a light-delivery device for activating ion channels and/or ionic pumps to affect the membrane voltage of one or more neurons may be used. A light-delivery device can be configured to provide optical stimulus to a target region of the brain. The light-delivery device may comprise a base, a cannula guide that is attached to the base, and one or more optical conduits attached to the base via the cannula guide. The base may comprise one or more light delivery ports that are positioned to deliver light from the optical conduits to targeted tissue regions, such as the nucleus accumbens or the striatum. The optical conduits may be optical fibers, where the proximal end of the fiber is attached to an optical light source, and the distal end is in communication with the light delivery ports. The optical light source may be capable of providing continuous light and/or pulsed light, and may be programmable to provide light in pre-determined pulse sequences. The light delivery device may have any number of optical conduits as may be desirable, e.g., 1, 2, 3, 4, 5, 10, 15, 20, etc. The optical conduits may each carry light of the same or different wavelengths. The delivered light may have a wavelength between 450 nm and 600 nm, such as yellow or green or blue light. The light delivery device may have any number of light delivery ports as may be desirable, e.g., 1, 2, 3, 4, 5, 10, 15, 20, etc. In some variations, there may be the same number of light delivery ports as optical conduits while in other variations, there may be different number of optical conduits and light delivery ports. For example, there may be a single optical conduit that conveys light to two or more light delivery ports. Alternatively or additionally, a single optical conduit may connect to a single light delivery port. The cannula guide may be configured to help secure and align the optical conduits with the light delivery ports. In some embodiments, the light delivery device is configured to deliver light to the nucleus accumbens or the striatum to disrupt at least one reward-related behavior in an individual. Light delivery devices may also comprise one or more measurement electrodes that may be configured for measuring neural activity. For example, measurement electrodes may record changes in the membrane potential (e.g., action potentials) and/or current flow across a membrane of one or more neurons as the neurons respond to a stimulus. In some variations, the measurement electrodes may measure the electrical response of one or more neurons to optical stimulation. Measurement electrodes may be extracellular or intracellular electrodes.

In other aspects, the light delivery device can be an implantable light source that does not require physical tethering to an external power source. The implantable light source can comprise an inner body, the inner body having at least one means for generating light which is configured to a power source. In some embodiments, the power source can be an internal battery for powering the light-generating means. In another embodiment, the implantable light source can comprise an external antenna for receiving wirelessly transmitted electromagnetic energy from an external source for powering the light-generating means. The wirelessly transmitted electromagnetic energy can be a radio wave, a microwave, or any other electromagnetic energy source that can be transmitted from an external source to power the light-generating means of the implantable light source. In one embodiment, the light-generating means is controlled by an integrated circuit produced using semiconductor or other processes known in the art.

In some aspects, the light means can be a light emitting diode (LED). In some embodiments, the LED can generate blue and/or green light. In other embodiments, the LED can generate amber, yellow and/or blue light. In some embodiments, several micro LEDs are embedded into the inner body of the implantable light source. In other embodiments, the light-generating means is a solid state laser diode or any other means capable of generating light. The light generating means can generate light having an intensity sufficient to activate the light-responsive proteins expressed on the plasma membrane of the nerves in proximity to the light source. In some embodiments, the intensity of the light reaching the cholinergic interneurons of the NAc or striatum produced by the light-generating means has an intensity of any of about 0.05 mW/mm$^2$, 0.1 mW/mm$^2$, 0.2 mW/mm$^2$, 0.3 mW/mm$^2$, 0.4 mW/mm$^2$, 0.5 mW/mm$^2$, about 0.6 mW/mm$^2$, about 0.7 mW/mm$^2$, about 0.8 mW/mm$^2$, about 0.9 mW/mm$^2$, about 1.0 mW/mm$^2$, about 1.1 mW/mm$^2$, about 1.2 mW/mm$^2$, about 1.3 mW/mm$^2$, about 1.4 mW/mm$^2$, about 1.5 mW/mm$^2$, about 1.6 mW/mm$^2$, about 1.7 mW/mm$^2$, about 1.8 mW/mm$^2$, about 1.9 mW/mm$^2$, about 2.0 mW/mm$^2$, about 2.1 mW/mm$^2$, about 2.2 mW/mm$^2$, about 2.3 mW/mm$^2$, about 2.4 mW/mm$^2$, about 2.5 mW/mm$^2$, about 3 mW/mm$^2$, about 3.5 mW/mm$^2$, about 4 mW/mm$^2$, about 4.5 mW/mm$^2$, about 5 mW/mm$^2$, about 5.5 mW/mm$^2$, about 6 mW/mm$^2$, about 7 mW/mm$^2$, about 8 mW/mm$^2$, about 9 mW/mm$^2$, or about 10 mW/mm$^2$, inclusive, including values in between these numbers.

In some aspects, the light-generating means can be externally activated by an external controller. The external controller can comprise a power generator which can be mounted to a transmitting coil. In some embodiments of the external controller, a battery can be connected to the power generator, for providing power thereto. A switch can be connected to the power generator, allowing an individual to manually activate or deactivate the power generator. In some embodiments, upon activation of the switch, the power generator can provide power to the light-generating means on the light source through electromagnetic coupling between the transmitting coil on the external controller and the external antenna of the implantable light source. The transmitting coil can establish an electromagnetic coupling with the external antenna of the implantable light source when in proximity thereof, for supplying power to the light-generating means and for transmitting one or more control signals to the implantable light source. In some embodiments, the electromagnetic coupling between the transmitting coil of the external controller and the external antenna of the implantable light source can be radio-frequency magnetic inductance coupling. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). However, other coupling techniques may be used, such as an optical receiver, infrared, or a biomedical telemetry system (See, e.g., Kiourti, "Biomedical Telemetry: Communication between Implanted Devices and the External World, *Opticon* 1826, (8): Spring, 2010).

Examples of light stimulation devices, including light sources, can be found in International Patent Application Nos: PCT/US08/50628 and PCT/US09/49936 and in Llewellyn et al., 2010, *Nat. Med.*, 16(10):161-165, the disclosures of each of which are hereby incorporated herein in their entireties.

Light-responsive Opsins Expressed in Cholinergic Interneurons

Provided herein are non-human animals comprising a light-responsive opsin protein expressed on the cell membrane of a cholinergic interneuron in the nucleus accumbens or the striatum of the animal, wherein the protein is responsive to light and is capable of altering the membrane polarization state of the interneurons when the interneurons are illuminated with the light, wherein the illumination of the opsin disrupts at least one reward-related behavior of the animal. In some embodiments, the light-responsive protein is selected from the group consisting of NpHR, BR, AR and GtR3 described herein. For example, any of the NpHR proteins described herein may be expressed on the cell membrane of the target neurons. In some embodiments, the reward-related behavior is drug-related addictive behavior. The drug can be any addictive drug such as, but not limited to, opioids (for example, opium and heroin), methamphetamine, cocaine, ketamine, MDMA (3,4-Methylenedioxymethamphetamine), lysergic acid diethylamide, cannabinoids, alcohol, nicotine, or any other controlled substance. In one embodiment, the drug is cocaine. In another embodiment, the reward-related behavior is cocaine addiction.

Also provided herein are brain tissue slices comprising the nucleus accumbens or striatum, wherein a light-responsive protein is expressed on the cell membrane of cholinergic interneurons of the nucleus accumbens, wherein the protein is responsive to light and is capable of altering the membrane polarization state of the interneurons when the interneurons are illuminated with the light, wherein the illumination of the protein disrupts at least one reward-related behavior. In some embodiments, the brain tissue slices are cultured tissue slices taken from the non-human animals described herein. In some embodiments, the light-responsive protein is capable of hyperpolarizing the membranes of cholinergic interneurons of the nucleus accumbens and is selected from the group consisting of NpHR, BR, AR and GtR3 described herein. For example, any of the NpHR proteins described herein may be expressed on the cell membrane of the target neurons. In other embodiments, the light-responsive protein is capable of depolarizing the membrane of cholinergic interneurons of the nucleus accumbens and is selected from the group consisting of ChR2, SFO, SSFO, and the C1V1s described herein.

Methods of the Invention

In some aspects, provided herein are methods for disrupting reward-related behavior in an individual comprising: administering a polynucleotide encoding a light-responsive opsin protein to the individual, wherein the light-responsive opsin protein is expressed on the cell membrane of cholinergic interneurons in the nucleus accumbens or the striatum of the individual, and the protein is responsive to light and is capable of inducing membrane hyperpolarization of the interneurons when the interneurons are illuminated with the light, whereby activating the protein by the light disrupts at least one reward-related behavior in the individual. In some embodiments, the polynucleotide is administered to the nucleus accumbens or the striatum of the individual. In some embodiments, the light-responsive protein is selected from the group consisting of NpHR, BR, AR and GtR3 described herein. For example, any of the NpHR proteins described herein may be expressed on the cell membrane of the target neurons. In some embodiments, the reward-related behavior is drug-related addictive behavior. The drug can be any addictive drug such as, but not limited to, opioids (for example, opium and heroin), methamphetamine, cocaine, ketamine, MDMA (3,4-Methylenedioxymethamphetamine), lysergic acid diethylamide, cannabinoids, alcohol, nicotine, or any other controlled substance. In one embodiment, the drug is cocaine. In another embodiment, the reward-related behavior is cocaine addiction. In some embodiments, the individual is a non-human animal. In some embodiments, the individual is a human. In some embodiments, the polynucleotide further comprises a promoter (e.g., a ChAT promoter) operably linked to the light-responsive opsin protein. In some embodiments, the polynucleotide is a vector.

Methods for measuring disruption of reward-related behavior are many and well known in the art (See, e.g., *Addiction Research Methods*, (Miller et al., eds., 2010; Wiley-Blackwell, United Kingdom)). For example, cocaine addiction and disruption of drug-related addictive behavior can be assessed by using conditioned place preference (CPP; also known as environmental place) conditioning. CPP is a technique commonly used in animal studies to evaluate preferences for environmental stimuli that have been associated with a positive or negative reward. The technique is often used to determine the addictive potential of drugs. The procedure involves several trials where the animal is presented with the positive stimulus (e.g., food, neurotransmitters or the effects of a drug of abuse) paired with placement in a distinct environment containing various cues (e.g., tactile, visual, and/or olfactory). When later tested in the normal state, approaches and the amount of time spent in the compartments previously associated with the positive stimulus serves as an indicator of preference and a measure of reward learning.

In other aspects, provided herein is a method for treating drug addiction in an individual comprising: administering a polynucleotide encoding a light-responsive opsin protein the individual, wherein the light-responsive opsin protein is expressed on the cell membrane of cholinergic interneurons in the nucleus accumbens or the striatum of the individual, and the protein is responsive to light and is capable of hyperpolarizing the interneurons when the interneurons are illuminated with the light, whereby activating the protein by the light disrupts reward-related behavior in the individual, wherein the individual no longer desires to take drugs. In some embodiments, the polynucleotide is administered to the nucleus accumbens or the striatum of the individual. In some embodiments, the light-responsive protein is selected from the group consisting of NpHR, BR, AR and GtR3 described herein. For example, any of the NpHR proteins described herein may be expressed on the cell membrane of the target neurons. In some embodiments, the reward-related behavior is drug-related addictive behavior. The drug can be any addictive drug such as, but not limited to, opioids (for example, opium and heroin), methamphetamine, cocaine, ketamine, MDMA (3,4-Methylenedioxymethamphetamine), lysergic acid diethylamide, cannabinoids, alcohol, nicotine, or any other controlled substance. In one embodiment, the drug is cocaine. In another embodiment, the reward-related behavior is cocaine addiction. In some embodiments, the individual is a non-human animal. In another embodiment, the individual is a human. In some embodiments, the individual no longer experiences the positively reinforcing experience of using the drug. In some embodiments, the polynucleotide further comprises a promoter (e.g., a ChAT promoter) operably linked to the light-responsive opsin protein. In some embodiments, the polynucleotide is a vector.

Exemplary Embodiments

The present disclosure is believed to be useful for control or characterization of reinforced behavior in living animals. Specific applications of the present invention facilitate assessing addiction and other reinforced behaviors in living animals. As many aspects of the example embodiments disclosed herein relate to and significantly build on previous developments in this field, the following discussion summarizes such previous developments to provide a solid understanding of the foundation and underlying teachings from which implementation details and modifications might be drawn. It is in this context that the following discussion is provided and with the teachings in the references incorporated herein by reference. While the present invention is not necessarily limited to such applications, various aspects of the invention may be appreciated through a discussion of various examples using this context.

Figure 10:
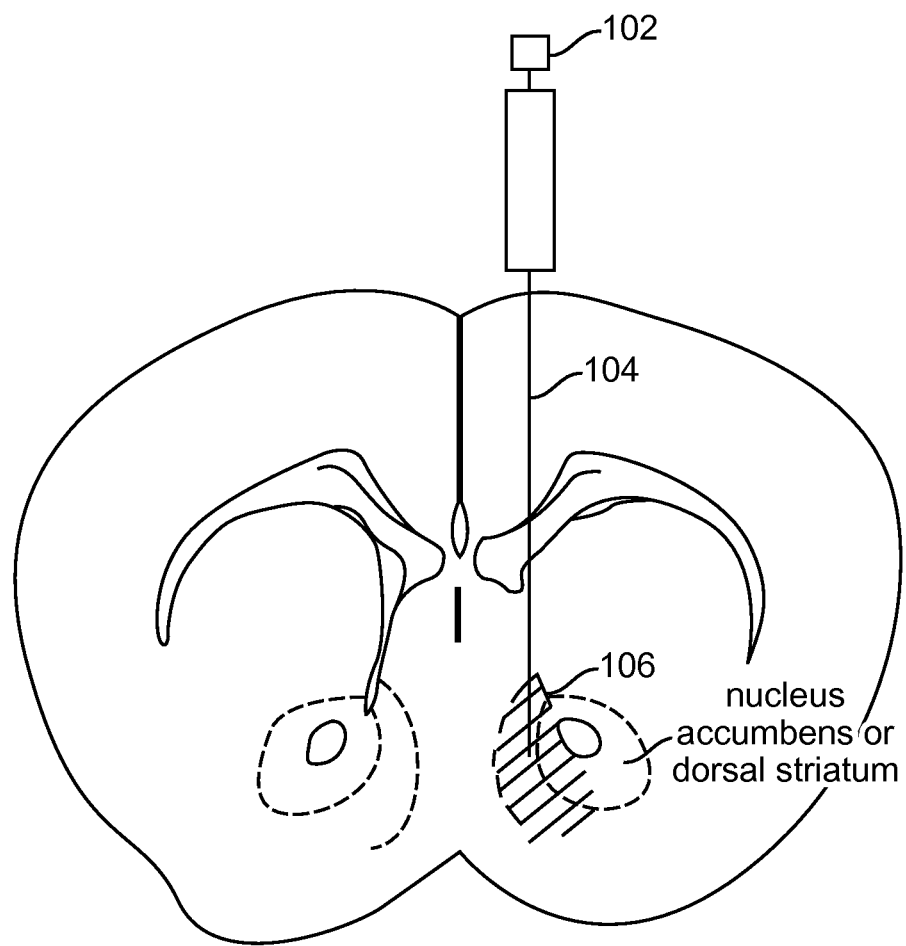
FIG. 10 depicts a system for controlling the nucleus accumbens (NAc) or the dorsal striatum, consistent with an embodiment of the present disclosure.

FIG. 10 depicts a system for controlling the nucleus accumbens (NAc) or the dorsal striatum, consistent with an embodiment of the present disclosure. A stimulus source 102 is linked 104 to a target location 106. This target location can be located at or near the NAc or the dorsal striatum, e.g., the depicted location aligns generally with the NAc, but is not necessarily so limited.

Consistent with embodiments of the present disclosure, stimulus source 102 can include an optical light source. The optical light source is optically linked to the target location 106 (e.g., using fiber optics). The target location 106 is configured to include cells that respond to optical stimulus. These cells can include cells that express light-responsive opsins including, but not limited to ion pumps (e.g, NpHR and NpHR variants) and/or ion channels (e.g., ChR2/ChR1 and ChR2/ChR1 variants).

Consistent with various other embodiments of the present disclosure, stimulus source 102 can include a drug/pharmacological delivery device. The delivery device is linked to the target location (e.g., using a delivery lumen).

Certain embodiments of the present disclosure are directed toward targeting of cholinergic neurons of structures involved in natural reward-related behaviors and/or in reward learning (e.g., NAc or dorsal striatum) using a stimulus source. The stimulus source 102 provides a stimulus that controls the release of acetylcholine within the structure. In certain embodiments, this control is accomplished in a localized spatio-temporal manner that can be particularly useful for disrupting the addictive properties of substance abuse without noticeably affecting the reinforcement of other behaviors, e.g., appetitive or aversive responses. The stimulus can be provided from a number of different stimulus sources. Non-limiting examples include activating light-responsive opsins expressed in cholinergic neurons, applying an electrical pulse through one or more electrodes positioned near the cholinergic neurons, releasing a drug at a location proximate to the cholinergic neurons, applying a magnetic field to a location proximate to the cholinergic neurons and/or surgical alternations based upon this understanding.

Figure 11:
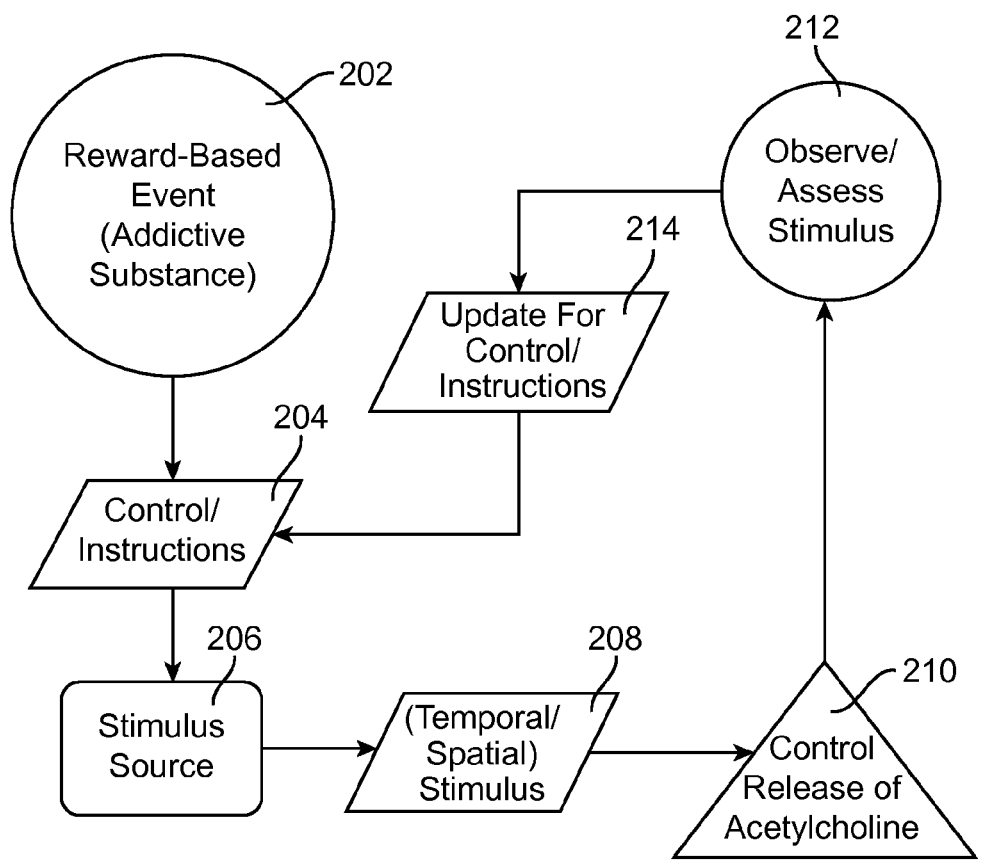
FIG. 11 depicts a flow diagram for controlling the release of acetylcholine, consistent with embodiments of the present disclosure.

FIG. 11 depicts a flow diagram for controlling the release of acetylcholine, consistent with embodiments of the present disclosure. A reward-based event 202 provides a basis for assessing or controlling reward-related behaviors and/or for reward learning. Although not, limited thereto, the reward-based event 202 can be the introduction of an addictive substance to a patient. Control instructions 204 determine how stimulus source 206 applies a stimulus 208 as a function of a target that can be defined by one or more of temporal attributes, spatial location and/or cell-type. The stimulus 208 results in changes to the release of acetylcholine 210. The effect of the stimulus can then be monitored 212. The monitoring can be used to adjust the control instructions, thereby fine-tuning the stimulus for the intended result. Various embodiments discussed herein provide further examples that can be used in connection with (or in addition to) such a process.

Embodiments of the present disclosure are directed towards the assessment of the addictive properties of a substance. Control and/or monitoring of the activity of cholinergic neurons in (or derived from) specially targeted neural structures can be used to predict the addictive nature of the substance. For instance, the cholinergic neurons of a nucleus accumbens can be exposed to the substance under study. The activity of cholinergic neurons of the nucleus accumbens is then monitored after exposure to the substance. This monitoring can include, but is not limited to, electrical activity (e.g., action potentials/firing) and/or the release of acetylcholine.

Consistent with other embodiments of the present disclosure, the effects of a treatment for an addictive substance can be assessed. For instance, a potential treatment can be used in connection with the exposure of cholinergic neurons of a nucleus accumbens to the substance. The activity of cholinergic neurons of the nucleus accumbens can be monitored in connection with the treatment to assess the effectiveness thereof.

According to embodiments of the present disclosure, the effects of a treatment for substance dependence is assessed by artificially inducing a substance dependency in an animal by exciting cholinergic neurons of a nucleus accumbens of an animal while teaching a conditioned response to the animal. The effects of the treatment are assessed by then applying the treatment, and monitoring the conditioned response of the patient.

Aspects of the present disclosure are directed toward embodiments of a system that includes a set of cholinergic neurons, a drug delivery device for providing drugs to the set of cholinergic neurons; and a monitoring device for assessing the activity of the set of cholinergic neurons in response to the drugs being provided to the set of cholinergic neurons. Consistent with certain embodiments, the set of cholinergic neurons include light-responsive opsins, and the system further includes an optical delivery system for exciting the cholinergic neurons by activating the light-responsive opsins.

Consistent with various embodiments of the present disclosure, control over the neural circuit can include inhibition or excitation, which can each include coordinated firing, and/or modified susceptibility to external circuit inputs. For instance, inhibition can be accomplished using a light-responsive opsin, such as an ion pump (e.g., NpHR and NpHR variants). Such ion pumps move the membrane potential of the neuron away from its threshold voltage to dissuade or inhibit action potentials. In another instance, excitation can be accomplished using a light responsive opsin, such as an ion channel (e.g., ChR2 and ChR2 variants). Such ion channels can cause the membrane potential to move toward and/or past the threshold voltage, thereby exciting or encouraging action potentials. Consistent with various embodiments, a light-responsive opsin can be used to (temporarily) shift the resting potential of a neuron to increase or decrease its susceptibility to external circuit inputs. These various options can also be used in combination.

Various embodiments of the present disclosure relate to an optogenetic system or method that correlates temporal control over a neural circuit with measurable metrics. For instance, a particular memory function might be associated with a neurological disorder. The optogenetic system targets a neural circuit within a patient for selective control thereof. The optogenetic system involves monitoring the patient for metrics (e.g., symptoms) associated with the neurological disorder. In this manner the optogenetic system can provide detailed information about the neural circuit, its function and/or the neurological disorder.

Embodiments of the present disclosure are directed toward combined solution(s) in which control over neural structures associated with reward-related behaviors and/or reward learning is used in combination with the disruption of memory acquisition and recall associated with the reward-related behavior. For instance, cocaine addiction can be studied and/or treated by inhibiting neural structures associated with reward-related behaviors and/or reward learning when the neural structures are exposed to cocaine. Moreover, memory acquisition associated with the cocaine use can be disrupted at the time that the cocaine is introduced to the patient. Memory recall associated with cocaine use can also be disrupted, e.g., in response to a trigger event associated with cocaine use. While cocaine is presented as an example, the application of such solution(s) is not so limited. Embodiments and experimental results relating to memory disruption are discussed in more detail hereafter.

Embodiments of the present disclosure are directed towards disrupting memory acquisition, recall and/or associations between memory and emotional responses, such as addiction-based or fear-based memories. In a particular embodiment, a specific neural circuit is targeted through the expression of light-responsive opsins therein. Function of the neural circuit is disrupted by activation of the expressed opsins, which can inhibit function of the neural circuit (e.g., using NpHR or NpHR variants). In other embodiments, the specific neural circuit is targeted by implanting electrode(s) near the specific neural circuit. Function of the neural circuit is disrupted through the application of an electrical signal to the electrode(s). In other embodiments, the specific neural circuit is targeted by implanting a device that delivers a fast-acting pharmaceutical near the specific neural circuit. Function of the neural circuit is disrupted through activation of the device to release the fast-acting pharmaceutical, which thereby inhibits function of the specific neural circuit.

In certain implementations, this disruption can be implemented during memory creation. In other implementations, this disruption can be implemented before or during memory recall. This can be particularly useful for psychiatric or neurological disorders involving memory recall, such as post-traumatic stress disorder (PTSD). Consistent with certain embodiments, the disruption can be triggered in response to a memory trigger event or other external stimulus that is presented and/or controlled for the disruption. For instance, the disruption can be provided in response to the introduction of a trigger for a memory to an animal/patient conditioned to respond to the trigger. In another instance, a patient can actively trigger the disruption. For instance, a patient may trigger the disruption when experiencing a memory associated with PTSD. Other embodiments of the present disclosure are directed towards encouraging memory acquisition, recall and/or associations between memory and emotional responses. For instance, an expressed opsin can be used to increase the susceptibility of a neural circuit to intrinsic stimulus (e.g., using stabilized step-function opsins (SSF0s) discussed herein). The encouragement can be provided to strengthen the acquisition, formation or recall of a memory. This can be used to ascertain the role of the circuit or to treat disorders associated with memory impairment. It has been discovered that (temporal) disruption of the dorsal CA1 hippocampus circuit is effective to prevent contextual fear memory acquisition. Consistent therewith, a prevailing neural network theory suggests that the process of memory consolidation starts with short term modifications in the connections between the hippocampus and the cortex, which enable the hippocampus to activate the relevant cortical sites that contribute to the complete memory, rather than store the memory itself. While these cortical traces are repeatedly co-activated, gradual long-lasting changes in the connections between them occur until eventually these connections are strong enough to support the memory without any hippocampal involvement. Surprisingly, it has been discovered that that disruption of the dorsal CA1 hippocampus circuit is effective to block fear-memory recall, even after cortical reorganization is believed to have occurred.

The following discussion, which includes a discussion of several experimental embodiments, presents a number of examples of these and other embodiments. These examples, however, are not meant to be limiting. One such embodiment concerns a production of a lentiviral vector. This lentiviral vector carries the gene encoding the light-activatable eNpHR3.1 that is fused in-frame to enhanced yellow fluorescent protein (eNpHR3.1-EYFP) under control of the calcium/calmodulin-dependent protein kinase IIa (CaMKIIa) promoter, selective for excitatory glutamatergic neurons. eNpHR3.1 is a truncated version of eNpHR3.0 with a deletion of the intrinsic N-terminal signal peptide, and is similar to eNpHR3.0 in both the photocurrent and the hyperpolarization it induces in neurons. Stereotactic delivery of CaMKIIa::eNpHR3.1 resulted in CA1 specific expression, covering its entire dorsal segment. Within the transfected area, 94% of the CaMKIIa cells expressed eNpHR3.1, and the promoter provided complete specificity, namely, all eNpHR3.1-EYFP cells were also CaMKIIa positive (FIG. 1B). Optrode recordings in anesthetized mice confirmed that continuous green (561 nm) light illumination of excitatory CA1 neurons strongly inhibited spiking (73% decrease) in a temporally precise and reversible manner, without affecting spike amplitude. To demonstrate that optogenetic inhibition can also block the neuronal activity induced by FC in a region-specific manner, and bilateral continuous green light was delivered via two optic fibers inserted through a double cannula targeting dorsal CA1 during training, and stained for the synaptic activation marker cFos. eNpHR3.1 expressing mice demonstrated reduced cFos expression specifically in CA1 but not in two other brain regions involved in FC, the basolateral amygdala (BLA) and the anterior cingulated cortex (ACC).

Optogenetic inhibition was shown to modulate cognitive function by administering bilateral continuous green light to freely-moving mice during training in a customized FC chamber. During training, mice were introduced into context A, and then presented twice with a tone followed by a foot-shock, under continuous bilateral light delivery. Fear memory was then assessed the next day with no light. Dorsal CA1 optogenetic inhibition during training prevented contextual fear acquisition. The effect of optogenetic inhibition was shown to be reversible by re-training the mice in the same context without light administration, and testing again on the next day. eNpHR3.1 expressing mice exhibited intact contextual memory when no light was administered during training Dorsal CA1 optogenetic inhibition was also shown to interfere with memory recall. The same mice were retested, this time with light delivery during recall, and it was found that the memory that was present the day before became unavailable for recall under illumination.

It was shown that fear acquisition and fear expression mechanisms were likely not affected through testing of the same mice in a different context for their memory of the tone. eNpHr3.1 expressing mice demonstrated intact auditory-cued fear memory acquisition following light inhibition during training, as well as intact-cued fear recall with illumination during the test. Using the correlation between spatial exploration and contextual fear acquisition, the exploration time of the conditioning chamber was measured during training under light stimulation. No significant difference was found between eNpHR3.1 expressing mice and their controls. It is believed that CA1 optogenetic inhibition does not have an anxiolytic effect as mice were tested for their open field exploration with light administration. No significant differences in path length, velocity, or the percent of time spent in the center of the field (which serves as a sign of anxiety) were found between eNpHR3.1 expressing and control mice.

To test whether optogenetic inhibition can result in different behavioral phenotypes when eNpHR is expressed in different brain structures, mice were bilaterally injected with an adeno-associated virus (AAV5) carrying CaMKIIa::eNpHR3.0-EYFP into the BLA. The acquisition of fear itself, i.e. the association between an aversive stimulus to any neutral stimulus, as well as the expression of recent and remote fear depend on the amygdala, and optogenetic activation of the BLA was sufficient to induce fear from a neutral stimulus. It was shown that optogenetic inhibition of the BLA interferes with both contextual and auditory-cued FC acquisition.

Accordingly, embodiments of the present disclosure are directed toward the introduction of third generation eNpHR in a cell-type and region specific fashion, and the use of CA1 optogenetic inhibition for interference with both acquisition and recent memory recall.

Embodiments of the present disclosure are also directed towards the use of such aspects to refine the present understanding of the role of the hippocampus in remote memory recall. Consistent with an experimental embodiment of the present disclosure, a group of mice were trained and then tested four weeks later. It was shown that CAI shutdown during recall appears to (completely) block remote fear memory. This interference with recall was also shown to be reversible, as when the mice where re-tested on the next day without illumination they appeared to express fear similarly to controls. eNpHr3.1 expressing mice demonstrated intact remote auditory-cued fear memory recall with illumination during the cued test, suggesting that their fear expression mechanism remains intact. Surprisingly, this suggests hippocampal involvement in remote fear memory.

Embodiments of the present disclosure are also directed towards the ability of CA1 inhibition (optogenetic or otherwise) to reversibly affect remote fear recall by preventing recall of long-term memories in real time, after repeated recall and reconsolidation. Experimental results were obtained by training another group of mice and then testing them five weeks later to verify the persistence of a memory trace (without light in both training and testing). Similar performance was found in both groups. On the next day, the same mice were tested under illumination, and the eNpHR3.1 group appeared to fail to recall the aversive memory. This effect was shown to be reversible, as on the next day, when tested without light delivery, eNpHR3.1 expressing mice demonstrated intact contextual memory. Moreover, after the mice had already recalled the aversive context and expressed fear, the fear response quickly ceased as soon as the light was delivered again, from the middle of the testing trial and onward.

Embodiments of the present disclosure are thereby directed toward reversible interference of remote fearful memory in real-time, even after the memory may have already been retrieved. This can be particularly useful for therapeutic treatments, e.g., in which a disturbing memory may be stopped as it appears, for example in PTSD patients, without permanently affecting other memories that are stored in the same brain structure.

The apparent direct involvement of the hippocampus in accessing remote memories, suggests a surprising finding that the intact hippocampus is still the default activator of the memory trace. Experimental tests were conducted to determine the effects of the temporal nature and/or resolution of the inhibition. The remote memory experiment was repeated with either precise illumination during the duration of the test only (as before), or prolonged light exposure, in which light was administered for 30 minutes before testing and then continuously throughout the test. Precise optogenetic inhibition significantly inhibited remote memory retrieval, whereas prolonged inhibition had no significant effect on remote memory retrieval. When the prolonged group mice were re-tested on the next day with precise light administration (during the test only), they showed inhibited fear recall. The lack of effect of prolonged light administration is not believed to be attributable to a decreased inhibition by eNpHR3.1 over time or reduction in cell health due to prolonged light exposure, as whole cell patch recordings on eNpHR3.1 positive cells in slices prepared from the same mice showed that the ability of eNpHR to suppress spiking remained the same throughout a 30 minutes period and was reversible. This data suggest that whereas the intact hippocampus is the default activator of the remote memory trace, the memory trace is not stored in the hippocampus, as when given enough time to compensate for its inactivation, the memory trace can still be retrieved by other brain structures.

Embodiments of the present disclosure are directed toward the inhibition of remote memory through inhibition of the anterior cingulated cortex (ACC). Experiments were conducted by targeting the ACC with a CaMKIIa::eNpHR3.0-EYFP virus, and testing the effect of optogenetic inhibition both one day and one month following training ACC optogenetic inhibition had no apparent effect on recent memory, but significantly impaired remote memory. Together, these findings suggest that even following cortical reorganization the most efficient way to activate the memory trace still involves the hippocampus.

The hippocampus is believed to provide continuous input to the cortex. Accordingly, an experiment was performed to determine whether the disrupted remote recall is a byproduct of the sudden drop in input from the hippocampus to the cortex, even if this input is unrelated to the recall task. Another major cortical input source, the olfactory bulbs (OB), was targeted with a CaMKIIa::eNpHR3.0-EYFP virus, and the effect of optogenetic inhibition was tested during both recent and remote fear recall. OB optogenetic inhibition had no significant effect on memory recall at either time point, suggesting that a sudden drop of otherwise unrelated excitatory input into the cortex is not sufficient to interfere with recall. When remote memories are retrieved they become available for reconsolidation, which renders them susceptible to disruption but this may also strengthen the trace. Aspects of the present disclosure relate to therapy for PTSD patients, in which a recurring disturbing memory may be stopped as it appears by reversibly shutting down a remote fearful memory in real-time, before and after reconsolidation, or in real-time after it has already been retrieved.

Consistent with another embodiment of the present disclosure, memories related to drugs of abuse can be inhibited to reduce drug seeking behavior. Other embodiments are directed toward the ability to instantaneously affect cognition by optogenetic modulation of different brain areas in order to study the role of specific neuronal populations in memory processes and enable a finer temporal, genetic and spatial dissection of the neuronal circuits that underlie them.

Specific aspects of the present invention relate to memory switching using microbial opsin genes adapted for neuroscience, allowing transduction of light pulse trains into millisecond-timescale membrane potential changes in specific cell types within the intact mammalian brain (e.g., channelrhodopsin (ChR2), *Volvox* channelrhodopsin (VChR1) and halorhodopsin (NpHR)). ChR2 is a rhodopsin derived from the unicellular green alga *Chlamydomonas reinhardtii*. The term "rhodopsin" as used herein is a protein that comprises at least two building blocks, an opsin protein, and a covalently bound cofactor, usually retinal (retinaldehyde). The rhodopsin ChR2 is derived from the opsin Channelopsin-2 (Chop2), originally named Chlamyopsin-4 (Cop4) in the *Chlamydomonas* genome. The temporal properties of one depolarizing channelrhodopsin, ChR2, include fast kinetics of activation and deactivation, affording generation of precisely timed action potential trains.

For applications seeking long timescale activation, it has been discovered that the normally fast off-kinetics of the channelrhodopsins can be slowed. For example, certain implementations of channelrhodopsins apply 1 mW/mm$^2$ light for virtually the entire time in which depolarization is desired, which can be less than desirable. Much of the discussion herein is directed to ChR2. Unless otherwise stated, the 30 invention includes a number of similar variants. Examples include, but are not limited to, Chop2, ChR2-310, Chop2-310, and *Volvox* channelrhodopsin (VChR1. For further details on VChR1 reference can be made to "Red-shifted optogenetic excitation: a tool for fast neural control derived from *Volvox carteri*," *Nat. Neurosci.* June 2008, 11(6):631-3. Epub 2008 Apr. 23, which is fully incorporated herein by reference. In other implementations, similar modifications can be made to other opsin molecules. For instance, modifications/mutations can be made to ChR2 or VChR1 variants. Moreover the modified variants can be used in combination with light-activated ion pumps.

Embodiments of the present invention include relatively minor amino acid variants of the naturally occurring sequences. In one instance, the variants are greater than about 75% homologous to the protein sequence of the naturally occurring sequences. In other variants, the homology is greater than about 80%. Yet other variants have homology greater than about 85%, greater than 90%, or even as high as about 93% to about 95% or about 98%. Homology in this context means sequence similarity or identity, with identity being preferred. This homology can be determined using standard techniques known in the field of sequence analysis. The compositions of embodiments of the present invention include the protein and nucleic acid sequences provided herein, including variants which are more than about 50% homologous to the provided sequence, more than about 55% homologous to the provided sequence, more than about 60% homologous to the provided sequence, more than about 65% homologous to the provided sequence, more than about 70% homologous to the provided sequence, more than about 75% homologous to the provided sequence, more than about 80% homologous to the provided sequence, more than about 85% homologous to the provided sequence, more than about 90% homologous to the provided sequence, or more than about 95% homologous to the provided sequence.

As used herein, stimulation of a target cell is generally used to describe modification of properties of the cell. For instance, the stimulus of a target cell may result in a change in the properties of the cell membrane that can lead to the depolarization or polarization of the target cell. In a particular instance, the target cell is a neuron and the stimulus affects the transmission of impulses by facilitating or inhibiting the generation of impulses (action potentials) by the neuron.

For further details on light-responsive opsins, reference can be made to PCT publication No. WO 2010/056970, entitled "Optically-Based Stimulation of Target Cells and Modifications Thereto," to Deisseroth et al., which is fully incorporated herein by reference.

Embodiments of the present disclosure are directed towards implementation of bistable changes in excitability of targeted populations. This includes, but is not necessarily limited to, the double-mutant ChR2-C128S/D156A. This double-mutant ChR2-C128S/D156A has been found to be well-tolerated in cultured hippocampal neurons and preserved the essential SFO properties of rapid step-like activation with single brief pulses of blue light, and deactivation with green or yellow light. In particular, the activation spectrum of ChR2-C128S/D156A peaks at 445 nm. A second deactivation peak was found at 390-400 nm, with faster but less complete deactivation by comparison with the 590 nm deactivation peak. Peak photocurrents in cells expressing ChR2—C128S/D156A were found to be robust, and comparable to those of ChR2-D156A (231.08±31.19 s.e.m; n=9 cells and 320.96±78.26 s.e.m; n=7 cells, respectively).

Individual transfected and patch-clamped neurons were next activated with 100 ms pulses of 470 nm light, and to ensure over very long recordings that current decay would not be attributable to cell rundown, each cell was deactivated with prolonged 590 nm light pulses at distinct intervals to determine the magnitude of remaining SFO current at each time point. Surprisingly, neurons expressing ChR2—C128S/D156A gave rise to sustained photocurrents that were more stable than those from cells expressing either single mutant alone. Fitting a mono-exponential decay curve to the ratio of Ideactivation/Iactivation over time revealed a spontaneous decay time constant of 29 3 min for ChR2-C128S/D156A, indicating that the C 128 and D156 mutations act synergistically to delay the decay of the open state of ChR2.

Consistent with the required improvement for the anticipated application to complex mammalian behaviors, significant portions of the double-mutant SFO current were still present up to 20 minutes after the single photoactivation pulse. Based on these surprisingly slow decay kinetics, the double-mutant gene is referred to as SSFO (for stabilized step-function opsin) gene. SSFO is also used as shorthand for the active protein. Both residues likely are involved in ChR2 channel closure (gating), and both mutations likely stabilize the open state configuration of the channel. Without being limited by theory, aspects of the present disclosure relate to the discovery that SSFO may be completely blocked in photocycle progression, and may therefore represent the maximal stability possible with photocycle engineering. For instance, in contrast to ChR2-C128X and ChR2-D156A, the SSFO photocycle does not appear to access additional inactive deprotonated side products which likely split off the photocycle at later photocycle stages not reached in this mutant, in turn making the SSFO even more reliable for repeated use in vivo than the parental single mutations.

Embodiments of the present disclosure are directed toward the sensitivity of the SSFO to light. For instance, channelrhodopsins with slow decay constants effectively act as photon integrators. This can be particularly useful for more-sensitive, less-invasive approaches to optogenetic circuit modulation, still with readily titratable action on the target neuronal population via modulation of light pulse length. It has been discovered that, even at extraordinarily low light intensities (as low as 8 $pW/mm^2$), hundreds of picoamps of whole-cell photocurrents could be obtained from neurons expressing SSFO, which increased with monoexponential kinetics in response to 470 nm light during the entire time of illumination. Other aspects relate to the use of activation time constants that are linearly correlated with the activation light power on a log-log scale, which is indicative of a power-law relationship and suggesting that the SSFO is a pure integrator, with total photon exposure over time as the only determinant of photocurrent. For instance, it is believed that the number of photons per membrane area required for photocurrents to reach a given sub-maximal activation (time to T) is constant regardless of activation light power.

Example embodiments of the present disclosure relate to the use of a hybrid ChR1/VChR1 chimera contains no ChR2 sequence at all, is derived from two opsins genes that do not express well individually, and is herein referred to as C1V 1. Embodiments of the present disclosure also relate to improvements of the membrane targeting of VChR1 through the addition of a membrane trafficking signal derived from the $K_{ir}2.1$ channel Confocal images from cultured neurons expressing VChR1-EYFP revealed a large proportion of intracellular protein compared with ChR2; therefore, to improve the membrane targeting of VChR1, we added a membrane trafficking signal derived from the $K_{ir}2.1$ channel. Membrane targeting of this VChR1-is-EYFP was slightly enhanced compared with VChR1-EYFP; however, mean photocurrents recorded from cultured hippocampal neurons expressing VChR1ts-EYFP were only slightly larger than those of VChR1-EYFP. Accordingly, embodiments of the present disclosure relate VChR1 modified by exchanging helices with corresponding helices from other ChRs. For example, robust improvement has been discovered in two chimeras where helices 1 and 2 were replaced with the homologous segments from ChR1. It was discovered that whether splice sites were in the intracellular loop between helices 2 and 3 (at ChR1 residue Ala145) or within helix 3 (at ChR1 residue Trp163), the resulting chimeras were both robustly expressed and showed similarly enhanced photocurrent and spectral properties. This result was unexpected as ChR1 is only weakly expressed and poorly integrated into membranes of most mammalian host cells. The resulting hybrid ChR1/VChR1 chimera is herein referred to as C1V1.

Aspects of the present disclosure relate to the expression of C1V1 in cultured hippocampal neurons. Experimental tests have shown a number of surprising and useful results, which are discussed in more detail hereafter. C1V 1-EYFP exhibits surprisingly improved average fluorescence compared with VChR1-EYFP. Whole cell photocurrents in neurons expressing C1V1 were much larger than those of VChR1-EYFP and VChR1-ts-EYFP, and ionic selectivity was similar to that of ChR2 and VChR1. The addition of the Kir2.1 trafficking signal between C1V1 and YFP further enhanced photocurrents by an additional 41% (C1V1-tsEYFP mean photocurrents were extremely large, nearly tenfold greater than wild type (WT) VChR1). Mean fluorescence levels closely matched the measured photocurrents (mean fluorescence 9.3±1, 19.6±3.4, 19.8±2.8 and 36.3±3.8 for VChR1-EYFP, VChR1-ts-EYFP, C1V1-EYFP and C1V1-ts-EYFP, respectively), suggesting that the increase in photocurrent sizes resulted mainly from the improved expression of these channels in mammalian neurons. Total somatic fluorescence (measured as integrated pixel density) was linearly correlated with photocurrent size in individual recorded/imaged cells across the different constructs (VChR1, VChR1-ts-EYFP, C1V1, C1V1-ts-EYFP). This suggests (without being limited by theory) that the increased photocurrent of C1V1 results from functional expression changes in neurons.

Various embodiments of the present disclosure relate to opsins with fast decay constants. This property can be particularly useful for providing precise control over spiking, e.g., in order to interfere minimally with intrinsic conductances, trigger single spikes per light pulse and/or minimize plateau potentials during light pulse trains. Experimental results suggest that the light-evoked photocurrents recorded in C1V1-ts-EYFP decayed with a time constant similar to that of VChR1. Aspects of the present disclosure are therefore directed toward modifications in the chromophore region to improve photocycle kinetics, reduced inactivation and/or possible further red-shifted absorption.

One embodiment is directed toward a corresponding ChETA mutation E162T, which experiments suggest provides an accelerated photocycle (e.g., almost 3-fold), (reference can be made to Gunaydin, et al., Ultrafast optogenetic control, *Nat Neurosci,* 2010, and which is fully incorporated herein by reference). Surprisingly, this mutation was shown to shift the action spectrum hypsochromic to 530 nm, whereas analogous mutations in ChR2 or other microbial rhodopsins have caused a red-shift.

Another embodiment is directed toward a mutation of glutamate-122 to threonine (C1V1-E122T). Experimental tests showed that C1V1-E122T is inactivated only by 26% compared to 46% inactivation of ChR2; in addition, the spectrum was further red-shifted to 546 nm.

Another embodiment of the present disclosure is directed toward a double mutant of C1V1 including both E122T and E162T mutations. Experimental tests have shown that the inactivation of the current was even lower than in the E122T mutant and the photocycle was faster compared to E162T. This suggests that multiple useful properties of the individual mutations were conserved together in the double mutant.

Embodiments of the present disclosure include the expression of various light-responsive opsins in neurons. Experimental tests of C1V1 opsin genes in neurons were carried out by generating lentiviral vectors encoding C1V1-ts-EYFP and various point mutation combinations discussed herein. The opsins were then expressed in cultured hippocampal neurons and recorded whole-cell photocurrents under identical stimulation conditions (2 ms pulses, 542 nm light, 5.5 mW/mm$^2$) Photocurrents in cells expressing C1V1, C1V1-E162T and C1V1-E122T/E162T were all robust and trended larger than photocurrents of ChR2-H134R. The experiments also included a comparison of integrated somatic YFP fluorescence and photocurrents from cells expressing C1V1-E122T/E162T and from cells expressing ChR2H134R. Surprisingly, C1V1-E122T/E162T cells showed stronger photocurrents than ChR2H134R cells at equivalent fluorescence levels. This suggests that C1V1 could possess a higher unitary conductance compared with ChR2-H134R. The test results suggest that the kinetics of C1V1-E122T were slower than those of C1V1-E122T/E162T and that cells expressing C1V1-E122T responded more strongly to red light (630 nm) than cells expressing the double mutant. This can be particularly useful for generating optogenetic spiking in response to red-light.

Consistent with various embodiments of the present disclosure, inhibitory and/or excitatory neurons residing within the same microcircuit are be targeted with the introduction of various opsins. Experimental tests were performed by separately expressed C1V1-E122T/E162T and ChR2-H134R under the CaMKIIa promoter in cultured hippocampal neurons. Cells expressing C1V1-E122T/E162T spiked in response to 2 ms green light pulses (560 nm) but not violet light pulses (405 nm). In contrast, cells expressing ChR2-H134R spiked in response to 2 ms 405 nm light pulses, but not 2 ms 561 nm light pulses.

Various embodiments of the present disclosure relate to independent activation of two neuronal populations within living brain slices. Experimental tests were performed by CaMKIIa-C1V1-E122T/E162Tts-eYFP and EFla-DIO-ChR2-H134R-EYFP in mPFC of PV::Cre mice. In non-expressing PYR cells, 405 nm light pulses triggered robust and fast inhibitory postsynaptic currents (IPSCS) due to direct activation of PV cells, while 561 nm light pulses triggered only the expected long-latency polysynaptic IPSCs arising from C1V1-expressing pyramidal cell drive of local inhibitory neurons.

Various embodiments described above or shown in the figures may be implemented together and/or in other manners. One or more of the items depicted in the drawings/figures can also be implemented in a more separated or integrated manner, or removed and/or rendered as inoperable in certain cases, as is useful in accordance with particular applications. In view of the description herein, those skilled in the art will recognize that many changes may be made thereto without departing from the spirit and scope of the present invention.

EXAMPLES

Neurons employing the neurotransmitter acetylcholine are widespread but relatively rare, with cell bodies and projections sparsely distributed throughout much of the mammalian brain. Pharmacological modulation of the various acetylcholine receptors is known to affect numerous brain processes, but often with side effects due to limitations in drug specificity for receptor type and target cell population, such that the ultimate causal role of cholinergic neurons in circuit function and behavior has been unclear. In a paradigmatic case, the giant cholinergic interneurons of the nucleus accumbens (NAc) are a structurally distinctive and sparsely distributed group of neurons whose function has remained elusive due to experimental inability to precisely activate or inactivate these cells in living tissue or in behaving animals. Here we integrate several optical control technologies, in the setting of freely moving mammalian behavior, in vivo electrophysiology, and slice physiology, to causally probe the function of these neurons by direct excitation or inhibition with high cellular and temporal precision. Remarkably, despite representing a tiny (<1%) fraction of the local neuronal population, we found that the cholinergic neurons in the NAc have a dominant control role, exerting powerful, bidirectional modulation of activity in the surrounding circuit. Furthermore, we found that these neurons were directly activated by cocaine, and that silencing this drug-induced activity during cocaine exposure in freely behaving mammals disrupted cocaine reward. Importantly, manipulation of the cholinergic interneurons was not aversive by itself, suggesting that these unique cells play a role in specifically implementing hedonic behaviors relevant to drugs of abuse via their potent influence on the NAc circuitry.

Acetylcholine is an important and widely-studied neurotransmitter, which acts upon an enormous diversity of receptors and target cells (1-8). Pioneering pharmacological and genetic studies have elucidated the complex and often opposing influences of the individual subtypes of muscarinic and nicotinic acetylcholine receptors on numerous biological processes (9-15), but no study has yet resolved the fundamentally distinct question of the causal role of cholinergic neurons themselves within a CNS tissue, despite the hypothesized importance of these neurons in learning, memory, attention, and reward (16-22). Addressing such a question would require a novel paradigm for selective and temporally precise control (activation and inhibition) of cholinergic neurons within living mammalian tissues, since previous investigations have resulted in contradictory findings likely due to challenges with specificity and temporal resolution. For example, elegant in vivo pharmacological approaches have reported (23-26) that cholinergic transmission in the NAc (a structure involved in natural reward-related behaviors and responses to drugs such as cocaine (27-33)) is required for reward learning, but novel studies of molecular ablation of cholinergic interneurons within the NAc instead have reported enhanced reward learning (34). These cholinergic interneurons within the NAc are particularly intriguing as they constitute less than 1% of the local neural population (35), yet project throughout the NAc and provide its only known cholinergic input (36, 37). Relevant cholinergic receptors are expressed locally, and nicotinic and muscarinic pharmacological agonists can exert complex influences on medium spiny neurons (MSNs, which represent >95% of the local neuronal population and constitute the output of the NAc) (38-41), but the net effect (if any) of the extremely rare cholinergic interneurons on any aspect of NAc physiology or behavior is, as with other brain regions, unknown.

Example 1

Expression of Light-Responsive Opsin Proteins in Cholinergic Interneurons of the Nucleus Accumbens We undertook an optogenetic approach (42-44) to resolve this question by selectively driving or blocking action potential firing in these cells, with both high temporal resolution and high cell-type specificity. To express microbial opsin genes specifically in cholinergic interneurons, we employed a transgenic mouse line expressing Cre recombinase under the choline acetyltransferase (ChAT) promoter (45). We stereotaxically injected into the NAc (FIG. 1A) a Cre-inducible adeno-associated virus (AAV) vector carrying the opsin gene fused in-frame with coding sequence for enhanced yellow fluorescent protein (eYFP) (46, 47); the opsin gene encoded either the blue-light gated cation channel channelrhodopsin-2 (ChR2) (48, 49) or the yellow-light gated third-generation chloride pump halorhodopsin (eNpHR3.0) (50).

Materials and Methods

Subjects

BAC transgenic Choline Acetyltransferase (ChAT)::Cre mice were obtained from GENSAT (stock name: Tg(Chat-cre) 24Gsat/Mmcd) (Gong et al., *J. Neurosci* 27, 9817-9823 (2007)) and mated with C57BL6 mice from Charles River. Experimental mice were either heterozygous for Cre (+/−) or else control littermates (−/−). Mice were group housed in a colony maintained on a reversed 12 hr light/dark cycle and given food and water ad libitum. Experimental protocols were approved by Stanford University IACUC to meet guidelines of the National Institutes of Health guide for the Care and Use of Laboratory Animals.

Virus Production

As described previously (Tsai et al., *Science* 324, 1080-1084 (2009); Sohal et al., *Nature* 459, 698-702 (2009)), Cre-inducible recombinant AAV vectors were based on a DNA cassette carrying two pairs of incompatible lox sites (loxP and lox2722) with the opsin (either ChR2(H134R) or eNpHR3.0) inserted between the lox sites in the reverse orientation. This double-floxed reverse opsin cassette was cloned into a version of the pAAV2-MCS vector carrying the EF-1α promoter and the Woodchuck hepatitis virus post-transcriptional regulatory element (WPRE) to enhance expression. Full maps of the Cre-inducible ChR2 AAV construct, as well as the eNpHR3.0 transgene, are available at www.stanford.edu/group/dlab/optogenetics/sequence_info.html. The recombinant AAV vectors were serotyped with AAV5 coat proteins and packaged by the viral vector core at the University of North Carolina. The final viral concentration was $3 \times 10^{12}$ particles/mL for the ChR2 virus and $1.5 \times 10^{12}$ particles/mL for the eNpHR3.0 virus.

Stereotactic Virus Injection, Cannula/Patchcord Implantation, and Light Delivery Mice were anesthetized with ketamine/xylazine (60 µl/mouse of a mixture of 80 mg/ml ketamine and 12 mg/ml xylazine), and then placed in a stereotactic head apparatus. Surgeries were performed on 4-6 week old mice for physiology experiments and 8-12 week old mice for behavior experiments. Ophthalmic ointment was applied to prevent the eyes from drying. A midline scalp incision was made followed by a craniotomy, and then virus was injected with a 10 µl syringe and a 34 gauge metal needle. The injection volume and flow rate (1 µl at 0.15 µl/min) were controlled by an injection pump. Each NAc received two injections (injection 1: AP 1.15 mm, ML 0.8 mm, DV −4.8 mm;

injection 2: AP 1.15 mm, ML 0.8 mm, DV −4.2 mm). The virus injection and fiber position were chosen so that virtually the entire shell was stimulated. Given the small size of the shell in mice, it is not possible to limit the virus spread and the light entirely to the medial shell, and the medial part of the core was included (medial to the anterior commissure). After injection the needle was left in place for 5 additional minutes and then very slowly withdrawn. For behavioral experiments mice were injected bilaterally, and then bilateral cannulas with a center-to-center distance of 1.5 mm were placed above the injection sites (AP 1.15 mm, DV 3.8 mm). To manipulate neuronal activity during behavior, light was bilaterally delivered through two 300 μm diameter optic fibers (0.37 N.A.) that were inserted through the cannulae to allow the fiber to project 200-300 μm past the end of the cannulae.

Immunohistochemistry

To determine the specificity of opsin expression in ChAT neurons, mice were anesthetized with beuthanasia and perfused transcardially, first with PBS and then with 4% paraformaldehyde (PFA) dissolved in phosphate-buffered saline (PBS, pH 7.4). The brains were removed and post-fixed in 4% PFA overnight at 4° C., and then equilibrated in 30% sucrose in PBS. 40 μm-thick coronal sections were prepared on a freezing microtome (Leica) and stored in cryoprotectant (25% glycerol and 30% ethylene glycol in PBS) at 4° C. Free-floating sections were washed in PBS and then incubated for 30 min in 0.3% Triton X-100 (Tx100) and 3% normal donkey serum (NDS). Slices were incubated at 4° C. overnight with primary antibody in 3% NDS (Goat anti-ChAT 1:200, Millipore). Sections were then washed with PBS and incubated for 2 hr at room temperature with secondary antibodies (Donkey anti-goat conjugated to Cy3 or Cy5, Jackson Laboratories). Slices were then washed, incubated with DAPI (1:50,000) for 20 min, washed again, and mounted on slides with PVA-DABCO. Confocal fluorescence images were acquired on a scanning laser microscope using 5× or 10× air objectives, or a 40× oil immersion objective Results We validated the specificity and functionality of this targeting strategy in vivo, and found that eYFP expression was highly specific to neurons that expressed ChAT; moreover, the vast majority of neurons that expressed ChAT also expressed eYFP (FIG. 1B,C). The observed specificity was particularly impressive for such a sparse neural population, as there was a very low pre-test probability that any given cell would be a ChAT interneuron and therefore even rare targeting leak would dramatically decrease effective targeting specificity. Both opsins were expressed on the surface membranes of ChAT neurons (FIG. 1 D), and the targeted neurons responded to current injection in a manner corresponding to previously established responses of cholinergic interneurons in dorsal striatum (FIG. 1E) (51). In further agreement with dorsal striatum physiology, both the resting potential and input resistance were higher for ChAT neurons (YFP+neurons) than MSNs (identified as YFP-neurons; Table S1; p<$10^{-4}$ for $V_M$ and p=0.004 for Rinput, two-tailed t-test). Finally, both opsins were potently functional in ChAT cells, as eNpHR3.0 drove massive hyperpolarizations (FIG. 1F; mean±s.e.m.: −83.8±11.9 mV, n=4) and ChR2 reliably drove spiking up to 20-30 Hz (FIG. 1G, H).

TABLE 3

Membrane voltage (VM) and input resistance (RINPUT) in brain slices of ChAT neurons expressing ChR2-eYFP and of MSNs that did not express a fluorophore. Both VM and RINPUT are higher for ChAT neurons than MSNs. (p = 0.00003 for VM; p = 0.002 for RINPUT; two-tailed t-test; mean ± S.E.M.)

| ChAT (ChR2-eYFP) (n = 19) | | MSN (n = 13) | |
|---|---|---|---|
| $V_M$ (mV) | $R_{INPUT}$ (MΩ) | $V_M$ (mV) | $R_{INPUT}$ (MΩ) |
| −49.47 ± 1.07 | 382.02 ± 47.30 | −65.43 ± 2.88 | 223.64 ± 31.92 |

Example 2

Effects of Depolarization of Choline Acetyltransferase (ChAT) Interneurons

ChAT interneurons are thought to be tonically active in vivo (3-10 Hz (52, 53)), but it has remained mysterious how (or even if) this kind of slow activity in the sparse ChAT cells could be causally involved in affecting local circuit activity or behavior. We capitalized on optogenetic control to address this question with a combination of slice electrophysiology, in vivo electrophysiology, and freely-moving behavior.

Materials and Methods

Acute Brain Slice Physiology

Coronal cerebral brain slices were prepared from adult mice with virus previously injected (>2 weeks prior to slicing), using standard techniques in strict accordance with a protocol approved by the Animal Care and Use Committee at Stanford University. Coronal slices 250 μm thick were cut with a vibratome using a sapphire blade in ice cold N-methyl-D-glucamine (NMDG)-based cutting solution containing 135 mM NMDG, 1 mM KCl, 1.2 mM $KH_2PO_4$, 20 mM choline bicarbonate, 10 mM glucose, 1.5 mM $MgCl_2$ and 0.5 mM $CaCl_2$. Slices were maintained thereafter in artificial cerebral spinal fluid (ACSF) containing 119 mM NaCl, 2.5 mM KCl, 2.5 mM $CaCl_2$, 1.3 mM $MgCl_2$, 1 mM $NaH_2PO_4$, 26.2 mM $NaHCO_3$ and 11 mM glucose. Slices were maintained in ACSF at 37° C. for 30 minutes, and thereafter at room temperature. ACSF was bubbled constantly with 95% $O_2$/5% $CO_2$ and heated to 34° C. for all experiments. Neurons were visualized on an upright microscope (Leica DM-LFSA) equipped with both DIC optics and a filter set for visualizing eYFP using a ×40 water-immersion objective and a charge-coupled device (CCD) camera. Whole-cell recordings were made from neurons using the electrode solution containing 120 mM potassium gluconate, 20 mM HEPES, 10 mM EGTA, 1 mM $MgCl_2$, 2 mM Na-ATP, and 0.2 mM Na-GTP (pH 7.3, 290 mOsm/L); in experiments recording IPSCs, KCl was used to replace potassium gluconate. Pipette resistances were 3-5 MΩ, and recordings were made without series resistance compensation. Membrane potentials have been corrected for the error resulting from the liquid junction potentials. The holding potential (VM) for voltage-clamp experiments was −70 mV. The following agents were added as indicated: 5 μM SR-95531; 5 μM 2,3-dihydroxy-6-nitro-7-sulphamoyl-benzo(F) quinoxaline (NBQX); 5 μM (R,S)-CPP; mecamylamine (10 μM); 5 μM cocaine hydrochloride. The cocaine concentration of 5 μM was carefully chosen by several criteria. First, it was consistent with the choices in previous slice work (Thompson et al., *Neuropharmacology* 49, 185-194 (2005)). Second, significantly higher concentrations would result in local anesthetic effects (Thompson et al.,

*Neuropharmacology* 49, 185-194 (2005)). Finally, according to studies of cocaine pharmacokinetics in mice, an i.p. injection of 10 mg/kg will yield 4.7 µM of cocaine in the brain after 15 minutes, and 20 mg/kg will yield 9.4 µM, comparable to the levels used in behavioral experiments (Shah et al., *Toxicology and Applied Pharmacology* 53, 279-284 (1980)). Photocurrents were evoked using an optical switch with a 300W xenon lamp and either a 470±20 nm or a 580±20 nm bandpass filters; light power at the specimen was 11.52 mW mm$^{-2}$ (470 nm) or 10.64 mW mm$^{-2}$ (580 nm). Currents filtered at 2 kHz, digitized at 50 kHz, and recorded to disk using pClamp10 software (Axon Instruments). Data are expressed as mean±standard error of the mean, and statistical significance was determined using the paired or unpaired t-test, as appropriate. For IPSC measurements in MSNs (FIG. 2B-E and FIG. 5A-B), 10 repetitions without light preceded 10 repetitions with light. Each repetition was 5 seconds in length and separated by a 5 second rest period. For testing the cocaine response of ChAT cells in slice (FIG. 4A-C), whole-cell recordings were obtained from the ventral portion of the medial shell, where elevations in spiking were variable as summarized in FIG. 4, but contrasted with typical rundown of spiking in control conditions; exploratory work suggested that ChAT cells in the core and elsewhere in the shell were less responsive to cocaine.

In Vitro Optrode Recordings

Simultaneous optical stimulation and extracellular electrical recording were performed as described previously (Gradinaru et al., *J. Neurosci* 27, 14231-14238 (2007)). Optrodes consisted of a tungsten electrode (1 MΩ; 0.005 in; parylene insulation) glued to an optical fiber (300 µm core diameter, 0.37 N.A.), with the tip of the electrode projecting beyond the fiber by 300-500 µm. The electrode was lowered through the NAc in approximately 100 µm increments, and optical responses were recorded at each increment. The optical fiber was coupled to a 473 nm or 560 nm laser. The power density was ~140 mW/mm$^2$ at the fiber tip for both wavelengths, which corresponds to a density at the tip of the electrode of about ~7-17 mW/mm$^2$ for 470 nm light and ~10-22 mW/mm$^2$ for 560 nm light. Signals were amplified and band-pass filtered (300 Hz low cut-off, 10 kHz high cut-off) before digitizing and recording to disk. At each site, 5 stimulation repetitions were presented and saved. Each stimulation epoch lasted 10-15 seconds with a recovery period of 80-90 seconds between the onset time of each repetition, and 50 seconds of data were recorded to disk for each repetition.

Results

Figure 5A:
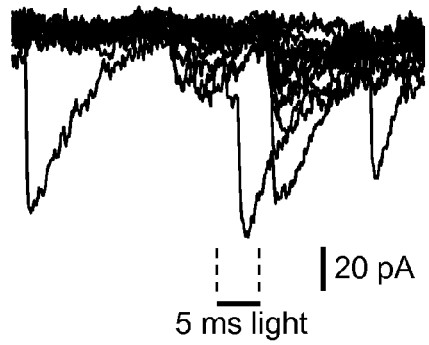
FIG. 5 depicts optogenetic photoactivation of ChAT interneurons in slice and in vivo. (A): Overlay of 15 current traces for the same MSN as in FIG. 2B, with each trace aligned to the light pulse. Some IPSCs are not time locked to the light pulses, whereas many are time locked with latency of ~8 ms after light pulse onset. (B): IPSC occurrence as a function of time relative to light pulse for the same neuron. Open bars correspond to the number of IPSCs recorded during light stimulation; grey bars correspond to the number of IPSCs recorded during baseline (before light stimulation) using the same temporal alignment. For this neuron, an asynchronous enhancement in IPSC frequency is evident, in addition to the more prominent synchronous increase. (C): A resealed presentation of FIG. 2D, displaying population-averaged percentage increase in IPSC frequency as a function of time relative to light pulses during the light on relative to light-off period (n=6). Across the population, an asynchronous enhancement in IPSC frequency is evident, in addition to the more prominent synchronous increase. Pulse parameters for panels A-C: 470 nm, 5 ms pulse duration, 10 Hz. (D): Voltage traces from in vivo recordings showing population spikes (presumably generated by ChAT cells expressing ChR2) that track pulsed blue light stimulation at 10 Hz (top) but not 100 Hz (bottom; 470 nm light; 10 sec total stimulation duration).
Figure 5B:
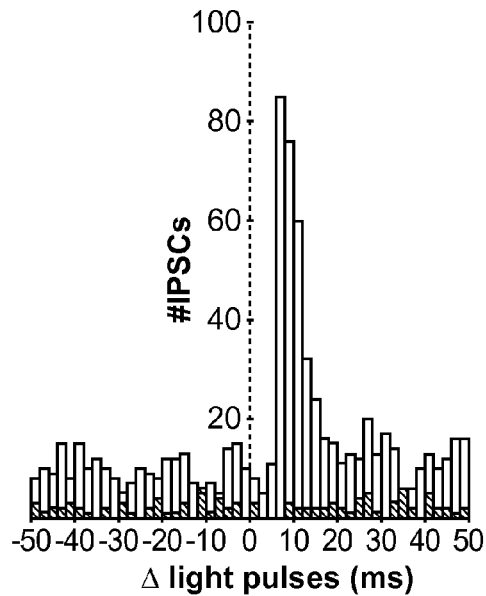
Figure 5C:
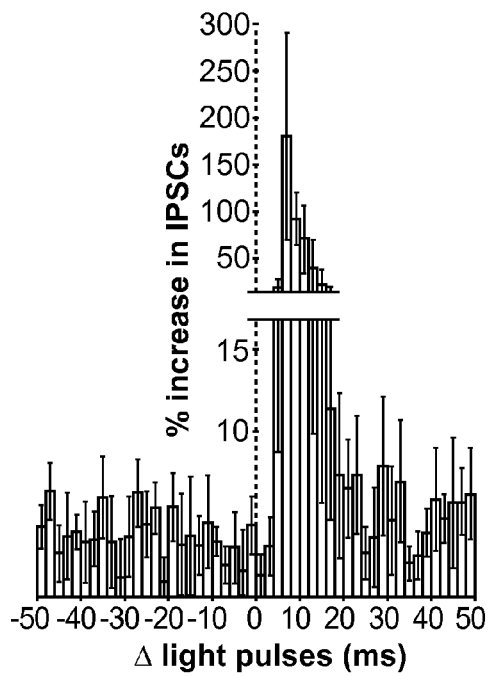
Figures 7A, 7B:
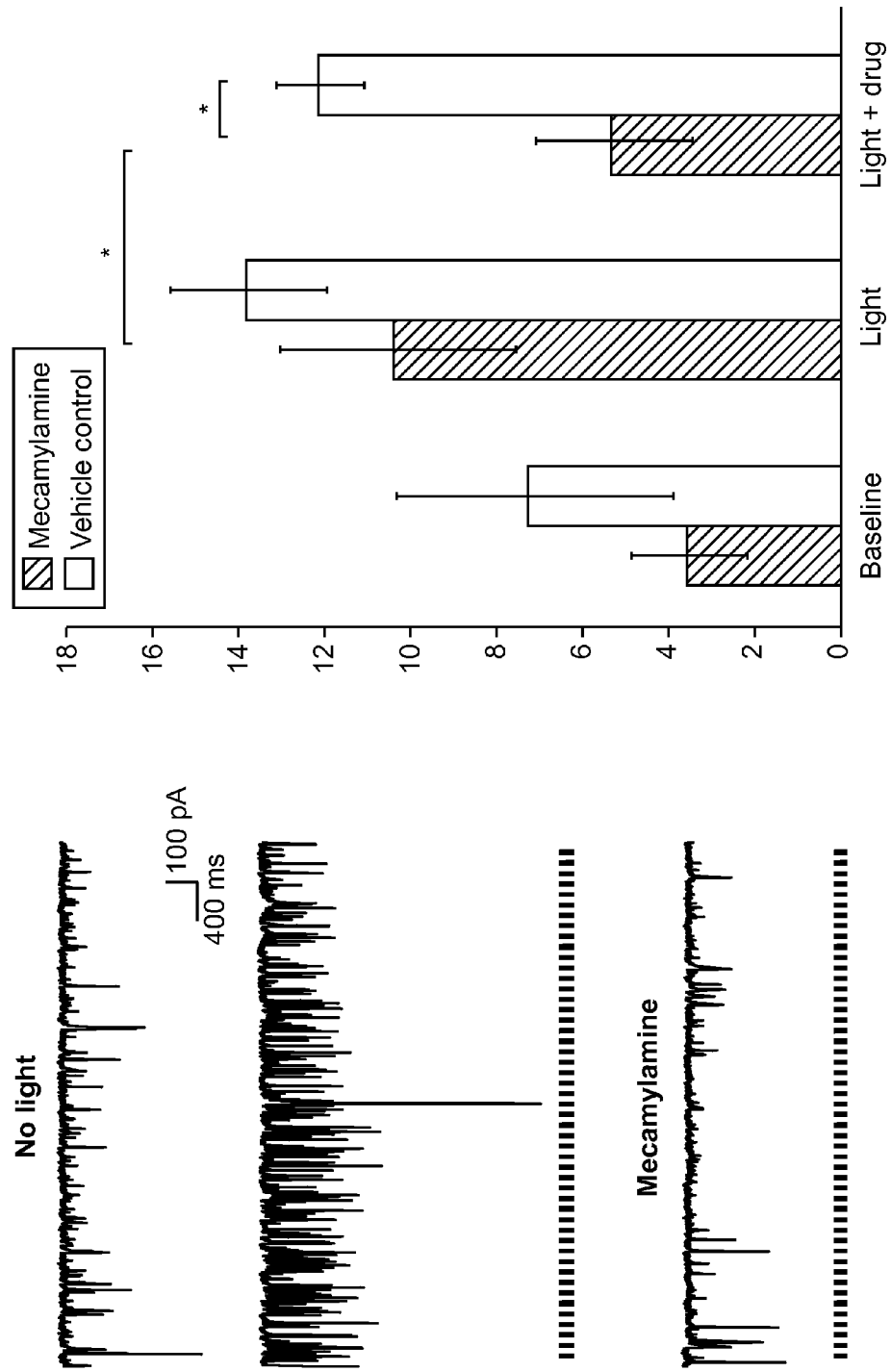
FIG. 7 depicts nicotinic receptor antagonism decreases ChAT interneuron-evoked IPSCs recorded in MSNs. (A): Representative IPSC sweeps from a typical MSN in the acute slice preparation under the conditions of no light, light pulses (470 nm, 10 Hz, 5 ms pulse width), and identical light pulses with 10 µM mecamylamine. (B): Summary graph of IPSCs recorded as in A from a population of MSNS before light presentation, with light presentation, and with light and either mecamylamine or vehicle. Light stably increased IPSC frequency from 3.4+/−1.3 Hz to 10.1+/−1.2 Hz (p<0.05; n=7, paired t-test), while mecamylamine reduced this increase to 5.1+/−1.8 Hz (p<0.05 compared to light-alone within the same cells, paired t-test; p<0.05 compared to the vehicle control, n=5, unpaired t-test).

First, postsynaptic currents in MSNs were monitored (ChR2-eYFP non-expressing cells) in acute NAc slices during optogenetic photostimulation of ChAT cells expressing ChR2-eYFP (FIG. 2A), targeted as in FIG. 1. Stimulating ChAT neurons in this setting robustly increased the frequency of γ-aminobutyric acid type A (GABA$_A$) receptor-mediated inhibitory postsynaptic currents (IPSCs) recorded in MSNs (FIGS. 2, B and C). Evoked inhibitory currents were generally synchronized to the light pulse, with a modal latency of 6 ms (FIG. 2D), coupled with a smaller enhancement of asynchronous IPSCs (FIG. 5A-C). Across all recorded cells, the mean frequency of IPSCs observed in the MSNs increased by 525.8±154.3% during light stimulation of the ChAT neurons (n=7; mean±SEM, P=0.01, paired t test), whereas the mean IPSC amplitude was unaffected (P>0.05, paired t test; n=7, FIG. 2E). This effect was attenuated by the nicotinic antagonist mecamylamine (FIG. 7, n=5, P<0.05, paired t test).

Figure 5D:
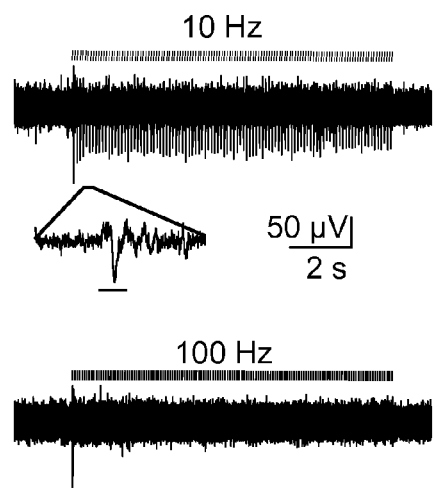

Next it was asked if and how these dramatic changes in inhibitory current frequency would translate into changes in MSN spiking in vivo. We recorded neural activity extracellularly with an optrode in the NAc during optogenetic activation of the ChAT interneurons in vivo (FIG. 2F). At sites where single units were not isolated, we observed neural population firing that tracked the light stimulation at 10 Hz but not 100 Hz (FIG. 5D), likely representing population spiking across the sparse but synchronously activated ChAT cells in the neighborhood of the electrode. In contrast to these population spikes, the isolated units in the NAc displayed a markedly different response to the optogenetic photostimulation. In agreement with the observed increase in IPSC frequency in MSNs in slices, we observed in vivo a proud inhibition of background firing during stimulation of the ChAT cells in vivo (representative cell, FIG. 2G). Across the population, most significantly modulated sites showed a suppression of background firing, although a few responded with an increase in firing (FIGS. 2, H and I), consistent with known recurrent inhibition among MSNs and corresponding release from inhibition, during ChAT neuron drive, that had been previously exerted by the broader MSN population.

Example 3

Effects of Hyperpolarization of Choline Acetyltransferase (ChAT) Interneurons

Next, the consequences of specifically inhibiting ChAT interneurons were explored, employing Cre-dependent eNpHR3.0 expression in vivo.

Materials and Methods

Mice, optrode recordings, and brain slices were prepared as above.

Results

Figure 3B:
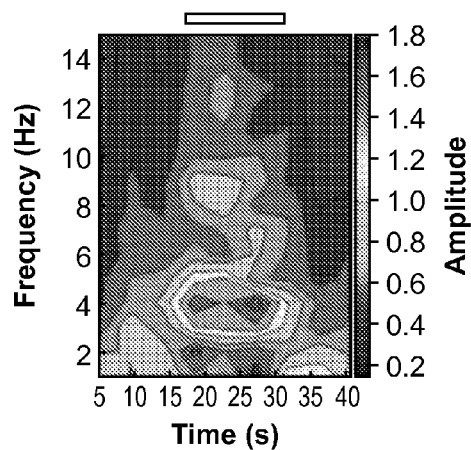
Figure 3C:
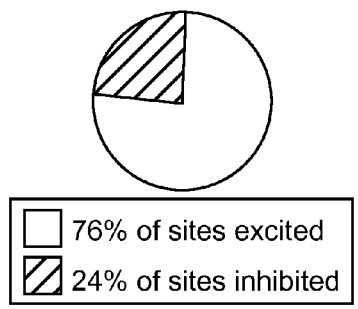
Figure 3D:
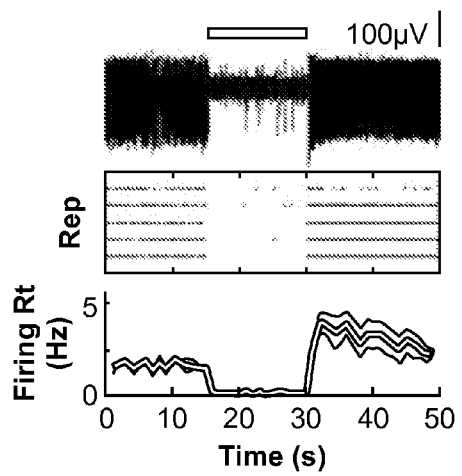
Figure 3E:
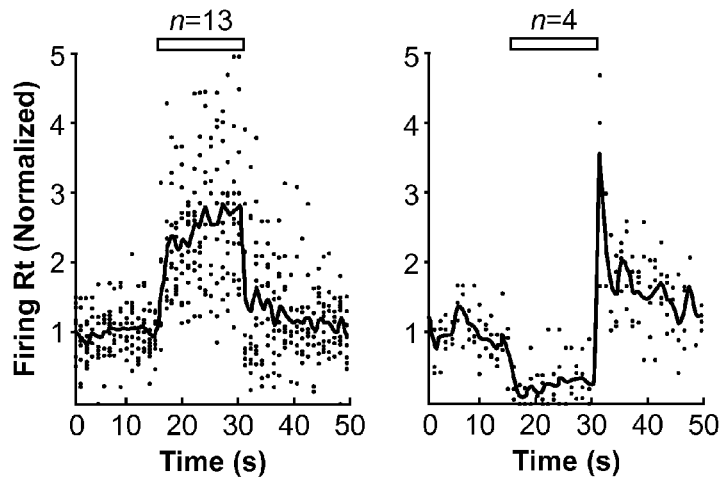

In contrast to what was observed with ChAT neuron excitation, firing of NAc neurons was typically increased in likely MSNs by optogenetic inhibition of the ChAT cells; a representative cell is shown in FIG. 3A). Power spectral analysis revealed a striking frequency peak in the firing pattern at ~4 Hz in these in vivo recordings (FIG. 3B). Summary data are presented in FIG. 3C; across the population of significantly modulated sites, most neurons were excited by the optogenetic inhibition of ChAT neurons (n=17). We were able to obtain a single-unit recording from a rare putative ChAT interneuron, which was completely shut down by eNpHR3.0 (FIG. 3D) and displayed the long action potential duration characteristic of ChAT interneurons (37) (2.0 ms for this cell, while spike durations for MSNs in our recordings ranged from 1.1-1.7 ms). Summary data (FIG. 3E) show the dynamics of excitation and inhibition for all recorded sites, illustrating the dominant pattern of excitation (firing increased by 130.5+/−17.5% in sites that were excited by light). Taken together, the results from in vivo optogenetic excitation and inhibition of ChAT neurons are consistent with our findings from slice physiology, pointing to a surprisingly powerful role for these rare cells in controlling local circuit activity in the NAc.

Example 4

Effects of Cholinergic Interneuron Manipulation on Reward Behavior in Freely Moving Mice It was decided to test if this potent NAc control mechanism was relevant to accumbens-dependent reward behavior in freely moving mice. First the effect of acutely administered cocaine on activity of these identified ChAT neurons in acute NAc slices was tested. Next, eNpHR3.0 was used to test for causal roles in either this cocaine-induced activity or baseline activity of ChAT cells in the reward-related behavior of cocaine conditioned place preference (CPP), in which animals learn to associate an environment with cocaine.

Materials and Methods

Conditioned Place Preference

All behavioral experiments were performed 4-6 weeks after virus injections during the animals' dark (active) cycle. The conditioned place preference (CPP) protocol was similar to those from previous reports of unbiased, balanced place-preference (Bardo et al., Neurosci Biobehav Rev 19, 39-51 (1995)). The CPP apparatus consisted of a rectangular chamber with one side compartment measuring 23 cm×26 cm with black walls and a grating on the floor, a central compartment measuring 23 cm×11 cm with clear plexiglass walls and a plexiglass floor, and another side compartment measuring 23 cm×26 cm with white walls and a punched metal floor. Mouse position during each day of testing was monitored using a video-tracking system. Floors were selected such that mice did not display average baseline bias for a particular chamber, and any mouse with a strong initial preference for a chamber was excluded (more than five minute difference spent in the side chambers on day 1). The CPP test consisted of the following. On day 1, each mouse was placed in the central chamber and allowed to freely explore the entire apparatus for 20 minutes (pre-test). Day 2 consisted of conditioning. In the morning, each mouse was confined to one of the side chambers for 20 minutes, and in the afternoon was confined to the other side chamber for the same period of time. For the cocaine CPP experiments, subjects received i.p. cocaine injections (20 mg/kg unless otherwise specified) before placement in one chamber, while subjects received i.p. saline injections of an equivalent volume before placement in the other chamber. (This concentration of cocaine allowed for robust conditioning with a single day of training in control animals, facilitating the optogenetic intervention). Mice received either yellow or bluelight during the 20 minutes in which they explored the compartment that was paired with the cocaine injection, whereas they were connected to a "dummy" fiber that was not emitting light when exploring the other chamber. The intensity of the blue light (470 nm) was chosen to generate power density of 140-200 mW/mm$^2$ at the fiber tip, which should correspond to a power density of ~4-7 mW/mm$^2$ in the middle of the NAc. The intensity of the yellow light (590 nm) was chosen so that there was a power density of 70-140 mW/mm$^2$ at the fiber tip, which should correspond to a power density of ~3.5-7 mW/mm$^2$ in the middle of the NAc. On day 3, exactly as in day 1, mice were placed in the center chamber and allowed to freely explore the entire apparatus for 20 min (posttest). CPP experiments that did not involve cocaine were performed identically, except that the i.p. injections of cocaine or saline were omitted.

Open Field

The open field test was conducted in an open plastic arena (50 cm long×50 cm wide×40 cm deep). Mice were individually placed in the center of the chamber and allowed to freely explore for 3 min Activity in both the center and periphery of the field was measured using an automated video-tracking system (Viewer II, BiObserve). Time in center refers to time the mouse spent in the central 35×35 cm area of the open field.

Fear Conditioning

The fear conditioning apparatus consisted of a square conditioning cage (18×18×30 cm) with a grid floor wired to a shock generator and a scrambler, surrounded by an acoustic chamber. The top of the chamber was modified to enable light delivery during training by introducing an opening for the fiber. All mice received continuous yellow light during training but not during testing on the following day (590 nm; same power density as for the CPP experiments). To induce fear conditioning, mice were placed in the cage for 120 seconds; a pure tone (2.9 KHz) was then played for 20 seconds, followed immediately by a 2 second foot-shock (0.5 mA). This procedure was repeated, and 30 seconds after the delivery of the second shock mice were returned to their home cage. Freezing (complete immobility) was quantified for the 30 seconds before the first tone on the conditioning day to assess baseline freezing, as well as the 30 seconds immediately after the final shock on the conditioning day to assess immediate freezing. Contextual and auditory-cued fear conditioning were assessed the day after conditioning. To test contextual fear conditioning, mice were placed in the original conditioning cage, and freezing was measured for 5 min. To test auditory-cued fear conditioning, mice were placed in a different context: a pyramid shaped cage with a plexiglass floor. As a control for the influence of the novel environment, freezing was measured for 2 5 minutes in this new cage, and then the 2.9 KHz tone was played for 2 5 minutes, during which conditioned freezing was measured.

Results

In ventro-medial NAc ChAT cells, cocaine was found to markedly increase spontaneous firing (representative ChAT neuron shown in FIGS. 4, A and B). Summary data revealed that cocaine increased firing rates from 0.60±0.41 Hz to 1.74±0.56 Hz at 10 min in ChAT neurons (n=7; P<0.005, paired t test), while in the control group of cells receiving only vehicle, firing rates decreased from 0.69±0.24 Hz to 0.09±0.09 Hz over the same time period (n=6; P<0.05 comparing the two groups, two-tailed t test) (FIG. 4C).

Figure 8A:
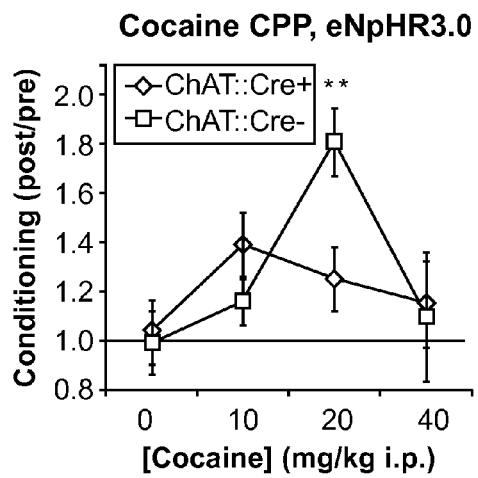
FIG. 8 depicts modulation of ChAT interneurons over a range of cocaine-CPP parameters. (A): Dose-response curve for cocaine CPP during eNpHR3.0-mediated inhibition of the ChAT interneurons. Cocaine CPP is significantly decreased in ChAT::Cre+ mice for the standard rewarding dose of 20 mg/kg i.p. (p<0.01), but not at other concentrations thought to be anxiogenic or insufficient (590 nm light, constant illumination; see Table 2, infra). (B): Stimulation of ChAT neurons with ChR2 does not drive place preference by itself. (470 nm light, 5 ms pulse width, 10 sec of 10 Hz stimulation every 30 sec; n=4,p>0.05 two-tailed t-test). (C): Stimulation of ChAT neurons at 10 Hz with ChR2 does not significantly modulate cocaine place preference for i.p. 10 mg/kg cocaine. (470 nm light, 5 ms pulse width, constant 10 Hz stimulation during cocaine conditioning; ChAT::Cre+ n=6, ChAT::Cre− n=6; p>0.05 two-tailed t-test). (D): Stimulation of ChAT neurons at 10 Hz with ChR2 does not significantly modulate cocaine place preference for i.p. 20 mg/kg cocaine (470 nm light, 5 ms pulse width, steady 10 Hz stimulation during cocaine conditioning; ChAT::Cre+ n=4, ChAT::Cre− n=3; p>0.05 two-tailed t-test).
Figure 8B:
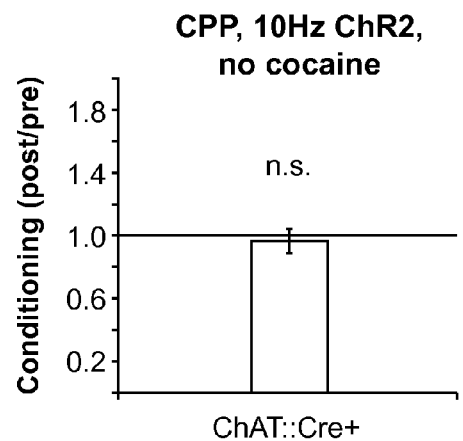
Figure 8C:
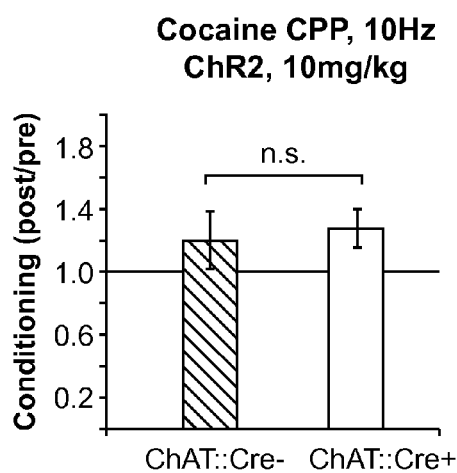
Figure 8D:
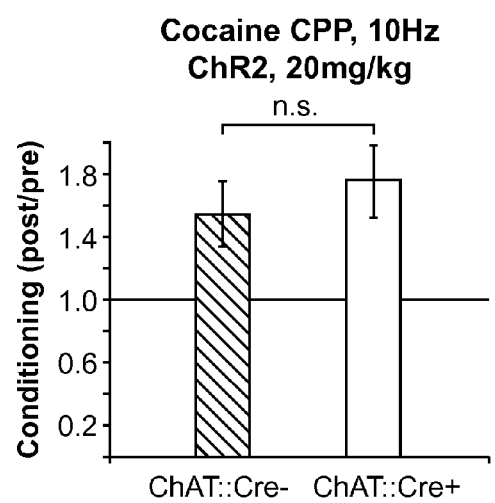
Figure 9A:
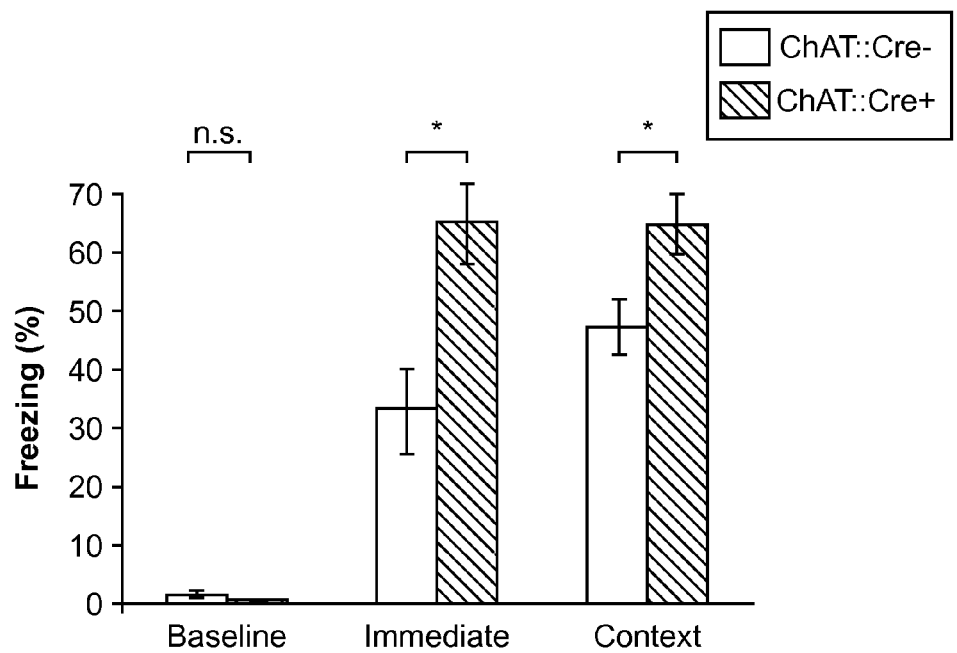
FIG. 9 depicts inhibition of ChAT interneurons with eNphR3.0 does not impair contextual or auditory-cued fear conditioning. (A): Percentage time spent freezing was quantified in a standard contextual fear conditioning paradigm. "Baseline" refers to the 30 seconds preceding the first toneshock pairing "Immediate" refers to the 30 seconds immediately after the second (and final) tone-shock pairing. "Context" refers to freezing to the same context on the day after the conditioning session. ChAT::Cre+ mice exhibited enhanced immediate and context freezing. (n=9 ChAT::Cre+; n=8 ChAT::Cre−; two-tailed t-test; p<0.05 comparing ChAT::Cre+ and ChAT::Cre− for immediate and context freezing). (B): Percentage time spent freezing for the auditory-cued fear conditioning paradigm. "Pre-tone" refers to the 2.5 minutes in the new context before the onset of the tone; "Tone" refers to the 2.5 minutes during tone (n=9 ChAT::Cre+; n=8 ChAT::Cre−; two tailed t-test; p>0.05 comparing ChAT::Cre+ and ChAT::Cre−).
Figure 9B:
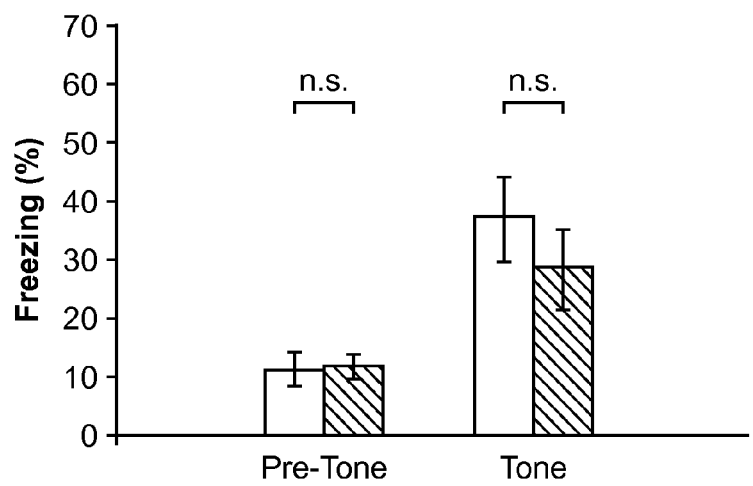

We next used eNpHR3.0 to test for causal roles of either this cocaine-induced activity, or baseline activity, of ChAT cells in the reward-related behavior of conditioned place preference (CPP), in which animals learn to associate an environment with cocaine. After injecting virus and implanting cannulae bilaterally (FIG. 4D) to silence ChAT neurons during cocaine exposure (FIG. 4E), we found that mice that expressed eNpHR3.0 in the ChAT cells exhibited significantly less cocaine-induced conditioned place preference (CPP) than did their control (Cre recombinase-negative) littermates which had received the same virus, surgery, and light-delivery protocol [20 mg/kg intraperitoneally (ip), FIGS. 4, F and G; n=10 ChAT::Cre$^+$, n=12 ChAT::Cre$^-$ (left panel); P<0.01 for two-tailed t test; three cohorts; see also FIG. 6A. We observed no behavioral effect of inhibiting the ChAT cells in the absence of cocaine, and ChAT neuron inhibition by itself was not aversive, as conditioning with eNpHR3.0 alone did not affect place preference (FIG. 4G, right panel; n=9 ChAT::Cre$^+$, n=7 ChAT::Cre$^-$; P>0.05 for two-tailed t test; three cohorts; FIG. 6B; see also FIG. 8A for cocaine dose-response curve). Activation of the cells with ChR2 at 10 Hz was not sufficient to drive place preference by itself or enhance cocaine place preference (10 and 20 mg/kg ip, FIG. 8B to D; Table 4), with our data from ChAT cell inhibition instead demonstrating necessity of these cells. Finally, in control experiments, we found that ChAT neuron inhibition by itself had no effect on mobility or anxiety in the open field (FIGS. 4, H and J), and contextual- and auditory-cued fear conditioning were not disrupted by inhibition of the ChAT cells (FIG. 9).

TABLE 4

Total time spent on the cocaine-paired side on the testing day of the cocaine place preference paradigm (for various cocaine concentrations) when inhibition of the ChAT neurons (with eNphR3.0) was paired with cocaine exposure.

| | mg/kg | 0 | 10 | 20 | 40 |
|---|---|---|---|---|---|
| ChAT::Cre+ | N | | 11 | 10 | 4 |
| | Conditioned side (min) | | 10.3 | 10.7 | 10.5 |
| ChAT::Cre− | N | | 12 | 12 | 3 |
| | Conditioned side (min) | | 8.5 | 14.2 | 9.2 |

Discussion

Together, these results from specific and acute optogenetic control of the defined ChAT neuron population point to a powerful role for these rare and sparsely distributed neurons in controlling local circuit activity and implementing reward-related behavior in freely moving mammals. The fact that acute silencing of ChAT interneurons disrupts drug-related learning without affecting place preference in the absence of drug suggests the tantalizing possibility that control over this microcircuit could be used to selectively disrupt the addictive properties of drugs of abuse without affecting appetitive or aversive responses in general, a possibility that would be of immense clinical benefit. Interestingly, the behavioral results do not support conclusions arising from chronic ablation of the cholinergic interneurons (34), but instead are more consistent with interpretations arising from faster but less cellularly-targeted pharmacological modulation in the NAc (23-26). Ablation of the cholinergic interneurons could lead to indirect effects, such as a compensatory increase in dopamine in the NAc, which could in turn enhance cocaine reward. In fact, a fundamental difference between acute and chronic manipulations could explain clinically-relevant apparent contradictions in our understanding of acetylcholine/dopamine balance in the brain, such as the finding that an acute increase in nicotine (presumably acting upon cholinergic receptors) causes a corresponding acute increase in dopamine (54, 55), whereas chronic changes in dopamine or acetylcholine levels can cause opposing changes in the levels of the other neuromodulator (56), for example as seen in the dopamine depletion of Parkinson's disease (57).

The speed and specificity of this approach may enable elucidation of the causal role of acetylcholine neurons, in both healthy and diseased neural circuitry, in other regions of the nervous system as well. For example, much like the dopamine neurons that project to striatum (58, 59), the ChAT interneurons in dorsal striatum are thought to carry information about rewards and stimuli that predict rewards (60). Such stimuli generate a brief pause in the activity of striatal tonically-active neurons in primates, often preceded and followed by an excitatory burst of activity (16, 17). Structural homology between dorsal and ventral striatum suggests that similar principles to those outlined here for NAc could extend to ChAT cell activity in dorsal striatum, which indeed appears to be the case (English et al., accompanying manuscript). These results, taken together with our findings that the activity of these cells in the NAc drives powerful time-locked inhibition and controls reward-learning behavior, suggest that ChAT neurons serve as a potent control node suitable for versatile neuromodulatory regulation of circuit activity and behavior in the mammalian brain.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. S. Ikemoto, R. A. Wise, *Neuropharmacology* 47 Suppl 1, 190-201 (2004).
2. J. Changeux, *C. R. Biol* 332, 421-425 (2009).
3. M. P. Kilgard, M. M. Merzenich, *Science* 279, 1714-1718 (1998).
4. J. S. Bakin, N. M. Weinberger, *Proc. Natl. Acad. Sci. U.S.A* 93, 11219-11224 (1996).
5. M. E. Hasselmo, L. M. Giocomo, *I MoL Neurosci.* 30, 133-135 (2006).
6. U. Maskos, *Br. J. Pharmacol* 153 Suppl 1, S438-445 (2008).
7. M. R. Picciotto et al., *Nature* 391, 173-177 (1998).
8. J. M. Fellous, T. J. Sejnowski, *Hippocampus* 10, 187-197 (2000).
9. J. P. Changeux et al., *Cold Spring Harb. Symp. Quant. Biol* 61, 343-362 (1996).
10. J. P. Changeux et al., *Brain Res. Brain Res. Rev* 26, 198-216 (1998).
11. A. Kamsler, T. J. McHugh, D. Gerber, S. Y. Huang, S. Tonegawa, *Proc. Natl. Acad. Sci. U.S.A* 107, 1618-1623 (2010).
12. S. J. Moore, D.C. Cooper, N. Spruston, *Neuron* 61, 287-300 (2009).
13. P. H. Tiesinga, J. M. Fellous, J. V. Jose, T. J. Sejnowski, *Hippocampus* 11, 251-274 (2001).
14. B. J. Everitt, T. W. Robbins, *Annu. Rev. Psychol.* 48, 649-684 (1997).
15. Z. Wang et al., *Neuron* 50, 443-452 (2006).
16. G. Morris, D. Arkadir, A. Nevet, E. Vaadia, H. Bergman, *Neuron* 43, 133-143 (2004).
17. T. Aosaki et al., *J. Neurosci* 14, 3969-3984 (1994).
18. M. L. Furey, P. Pietrini, J. V. Haxby, W. C. Drevets, *Neuropsychopharmacology* 33, 913-923 (2008).
19. S. G. Anagnostaras et al., *Nat. Neurosci* 6, 51-58 (2003).
20. S. Ikemoto, B. S. Glazier, J. M. Murphy, W. J. McBride, *Physiol. Behav* 63, 811-814 (1998).
21. M. J. Williams, B. Adinoff, *Neuropsychopharmacology* 33, 1779-1797 (2008).
22. A. Vale-Martinez, M. G. Baxter, H. Eichenbaum, *Eur. I Neurosci* 16, 983-998 (2002).
23. V. Zachariou et al., *Neuropsychopharmacology* 24, 576-589 (2001).
24. W. E. Pratt, R. C. Spencer, A. E. Kelley, *Behav. Neurosci* 121, 1215-1223 (2007).
25. J. A. Crespo, K. Sturm, A. Saria, G. Zernig, *J. Neurosci* 26, 6004-6010 (2006).

26. W. E. Pratt, A. E. Kelley, *Behav. Neurosci* 118, 730-739 (2004).
27. F. E. Pontieri, G. Tanda, F. Orzi, G. Di Chiara, *Nature* 382, 255-257 (1996).
28. M. B. Kelz et al., *Nature* 401, 272-276 (1999).
29. B. T. Chen, F. W. Hopf, A. Bonci, *Ann. N.Y. Acad. Sci.* 1187, 129-139 (2010).
30. R. A. Wise, *NIDA Res. Monogr* 50, 15-33 (1984).
31. A. A. Grace, C. R. Gerfen, G. Aston-Jones, *Adv. Pharmacol* 42, 655-670 (1998).
32. T. W. Robbins, K. D. Ersche, B. J. Everitt, *Ann. N.Y. Acad. Sci.* 1141, 1-21 (2008).
33. E. J. Nestler, G. K. Aghajanian, *Science* 278, 58-63 (1997).
34. T. Hikida et al., *Proc. Natl. Acad. Sci. U.S.A* 98, 13351-13354 (2001).
35. V. V. Rymar, R. Sasseville, K. C. Luk, A. F. Sadikot, *J. Comp. Neurol* 469, 325-339 (2004).
36. J. M. Tepper, J. P. Bolam, *Curr. Opin. Neurobiol* 14, 685-692 (2004).
37. F. Zhou, C. J. Wilson, J. A. Dani, *J. Neurobiol* 53, 590-605 (2002).
38. F. Zhou, C. Wilson, J. A. Dani, *Neuroscientist* 9, 23-36 (2003).
39. T. KoOs, J. M. Tepper, *J. Neurosci* 22, 529-535 (2002).
40. M. de Rover, J. C. Lodder, K. S. Kits, A. N. M. Schoffelmeer, A. B. Brussaard, *Eur. J. Neurosci* 16, 2279-2290 (2002).
41. N. Uchimura, R. A. North, *J. Physiol. (Lond.)* 422, 369-380 (1990).
42. Y. Zhang, T. G. Oertner, *Nat. Methods* 4, 139-141 (2007).
43. F. Zhang et al., *Nat Protoc* 5, 439-456 (2010).
44. A. R. Adamantidis, F. Zhang, A. M. Aravanis, K. Deisseroth, L. de Lecea, *Nature* 450, 420424 (2007).
45. S. Gong et al., 0.1 *Neurosci* 27, 9817-9823 (2007).
46. H. Tsai et al., *Science* 324, 1080-1084 (2009).
47. D. Atasoy, Y. Aponte, H. H. Su, S. M. Stemson, I *Neurosci* 28, 7025-7030 (2008).
48. G. Nagel et al., *Proc. Natl. Acad. Sci. U.S.A* 100, 13940-13945 (2003).
49. E. S. Boyden, F. Zhang, E. Bamberg, G. Nagel, K. Deisseroth, *Nat. Neurosci* 8, 1263-1268 (2005).
50. V. Gradinaru et al., *Cell* 141, 154-165 (2010).
51. Y. Kawaguchi, *J. Neurosci* 13, 4908-4923 (1993).
52. C. J. Wilson, H. T. Chang, S. T. Kitai, *J. Neurosci* 10, 508-519 (1990).
53. H. Inokawa, H. Yamada, N. Matsumoto, M. Muranishi, M. Kimura, *Neuroscience* (2010) www.ncbi.nlm.nih.gov-.laneproxy.stanford.edu/pubmed/20371269.
54. M. Nisell, M. Marcus, G. G. Nomikos, T. H. Svensson, *J Neural Transm* 104, 1-10 (1997).
55. R. Exley, M. A. Clements, H. Hartung, J. M. McIntosh, S. J. Cragg, *Neuropsychopharmacology* 33, 2158-2166 (2008).
56. A. Hrabovska et al., *Chem. Biol. Interact* 183, 194-201 (2010).
57. B. G. Hoebel, N. M. Avena, P. Rada, *Curr Opin Pharmacol* 7, 617-627 (2007).
58. W. Schultz, *J Neurophysiol* 80, 1-27 (1998).
59. W. Pan, R. Schmidt, J. R. Wickens, B. I. Hyland, *J. Neurosci* 25, 6235-6242 (2005).
60. M. Kimura, J. Rajkowski, E. Evarts, *Proc. Natl. Acad. Sci. U.S.A* 81, 4998-5001 (1984).

---

What is claimed is:

1. A method for disrupting reward-related behavior associated with the nucleus accumbens or the striatum in a mammal, the method comprising:
   a) directly administering to cholinergic interneurons in the nucleus accumbens or the striatum in the mammal a viral vector comprising a nucleotide sequence encoding a hyperpolarizing light-responsive opsin polypeptide, wherein the nucleotide sequence is operably linked to a choline acetyltransferase promoter, wherein the hyperpolarizing light-responsive opsin polypeptide is expressed on the cell membrane of the cholinergic interneurons, wherein the hyperpolarizing light-responsive opsin polypeptide is capable of inducing membrane hyperpolarization of the interneurons when the interneurons are illuminated with light; and
   b) activating the hyperpolarizing light-responsive opsin polypeptide with light emitted by a light-generating device implanted near the cholinergic interneurons, wherein said activating hyperpolarizes the cholinergic interneurons and disrupts at least one reward-related behavior associated with the nucleus accumbens or the striatum in the mammal.

2. The method of claim 1, wherein the viral vector is selected from the group consisting of an adenoassociated virus vector, a retroviral vector, an adenoviral vector, a herpes simplex virus vector, and a lentiviral vector.

3. The method of claim 1, wherein the hyperpolarizing light-responsive opsin protein is selected from the group consisting of NpHR, BR, AR, and GtR3.

4. The method of claim 3, wherein NpHR is selected from the group consisting of NpHR2.0, NpHR3.0, and NpHR3.1.

5. The method claim 1, wherein the reward-related behavior is drug-related addictive behavior.

6. The method of claim 1, wherein the mammal is a human.

7. The method of claim 1, wherein the mammal is a non-human mammal.

8. The method of claim 1, wherein the hyperpolarizing light-responsive opsin polypeptide is a light-responsive chloride ion pump and comprises an amino acid sequence having at least 90% amino acid sequence identity to the amino acid sequence set forth in SEQ ID NO: 1.

9. The method of claim 8, wherein the hyperpolarizing light-responsive opsin poplypeptide comprises an endoplasmic reticulum (ER) export signal.

10. The method of claim 9, wherein the ER export signal comprises the amino acid sequence FXYENE, wherein X is any amino acid.

11. The method of claim 8, wherein the hyperpolarizing light-responsive opsin polypeptide comprises a trafficking signal that enhances transport of the opsin polypeptide to the plasma membrane.

12. The method of claim 1, wherein the hyperpolarizing light-responsive opsin polypeptide comprises an amino acid sequence having at least 90% amino acid sequence identity to the amino acid sequence set forth in SEQ ID NO: 4.

13. The method of claim 12, wherein the hyperpolarizing light-responsive opsin polypeptide comprises at least one of an endoplasmic reticulum export signal and a trafficking signal that enhances transport of the opsin polypeptide to the plasma membrane.

14. The method of claim 1, wherein the light-generating device comprises a light emitting diode.

15. The method of claim 1, wherein the light-generating device comprises a solid state laser diode.

* * * * *